US010973212B2

(12) United States Patent
Shen et al.

(10) Patent No.: US 10,973,212 B2
(45) Date of Patent: Apr. 13, 2021

(54) GENETICALLY MODIFIED NON-HUMAN ANIMAL WITH HUMAN OR CHIMERIC SIRPA

(71) Applicant: Biocytogen Pharmaceuticals (Beijing) Co., Ltd., Beijing (CN)

(72) Inventors: Yuelei Shen, Beijing (CN); Yang Bai, Beijing (CN); Meiling Zhang, Beijing (CN); Rui Huang, Beijing (CN); Chengzhang Shang, Beijing (CN); Yanan Guo, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/436,545

(22) Filed: Jun. 10, 2019

(65) Prior Publication Data

US 2019/0373867 A1 Dec. 12, 2019

Related U.S. Application Data

(63) Continuation of application No. PCT/CN2018/081629, filed on Apr. 2, 2018.

(30) Foreign Application Priority Data

Mar. 31, 2017 (CN) ......................... 201710205646.7
Oct. 13, 2017 (CN) ......................... 201710953316.6
Oct. 27, 2017 (CN) ......................... 201711038308.5
Oct. 27, 2017 (CN) ......................... 201711039543.4
Mar. 30, 2018 (CN) ......................... 201810295709.7
Mar. 30, 2018 (CN) ......................... 201810296193.8

(51) Int. Cl.
*A01K 67/027* (2006.01)
*A61K 49/00* (2006.01)

(52) U.S. Cl.
CPC ...... *A01K 67/0278* (2013.01); *A61K 49/0008* (2013.01); *A01K 2217/072* (2013.01); *A01K 2217/075* (2013.01); *A01K 2227/105* (2013.01); *A01K 2267/0393* (2013.01)

(58) Field of Classification Search
CPC ................................................. A01K 67/0278
See application file for complete search history.

(56) References Cited

U.S. PATENT DOCUMENTS 4,683,195 A 7/1987 Mullis et al.
2015/0106961 A1 4/2015 Rojas et al.
2016/0345549 A1 12/2016 Gurer
2019/0343097 A1 11/2019 Shen

FOREIGN PATENT DOCUMENTS

CN 104039821 9/2014
CN 104561095 4/2015
CN 104904661 9/2015
WO WO 2007033221 3/2007
WO WO-2010070047 A1 * 6/2010 .............. A61P 17/06
WO WO 2012040207 3/2015
WO WO 2015042557 3/2015
WO WO-2015042557 A1 * 3/2015 ......... A61K 49/0008
WO WO 2016089692 5/2016
WO WO-2016089692 A1 * 6/2016 ......... A01K 67/0278
WO WO 2016094679 6/2016
WO WO 2018001241 1/2018
WO WO 2018041118 3/2018
WO WO 2018041119 3/2018
WO WO 2018041120 3/2018
WO WO 2018041121 3/2018
WO WO 2018068756 4/2018
WO WO 2018086583 5/2018
WO WO 2018086594 5/2018
WO WO 2018113774 6/2018
WO WO 2018121787 7/2018

OTHER PUBLICATIONS

Ivics et al. (2014, Nature Protocols, vol. 9(4), pp. 810-827) (Year: 2014).*
West et al., 2016, J. Equine Vet. Sci., vol. 41, pp. 1-12 (Year: 2016).*
Meng et al. (2015, J. Animal Sci. and Biotech., pp. 1-7) (Year: 2015).*
Brevini et al., 2010, Theriogenology, vol. 74, pp. 544-550 (Year: 2010).*
Paris et al. (2010, Theriogenology, vol. 74, pp. 516-524) (Year: 2010).*
Gomez et al. (2010, Theriogenology, vol. 74, pp. 498-515) (Year: 2010).*
Buta et al. (2013, Stem Cell Res., vol. 11, pp. 552-562) (Year: 2013).*
Garcia-Arocena D. (2014, The Jackson Laboratory, Same Mutation, Different Phenotype?) (Year: 2014).*
Heimain-Patterson et al. (2011, Amyotrophic Lateral Schlerosis, vol. 00, pp. 1-8) (Year: 2011).*
2004, Barthold S., Genetica, vol. 122, pp. 75-88 (Year: 2004).*
Tong et al. (2010, Nature, vol. 467(7312), pp. 211-213) (Year: 2010).*
Hong et al. (2012, Stem Cells and Development, vol. 21(9), pp. 1571-1586) (Year: 2012).*
Liu C. (2013, Methods Mol. Biol., vol. 1027, pp. 183-201). (Year: 2013).*
Ansell et al., "A phase 1 study of TTI-621, a novel immune checkpoint inhibitor targeting CD47, in patients with relapsed refractory hematologic malignancies," Blood, 2016, 1812.
Auerbach et al., "Establishment and Chimera Analysis of 129/SvEv- and C57BL/6-Derived mouse embryonic stem cell lines," BioTechniques, 2000, 29:1024-1032.

(Continued)

*Primary Examiner* — Thaian N. Ton
*Assistant Examiner* — David A. Montanari
(74) *Attorney, Agent, or Firm* — Fish & Richardson P.C.

(57) ABSTRACT

The present disclosure relates to genetically modified non-human animals that express a human or chimeric (e.g., humanized) SIRPα, and methods of use thereof.

19 Claims, 28 Drawing Sheets

Specification includes a Sequence Listing.

(56) References Cited

OTHER PUBLICATIONS

Barclay et al., "The interaction between signal regulatory protein alpha (SIRPa) and CD47: structure, function, and therapeutic target," The Annual Review of Immunology, 2013, 32:25-50.
Festing et al., "Revised nomenclature for strain 129 mice," Mammalian Genome, 1999, 10:836.
Huang et al., "Targeting CD47: the achievements and concerns of current studies on cancer immunotherapy," Journal of thoracic diseases, 2017, 9(2):E168.
Inagaki et al., "SHPS-1 regulates integrin-mediated cytoskeletal reorganization and cell motility," The Embo Journal, 2000, 19(24):6721-6731.
International Search Report and Written Opinion in International Appln. No. PCT/CN2018/081628, dated Jun. 27, 2018, 12 pages.
International Search Report and Written Opinion in International Appln. No. PCT/CN2018/081629, dated Jun. 27, 2018, 13 pages.
Ito et al., NOD/SCID/ ycnull mouse: an excellent recipient mouse model for engraftment of human cells, Blood, 2002, 100(9):3175-3182.
Legrand et al., "Functional CD47/signal regulatory protein alpha (SIRPa) interaction is required for optimal human T- and natural killer-(NK) cell homeostasis in vivo," PNAS, 2011, 108(32):13224-13229.
Liu et al., "Is CD47 an innate immune checkpoint for tumor evasion?" Journal of hematology & oncology, 2017, 10(1):12.
Liu et al., "Pre-clinical development of a humanized anti-CD47 antibody with anti-cancer therapeutic potential," PloS one, 2015, 10(9):e013745.
Murata et al., "Autoimmune animal models in the analysis of the CD47-SIRPa signaling pathway," Methods, 2013, pp. 1-6.
Seiffert et al. "Signal-regulatory protein a (SIRPa) but not SIRPb is involved in T-cell activation, binds to CD47 with high affinity, and is expressed on immature CD34+ CD38− hematopoietic cells." Blood, 2001, 97(9):2741-2749.
Shultz et al., "Humanized mice for immune system investigation: progress, promise, and challenges," Nature Reviews Immunology, 2012, 12:786-798.
Strowig et al., "Transgenic expression of human signal regulatory protein alpha in Rag2-/-yc-/-mice improves engraftment of human hematopoietic cells in humanized mice," PNAS, 2011, 108(32):1-6.
Yanagita et al. "Anti-SIRPa antibodies as a potential new tool for cancer immunotherapy." JCI insight 2.1 (2017).
Yin et al., "Delivery technologies for genome editing," Nature Reviews Drug Discovery, 2017, 16(6):387-399.
Zeng et al., "Generation and expression analysis of human [*Homo sapiens*] CD47 transgenic Bama Miniature Pig (*Sus scrofa*)," Journal of Agricultural Biotechnology, 2016, 24(8):1251-1258 (with English abstract).
Harms et al., "Mouse Genome Editing Using the CRISPR/Cas System," Curr Protoc Hum Genetics, 2014, 15.7.1-15.7.27.
Schilit et al., "Pronuclear Injection-Based Targeted Transgenesis," Curr Protoc Hum Genet., Oct. 2016, 91(1):15.10.1-15.10.28.
Tena et al., "Transgenic expression of human CD47 markedly increases engraftment in a murine model of pig-to-human hematopoietic cell transplantation," Am. J. Transplantation, 2014, 14(12):2713-2722.
GenBank Accession No. AB012693.1, "Mus musculus mRNA for CD47, complete cds," Mar. 30, 1998, 3 pages.
GenBank Accession No. BC062197.1, "Mus musculus signal-regulatory protein alpha, mRNA (cDNA clone MGC:70224 IMAGE:5368250), complete cds," GenBank, Nov. 13, 2003, 4 pages.
GenBank Accession No. KJ903815.1, "Synthetic construct *Homo sapiens* clone ccsbBroadEn_13209 SIRPA gene, encodes complete protein," GenBank, May 28, 2014, 3 pages.
GenBank Accesssion No. LN680437.1, "*Homo sapiens* mRNA for CD47," GenBank, Nov. 14, 2014, 2 pages.
Murata et al., "The CD47-SIRPα signalling system: its physiological roles and therapeutic application," The Journal of Biochemistry, Jun. 1, 2014, 155(6):335-344.

* cited by examiner

| Score | Expect | Method | Identities | Positives | Gaps |
|---|---|---|---|---|---|
| 631 bits(1628) | 0.0 | Compositional matrix adjust. | 332/511(65%) | 394/511(77%) | 9/511(1%) |

```
Mouse  1    MEPAGPAPGRLGPLLLCLLLSASCFCTGATGKELKVTQPEKSVSVAAGDSTVLNCTLTSL  60
            MEPAGPAPGRLGPLL  LL ++  +   A  +EL+V QP+KSV VAAG++  L CT TSL
Human  1    MEPAGPAPGRLGPLLCLLLAASCAWSGVAGEEELQVIQPDKSVLVAAGETATLRCTATSL  60

Mouse  61   LPVGPIRWYRGVGPSRLLIYSFAGEYVPRIRNVSDTTKRNNMDFSIRISNVTPADAGIYY  120
            +PVGPI+W+RG GP R LIY+     + PR+  VSD TKRNNMDFSIRI N+TPADAG YY
Human  61   IPVGPIQWFRGAGPGRELIYNQKEGHFPRVTTVSDLTKRNNMDFSIRIGNITPADAGTYY  120

Mouse  121  CVKFQKGSSEPDTEIQSGGGTEVYVLAKPSPPEVSGPADRGIPDQKVNFTCKSHGFSPRN  180
            CVKF+KGS + D E +SG GTE+ V AKPS P VSGPA R  P   V+FTC+SHGFSPR+
Human  121  CVKFRKGSPD-DVEFKSGAGTELSVRAKPSAPVVSGPAARATPQHTVSFTCESHGFSPRD  179

Mouse  181  ITLKWFKDGQELHPLETTVNPSGKNVSYNISSTVRVVLNSMDVNSKVICEVAHITLDRSP  240
            ITLKWFK+G EL   +T V+P G++VSY+I ST +VVL   DV+S+VICEVAH+TL   P
Human  180  ITLKWFKNGNELSDFQTNVDPVGESVSYSIHSTAKVVLTREDVHSQVICEVAHVTLQGDP  239

Mouse  241  LRGIANLSNFIRVSPTVKVTQQSPTSMNQVNLTCRAERFYPEDLQLIWLENGNVSRNDTP  300
            LRG ANLS  IRV PT++VTQQ   + NQVN+TC+  +FYP+ LQL WLENGNVSR +T
Human  240  LRGTANLSETIRVPPTLEVTQQPVRAENQVNVTCQVRKFYPQRLQLTWLENGNVSRTETA  299

Mouse  301  KNLTKNTDGTYNYTSLFLVNSSAHREDVVFTCQVKHDQQPAITRNHTVLGFAHSSDQGSM  360
              +T+N DGTYN+ S  LVN SAHR+DV  TCQV+HD QPA++++H +   AH  +QGS
Human  300  STVTENKDGTYNWMSWLLVNVSAHRDDVKLTCQVEHDGQPAVSKSHDLKVSAHPKEQGS-  358
```

FIG. 25 Continued

```
Mouse   361   QTFPDNNATHNWNVFIGVGVACALLVVLLMAALYLLRIKQKKAKGSTSSTRLHEPEKNAR   420
               T  +N  ++  N++I VGV C LLV LLMAALYL+RI+QKKA+GSTSSTRLHEPEKNAR
Human   359   NTAAENTGSNERNIYIVVGVVCTLLVALLMAALYLVRIRQKKAQGSTSSTRLHEPEKNAR   418

Mouse   421   EITQIQDTNDINDITYADLNLPKEKKPAPRAPEPNNHTEYASIETGKVPRPEDTLTYADL   480
              EITQ     D NDITYADLNLPK KKPAP+A EPNNHTEYASI+T   P  EDTLTYADL
Human   419   EITQ-----DTNDITYADLNLPKGKKPAPQAAEPNNHTEYASIQTSPQPASEDTLTYADL   473

Mouse   481   DMVHLSRA--QPAPKPEPSFSEYASVQVQRK   509
              DMVHL+R   QPAPKPEPSFSEYASVQV RK
Human   474   DMVHLNRTPKQPAPKPEPSFSEYASVQVPRK   504
```

FIG. 26

| Score | Expect | Method | Identities | Positives | Gaps |
|---|---|---|---|---|---|
| 421 bits(1082) | 2e-153 | Compositional matrix adjust. | 213/325(66%) | 250/325(76%) | 23/325(7%) |

```
Mouse  1    MWPLAAALLLGSCCCGSAQLLFSNVNSIEFTSCNETVVIPCIVRNVEAQSTEEMFVKWKL  60
            MWPL AALLLGS CCGSAQLLF+   S+EFT CN+TVVIPC V N+EAQ+T E++VKWK
Human  1    MWPLVAALLLGSACCGSAQLLFNKTKSVEFTFCNDTVVIPCFVTNMEAQNTTEVYVKWKF  60

Mouse  61   NKSYIFIYDGNKNSTTTDQNFTSAKISVSDLINGIASLKMDKRDAM--VGNYTCEVTELS  118
                I+ +DG  N +T   +F+SAKI VS L+ G ASLKMDK DA+   GNYTCEVTEL+
Human  61   KGRDIYTFDGALNKSTVPTDFSSAKIEVSQLLKGDASLKMDKSDAVSHTGNYTCEVTELT  120

Mouse  119  REGKTVIELKNRTAFNTDQGSACSYEEEKGGCKLVSWFSPNEKILIVIFPILAILLFWGK  178
            REG+T+IELK R                     +VSWFSPNE ILIVIFPI AILLFWG+
Human  121  REGETIIELKYR---------------------VVSWFSPNENILIVIFPIFAILLFWGQ  159

Mouse  179  FGILTLKYKSSHTNKRIILLLVAGLVLTVIVVVGAILLIPGEKPVKNASGLGLIVISTGI  238
            FGI TLKY+S   +++ I LLVAGLV+TVIV+VGAIL +PGE  +KNA+GLGLIV STGI
Human  160  FGIKTLKYRSGGMDEKTIALLVAGLVITVIVIVGAILFVPGEYSLKNATGLGLIVTSTGI  219

Mouse  239  LILLQYNVFMTAFGMTSFTIAILITQVLGYVLALVGLCLCIMACEPVHGPLLISGLGIIA  298
            LILL Y VF TA G+TSF IAIL+ QV+ Y+LA+VGL LCI AC P+HGPLLISGL I+A
Human  220  LILLHYYVFSTAIGLTSFVIAILVIQVIAYILAVVGLSLCIAACIPMHGPLLISGLSILA  279

Mouse  299  LAELLGLVYMKFVASNQRTIQPPRN  323
            LA+LLGLVYMKFVASNQ+TIQPPR
Human  280  LAQLLGLVYMKFVASNQKTIQPPRK  304
```

GENETICALLY MODIFIED NON-HUMAN ANIMAL WITH HUMAN OR CHIMERIC SIRPA

CLAIM OF PRIORITY

This application is a continuation of and claims priority to international Application No. PCT/CN2018/081629, filed on Apr. 2, 2018, which claims the benefit of Chinese Patent Application App. No. 201710953316.6, filed on Oct. 13, 2017, Chinese Patent Application App. No. 201711038308.5, filed on Oct. 27, 2017, Chinese Patent Application App. No. 201710205646.7, filed on Mar. 31, 2017, Chinese Patent Application App. No. 201711039543.4, filed on Oct. 27, 2017, Chinese Patent Application No. 201810295709.7, filed on Mar. 30, 2018, and Chinese Patent Application No. 201810296193.8, filed on Mar. 30, 2018. The entire contents of the foregoing are incorporated herein by reference.

TECHNICAL FIELD

This disclosure relates to genetically modified animal expressing human or chimeric (e.g., humanized) SIRPα, and methods of use thereof.

BACKGROUND

The immune system has developed multiple mechanisms to prevent deleterious activation of T cells. One such mechanism is the intricate balance between positive and negative costimulatory signals delivered to T cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, thus the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human SIRPα or chimeric SIRPα. The animal model can express human SIRPα or chimeric SIRPα (e.g., humanized SIRPα) protein in its body. It can be used in the studies on the function of SIRPα gene, and can be used in the screening and evaluation of anti-human SIRPα and anti-CD47 antibodies. In addition, the animal models prepared by the methods described herein can be used in drug screening, pharmacodynamics studies, treatments for immune-related diseases (e.g., autoimmune disease), and cancer therapy for human SIRPα target sites; they can also be used to facilitate the development and design of new drugs, and save time and cost. In summary, this disclosure provides a powerful tool for studying the function of SIRPα protein and a platform for screening cancer drugs.

In one aspect, the disclosure provides a genetically-modified, non-human animal whose genome comprises at least one chromosome comprising a sequence encoding a human or chimeric SIRPα.

In some embodiments, the sequence encoding the human or chimeric SIRPα is operably linked to an endogenous regulatory element at the endogenous SIRPα gene locus in the at least one chromosome.

In some embodiments, the sequence encoding a human or chimeric SIRPα comprises a sequence encoding an amino acid sequence that is at least 50%, 55%, 65%, 70%, 75%, 80%, 85%, 90%, 95%, 99%, or 100% identical to human SIRPα (SEQ ID NO: 4).

In some embodiments, the sequence encoding a human or chimeric SIRPα comprises a sequence encoding an amino acid sequence that is at least 50%, 55%, 65%, 70%, 75%, 80%, 85%, 90%, 95%, 99%, or 100% identical to SEQ ID NO: 8, 25, 26, 27 or 28.

In some embodiments, the sequence encoding a human or chimeric SIRPα comprises a sequence that is at least 50%, 55%, 65%, 70%, 75%, 80%, 85%, 90%, 95%, 99%, or 100% identical to amino acids 31-138 of SEQ ID NO: 4.

In some embodiments, the animal is a mammal, e.g., a monkey, a rodent or a mouse. In some embodiments, the animal is a BALB/c mouse or a C57BL/6 mouse.

In some embodiments, the animal does not express endogenous SIRPα. In some embodiments, the animal has one or more cells expressing human or chimeric SIRPα.

In some embodiments, the animal has one or more cells expressing human or chimeric SIRPα, and the expressed human or chimeric SIRPα can bind to CD47 (e.g., human or endogenous CD47). In some embodiments, the animal has one or more cells expressing human or chimeric SIRPα, and the expressed human or chimeric SIRPα cannot bind to CD47 (e.g., human or endogenous CD47).

In another aspect, the disclosure is related to a genetically-modified, non-human animal, wherein the genome of the animal comprises a replacement of a sequence encoding a region of endogenous SIRPα with a sequence encoding a corresponding region of human SIRPα at an endogenous SIRPα gene locus.

In some embodiments, the sequence encoding the corresponding region of human SIRPα is operably linked to an endogenous regulatory element at the endogenous SIRPα locus, and one or more cells of the animal expresses a chimeric SIRPα.

In some embodiments, the animal does not express endogenous SIRPα. In some embodiments, the replaced locus is the extracellular region of SIRPα.

In some embodiments, the animal has one or more cells expressing a chimeric SIRPα having an extracellular region, wherein the extracellular region comprises a sequence that is at least 50%, 60%, 70%, 80%, 90%, 95%, or 99% identical to the extracellular region of human SIRPα.

In some embodiments, the extracellular region of the chimeric SIRPα has a sequence that has at least 10, 20, 30, 40, 50, 60, 70, 80, 90, 100, 200, 300, 400, 500, 600, 700, 800, 900, or 1000 contiguous amino acids that are identical to a contiguous sequence present in the extracellular region of human SIRPα.

In some embodiments, the animal is a mouse, and the replaced endogenous SIRPα locus is exon 1, exon 2, exon 3, exon 4, exon 5, exon 6, exon 7, and/or exon 8 of the endogenous mouse SIRPα gene.

In some embodiments, the animal is heterozygous with respect to the replacement at the endogenous SIRPα gene locus. In some embodiments, the animal is homozygous with respect to the replacement at the endogenous SIRPα gene locus.

In another aspect, the disclosure is related to methods for making a genetically-modified, non-human animal. The methods involve replacing in at least one cell of the animal, at an endogenous SIRPα gene locus, a sequence encoding a region of an endogenous SIRPα with a sequence encoding a corresponding region of human SIRPα.

In some embodiments, the sequence encoding the corresponding region of human SIRPα comprises exon 3 of a human SIRPα gene.

In some embodiments, the sequence encoding the corresponding region of SIRPα comprises at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nucleotides of exon 3 of a human SIRPα gene.

In some embodiments, the sequence encoding the corresponding region of human SIRPα encodes a sequence that is at least 90% identical to amino acids 31-138 of SEQ ID NO: 4.

In some embodiments, the locus is located within the extracellular region of SIRPα.

In some embodiments, the animal is a mouse, and the locus is exon 1, exon 2, exon 3, exon 4, exon 5, exon 6, exon 7, and/or exon 8 of the mouse SIRPα gene (e.g., exon 2).

In another aspect, the disclosure is also related to a non-human animal comprising at least one cell comprising a nucleotide sequence encoding a chimeric SIRPα polypeptide, wherein the chimeric SIRPα polypeptide comprises at least 10, 20, 30, 40, 50, 60, 70, 80, 90, or 100 contiguous amino acid residues that are identical to the corresponding contiguous amino acid sequence of a human SIRPα, wherein the animal expresses the chimeric SIRPα.

In some embodiments, the chimeric SIRPα polypeptide has at least 10, 20, 30, 40, 50, 60, 70, 80, 90, or 100 contiguous amino acid residues that are identical to the corresponding contiguous amino acid sequence of a human SIRPα extracellular region.

In some embodiments, the chimeric SIRPα polypeptide comprises a sequence that is at least 90%, 95%, or 99% identical to amino acids 31-138 of SEQ ID NO: 4.

In some embodiments, the nucleotide sequence is operably linked to an endogenous SIRPα regulatory element of the animal.

In some embodiments, the chimeric SIRPα polypeptide comprises an endogenous SIRPα transmembrane region and/or a cytoplasmic region.

In some embodiments, the nucleotide sequence is integrated to an endogenous SIRPα gene locus of the animal.

In some embodiments, the chimeric SIRPα has at least one mouse SIRPα activity and/or at least one human SIRPα activity.

In another aspect, the disclosure is also related to methods of making a genetically-modified mouse cell that expresses a chimeric SIRPα. The methods involve replacing, at an endogenous mouse SIRPα gene locus, a nucleotide sequence encoding a region of mouse SIRPα with a nucleotide sequence encoding a corresponding region of human SIRPα, thereby generating a genetically-modified mouse cell that includes a nucleotide sequence that encodes the chimeric SIRPα, wherein the mouse cell expresses the chimeric SIRPα.

In some embodiments, the chimeric SIRPα comprises: an extracellular region of human SIRPα; a transmembrane region of mouse SIRPα; and/or a cytoplasmic region of mouse SIRPα.

In some embodiments, the nucleotide sequence encoding the chimeric SIRPα is operably linked to an endogenous SIRPα regulatory region, e.g., promoter.

In some embodiments, the animal further comprises a sequence encoding an additional human or chimeric protein (e.g., CD47, programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), CD137, or TNF Receptor Superfamily Member 4 (OX40)).

In some embodiments, the additional human or chimeric protein is CD47 and/or PD-1.

In one aspect, the disclosure also provides methods of determining effectiveness of a SIRPα antagonist (e.g., an anti-SIRPα antibody) for the treatment of cancer. The methods involve administering the SIRPα antagonist to the animal described herein, wherein the animal has a tumor; and determining the inhibitory effects of the SIRPα antagonist to the tumor.

In some embodiments, the animal comprises one or more cells that express CD47.

In some embodiments, the tumor comprises one or more cells that express CD47.

In some embodiments, the tumor comprises one or more cancer cells that are injected into the animal.

In some embodiments, determining the inhibitory effects of the SIRPα antagonist (e.g., an anti-SIRPα antibody) to the tumor involves measuring the tumor volume in the animal.

In some embodiments, the tumor cells are melanoma cells, non-small cell lung carcinoma (NSCLC) cells, small cell lung cancer (SCLC) cells, non-Hodgkin lymphoma cells, bladder cancer cells, prostate cancer cells, breast cancer cells, ovarian cancer cells, colorectal cancer cells, and/or refractory solid tumor cells.

In another aspect, the disclosure also provides methods of determining effectiveness of a SIRPα antagonist (e.g., an anti-SIRPα antibody) and an additional therapeutic agent for the treatment of a tumor. The methods involve administering the SIRPα antagonist and the additional therapeutic agent to the animal as described herein, wherein the animal has a tumor; and determining the inhibitory effects on the tumor.

In some embodiments, the animal further comprises a sequence encoding a human or chimeric CD47.

In some embodiments, the additional therapeutic agent is an anti-CD47 antibody.

In some embodiments the additional therapeutic agent is an anti-PD-1 antibody, an anti-PD-L1 antibody, an anti-CTLA4 antibody, an anti-CD20 antibody, an anti-EGFR antibody, or an anti-CD319 antibody.

In some embodiments, the tumor comprises one or more tumor cells that express SIRPα.

In some embodiments, the tumor is caused by injection of one or more cancer cells into the animal.

In some embodiments, determining the inhibitory effects of the treatment involves measuring the tumor volume in the animal.

In some embodiments the tumor comprises melanoma cells, non-small cell lung carcinoma (NSCLC) cells, small cell lung cancer (SCLC) cells, non-Hodgkin lymphoma cells, bladder cancer cells, prostate cancer cells, breast cancer cells, ovarian cancer cells, colorectal cancer cells, and/or refractory solid tumor cells.

In another aspect, the disclosure further provides methods of determining toxicity of an agent (e.g., a SIRPα antagonist). The methods involve administering the agent to the animal as described herein; and determining weight change of the animal. In some embodiments, the method further involve performing a blood test (e.g., determining red blood cell count).

In one aspect, the disclosure relates to proteins comprising an amino acid sequence, wherein the amino acid sequence is one of the following:

(a) an amino acid sequence set forth in SEQ ID NO: 8, 25, 26, 27 or 28;
(b) an amino acid sequence that is at least 90%, 91%, 92%, 93%, 94%, 95%, 96%, 97%, 98%, or 99% identical to SEQ ID NO: 8, 25, 26, 27 or 28;
(c) an amino acid sequence that is different from the amino acid sequence set forth in SEQ ID NO: 8, 25, 26, 27 or 28 by no more than 10, 9, 8, 7, 6, 5, 4, 3, 2 or 1 amino acid; and
(d) an amino acid sequence that comprises a substitution, a deletion and/or insertion of one, two, three, four, five or more amino acids to the amino acid sequence set forth in SEQ ID NO: 8, 25, 26, 27 or 28.

In some embodiments, provided herein are cells comprising the proteins disclosed herein. In some embodiments, provided herein are animals having the proteins disclosed herein.

In another aspect, the disclosure relates to nucleic acids comprising a nucleotide sequence, wherein the nucleotide sequence is one of the following:

(a) a sequence that encodes the protein as described herein;
(b) SEQ ID NO: 5, 6, 7, 17, 18, 19, 20, 21, 22, 23, or 24;
(c) a sequence that is at least 90%, 91%, 92%, 93%, 94%, 95%, 96%, 97%, 98%, or 99% identical to SEQ ID NO: 5, 6, 7, 17, 18, 19, 20, 21, 22, 23, or 24.

In some embodiments, provided herein are cells comprising the nucleic acids disclosed herein. In some embodiments, provided herein are animals having the nucleic acids disclosed herein.

In another aspect, the disclosure also provides a genetically-modified, non-human animal whose genome comprise a disruption in the animal's endogenous SIRPα gene, wherein the disruption of the endogenous SIRPα gene comprises deletion of exon 2 or part thereof of the endogenous SIRPα gene.

In some embodiments, the disruption of the endogenous SIRPα gene further comprises deletion of one or more exons or part of exons selected from the group consisting of exon 1, exon 3, exon 4, exon 5, exon 6, exon 7, and/or exon 8 of the endogenous SIRPα gene.

In some embodiments, the disruption of the endogenous SIRPα gene further comprises deletion of one or more introns or part of introns selected from the group consisting of intron 1, intron 2, intron 3, intron 4, intron 5, intron 6, and intron 7 of the endogenous SIRPα gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous SIRPα gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, exon 5, exon 6, exon 7, and/or exon 8 (e.g., deletion of at least 300 nucleotides of exon 2).

In some embodiments, the mice described in the present disclosure can be mated with the mice containing other human or chimeric genes (e.g., chimeric CD47, chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In one aspect, the disclosure relates to a targeting vector, including a) a DNA fragment homologous to the 5' end of a region to be altered (5' arm), which is selected from the SIRPα gene genomic DNAs in the length of 100 to 10,000 nucleotides; b) a desired/donor DNA sequence encoding a donor region; and c) a second DNA fragment homologous to the 3' end of the region to be altered (3' arm), which is selected from the SIRPα gene genomic DNAs in the length of 100 to 10,000 nucleotides.

In some embodiments, a) the DNA fragment homologous to the 5' end of a region to be altered (5' arm) is selected from the nucleotide sequences that have at least 90% homology to the NCBI accession number NC_000068.7; c) the DNA fragment homologous to the 3' end of the region to be altered (3' arm) is selected from the nucleotide sequences that have at least 90% homology to the NCBI accession number NC_000068.7.

In some embodiments, a) the DNA fragment homologous to the 5' end of a region to be altered (5' arm) is selected from the nucleotides from the position 129607346 to the position 129608914 of the NCBI accession number NC_000068.7; c) the DNA fragment homologous to the 3' end of the region to be altered (3' arm) is selected from the nucleotides from the position 129609239 to the position 129610638 of the NCBI accession number NC_000068.7.

In some embodiments, a length of the selected genomic nucleotide sequence is about 3 kb, 3.5 kb, 4 kb, 4.5 kb, or 5 kb. In some embodiments, the region to be altered is exon 1, exon 2, exon 3, exon 4, exon 5, exon 6, exon 7, and/or exon 8 of mouse SIRPα gene.

In some embodiments, the sequence of the 5' arm is shown in SEQ ID NO: 29. In some embodiments, the sequence of the 3' arm is shown in SEQ ID NO: 30.

In some embodiments, the targeting vector further includes a selectable gene marker.

In some embodiments, the target region is derived from human. In some embodiments, the target region is a part or entirety of the nucleotide sequence of a humanized SIRPα. In some embodiments, the nucleotide sequence is shown as one or more of exon 1, exon 2, exon 3, exon 4, exon 5, exon 6, exon 7, exon 8, and exon 9 of the human SIRPα.

In some embodiments, the nucleotide sequence of the human SIRPα encodes the human SIRPα protein with the NCBI accession number NP_542970.1 (SEQ ID NO: 4). In some emboldens, the nucleotide sequence of the human SIRPα is selected from the nucleotides from the position 1915110 to the position 1915433 of NC_000020.11 (SEQ ID NO: 31).

The disclosure also relates to a cell including the targeting vector as described herein.

The disclosure also relates to a method for establishing a genetically-modified non-human animal expressing two human or chimeric (e.g., humanized) genes. The method includes the steps of (a) using the method for establishing a SIRPα gene humanized animal model to obtain a SIRPα gene genetically modified humanized mouse;

(b) mating the SIRPα gene genetically modified humanized mouse obtained in step (a) with another humanized mouse, and then screening to obtain a double humanized mouse model.

In some embodiments, in step (b), the SIRPα gene genetically modified humanized mouse obtained in step (a) is mated with a CD47 humanized mouse to obtain a SIRPα and CD47 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized SIRPα gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a SIRPα amino acid sequence of a humanized mouse, wherein the amino acid sequence is selected from the group consisting of:

a) an amino acid sequence shown in SEQ ID NO: 8, 25, 26, 27 or 28;
b) an amino acid sequence having a homology of at least 90% with the amino acid sequence shown in SEQ ID NO: 8, 25, 26, 27 or 28;
c) an amino acid sequence encoded by a nucleic acid sequence, wherein the nucleic acid sequence is able to hybridize to a nucleotide sequence encoding the amino acid shown in SEQ ID NO: 8, 25, 26, 27 or 28 under a low stringency condition or a strict stringency condition;
d) an amino acid sequence having a homology of at least 90%, 91%, 92%, 93%, 94%, 95%, 96%, 97%, 98%, or at least 99% with the amino acid sequence shown in SEQ ID NO: 8, 25, 26, 27 or 28;
e) an amino acid sequence that is different from the amino acid sequence shown in SEQ ID NO: 8, 25, 26, 27 or 28 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 8, 25, 26, 27 or 28.

The disclosure also relates to a SIRPα nucleic acid sequence of a humanized mouse, wherein the nucleic acid sequence is selected from the group consisting of:

a) a nucleic acid sequence that encodes the SIRPα amino acid sequence of a humanized mouse;
b) a nucleic acid sequence that is set forth in SEQ ID NO: 5;
c) a nucleic acid sequence having a coding DNA sequence (CDS) as shown in SEQ ID NO: 6, 7, 17, 18, 19, 20, 21, 22, 23, or 24;
d) a nucleic acid sequence that can hybridize to the nucleotide sequence as shown in SEQ ID NO: 5, 6, 7, 17, 18, 19, 20, 21, 22, 23, or 24 under a low stringency condition or a strict stringency condition;
e) a nucleic acid sequence that has a homology of at least 90%, 91%, 92%, 93%, 94%, 95%, 96%, 97%, 98%, or at least 99% with the nucleotide sequence as shown in SEQ ID NO: 5, 6, 7, 17, 18, 19, 20, 21, 22, 23, or 24;
f) a nucleic acid sequence that encodes an amino acid sequence, wherein the amino acid sequence has a homology of at least 90% with the amino acid sequence shown in SEQ ID NO: 8, 25, 26, 27 or 28;
g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 8, 25, 26, 27 or 28;
h) a nucleic acid sequence that encodes an amino acid sequence, wherein the amino acid sequence is different from the amino acid sequence shown in SEQ ID NO: 8, 25, 26, 27 or 28 by no more than 10, 9, 8, 7, 6, 5, 4, 3, 2 or no more than 1 amino acid; and/or
i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 8, 25, 26, 27 or 28.

The disclosure further relates to a SIRPα genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the SIRPα gene function, human SIRPα antibodies, the drugs or efficacies for human SIRPα targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 12 shows PCR results from F1 generation SIRPα knockout mice (M is Marker. WT indicates wildtype. + is positive control). Results show that mice numbered F1-KO-1, F1-KO-2, F1-KO-3, F1-KO-4, F1-KO-5, F1-KO-6 are heterozygous SIRPα knockout mice (F1 generation).

FIG. 25 shows the alignment between mouse SIRPα amino acid sequence (NP_031573.2; SEQ ID NO: 2) and human SIRPα amino acid sequence (NP_542970.1; SEQ ID NO: 4).

FIG. 26 shows the alignment between mouse CD47 amino acid sequence (NP_034711.1; SEQ ID NO: 94) and human CD47 amino acid sequence (NP_001768.1; SEQ ID NO: 92).

DETAILED DESCRIPTION

Figure 1:
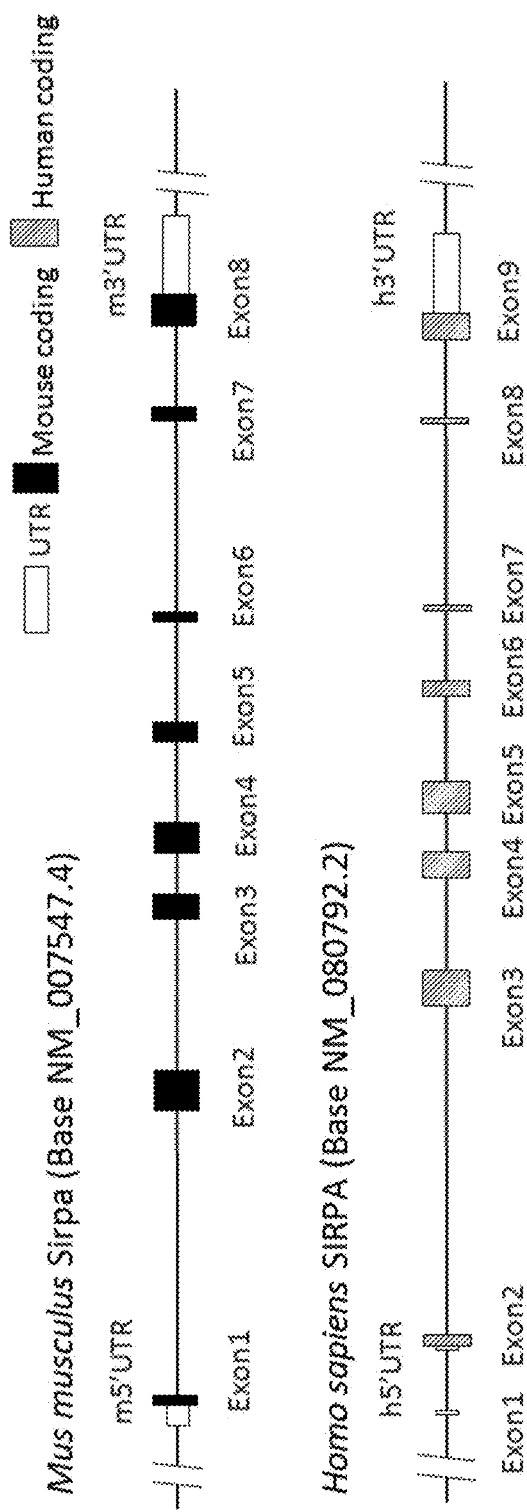
FIG. 1 is a schematic diagram showing human and mouse SIRPα genes.

This disclosure relates to transgenic non-human animal with human or chimeric (e.g., humanized) SIRPα, and methods of use thereof.

Signal regulatory protein α (SIRPα) is a regulatory membrane glycoprotein from SIRP family. It is mainly expressed by myeloid cells and also by stem cells or neurons. SIRPα acts as inhibitory receptor and interacts with a broadly expressed transmembrane protein CD47. This interaction negatively controls effector function of innate immune cells such as host cell phagocytosis. SIRPα diffuses laterally on the macrophage membrane and accumulates at a phagocytic synapse to bind CD47, which inhibits the cytoskeleton-intensive process of phagocytosis by the macrophage.

CD47 provides a "do not eat" signal by binding to the N-terminus of signal regulatory protein alpha (SIRPα). It has been found to be overexpressed in many different tumor cells. Thus, targeting CD47 and/or SIRPα is in the spotlight of cancer immunotherapy. Blocking CD47 or SIRPα triggers the recognition and elimination of cancer cells by the innate immunity. These antibodies or binding agents that target CD47 or SIRPα can be used to treat various tumors and cancers, e.g., solid tumors, hematologic malignancies (e.g., relapsed or refractory hematologic malignancies), acute myeloid leukemia, non-Hodgkin's lymphoma, breast cancer, bladder cancer, ovarian cancer, and small cell lung cancer tumors. The anti-CD47 or anti-SIRPα antibodies are described, e.g., in Huang et al. "Targeting CD47: the achievements and concerns of current studies on cancer immunotherapy." Journal of thoracic disease 9.2 (2017): E168; Liu et al. "Pre-clinical development of a humanized anti-CD47 antibody with anti-cancer therapeutic potential." PloS one 10.9 (2015): e0137345; Ansell et al. "A phase 1 study of TTI-621, a novel immune checkpoint inhibitor targeting CD47, in patients with relapsed or refractory hematologic malignancies." (2016): 1812-1812; Yanagita et al. "Anti-SIRPα antibodies as a potential new tool for cancer immunotherapy." JCI insight 2.1 (2017); each of which is incorporated herein by reference in its entirety.

Experimental animal models are an indispensable research tool for studying the effects of these antibodies. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels. Furthermore, because of interaction between human SIRPα and human CD47, a desirable animal model for the investigation of anti-SIRPα or anti-CD47 antibodies should faithfully mimic the interaction between human SIRPα and human CD47, elicit robust responses from both the innate and adaptive immunity, and recapitulate side effects of CD47 blockade on RBCs and platelets (Huang et al. "Targeting CD47: the achievements and concerns of current studies on cancer immunotherapy." Journal of thoracic disease 9.2 (2017): E168).

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames& S. J. Higginseds. 1984); Transcription And Translation (B. D. Hames& S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N. Y., 1986); each of which is incorporated herein by reference in its entirety.

Signal regulatory protein α

Signal regulatory protein α (SIRPα, SIRPα, Sirpa, or CD172A) is a transmembrane protein. It has an extracellular region comprising three Ig-like domains and a cytoplasmic region containing immunoreceptor tyrosine-based inhibition motifs that mediate binding of the protein tyrosine phosphatases SHP1 and SHP2. Tyrosine phosphorylation of SIRPα is regulated by various growth factors and cytokines as well as by integrin-mediated cell adhesion to extracellular matrix proteins. SIRPα is especially abundant in myeloid cells such as macrophages and dendritic cells, whereas it is expressed at only low levels in T, B, NK, and NKT cells.

The extracellular region of SIRPα can interact with its ligand CD47. The interaction of SIRPα on macrophages with CD47 on red blood cells prevents phagocytosis of Ig-opsonized red blood cells by macrophages in vitro and in vivo. The ligation of SIRPα on phagocytes by CD47 expressed on a neighboring cell results in phosphorylation of SIRPα cytoplasmic immunoreceptor tyrosine-based inhibition (ITIM) motifs, leading to the recruitment of SHP-1 and SHP-2 phosphatases. One resulting downstream effect is the prevention of myosin-IIA accumulation at the phagocytic synapse and consequently inhibition of phagocytosis. Thus, CD47-SIRPα interaction functions as a negative immune checkpoint to send a "don't eat me" signal to ensure that healthy autologous cells are not inappropriately phagocytosed. However, overexpression of CD47 has also been found in nearly all types of tumors, some of which include acute myeloid leukemia, non-Hodgkin's lymphoma, bladder cancer, and breast cancer. Such negative regulation of macrophages can be minimized by blocking the binding of CD47 to SIRPα. Thus, antibodies against CD47 or SIRPα can promote both Ab-dependent cellular phagocytosis (ADCP) and in some cases, trigger Ab-dependent cellular cytotoxicity (ADCC), thus can be used to treat various cancers.

A detailed description of SIRPα and its function can be found, e.g., in Yanagita et al. "Anti-SIRPα antibodies as a potential new tool for cancer immunotherapy." JCI insight 2.1 (2017); Seiffert et al. "Signal-regulatory protein α (SIRPα) but not SIRPβ is involved in T-cell activation, binds to CD47 with high affinity, and is expressed on immature CD34+CD38-hematopoietic cells." Blood 97.9 (2001): 2741-2749; which are incorporated by reference herein in the entirety.

In human genomes, SIRPα gene (Gene ID: 140885) locus has 9 exons, exon 1, exon 2, exon 3, exon 4, exon 5, exon 6, exon 7, exon 8, and exon 9. The SIRPα protein has an extracellular region, a transmembrane region, and a cytoplasmic region. The signal peptide is located at the extracellular region. The nucleotide sequence for human SIRPα mRNA is NM_080792.2 (SEQ ID NO: 3), and the amino acid sequence for human SIRPα is NP_542970.1 (SEQ ID NO: 4). The location for each exon and each region in human SIRPα nucleotide sequence and amino acid sequence is listed below:

TABLE 1

| Human SIRPα (approximate location) | NM_080792.2 3868 bp (SEQ ID NO: 3) | NP_542970.1 504 aa (SEQ ID NO: 4) |
|---|---|---|
| Exon 1 | 1-18 | Non-coding range |
| Exon 2 | 19-106 | 1-26 |
| Exon 3 | 107-463 | 27-145 |
| Exon 4 | 464-781 | 146-251 |
| Exon 5 | 782-1114 | 252-362 |
| Exon 6 | 1115-1228 | 363-400 |
| Exon 7 | 1229-1253 | 401-409 |
| Exon 8 | 1254-1293 | 410-422 |
| Exon 9 | 1294-3868 | 423-504 |
| Signal peptide | 28-117 | 1-30 |
| Extracellular region (excluding signal peptide region) | 118-1146 | 31-373 |
| Transmembrane region | 1147-1209 | 374-394 |
| Cytoplasmic region | 1210-1539 | 395-504 |
| Donor in one example | 118-441 | 31-138 |

Human SIRPα also have several transcript variants. These variants can also be used to make humanized animals, and they are summarized below.

TABLE 2

| Human SIRPα transcript variants | Amino acid sequences |
|---|---|
| NM_001040022.1 | NP_001035111.1 |
| NM_001040023.1 | NP_001035112.1 |
| NM_001330728.1 | NP_001317657.1 |
| XM_005260670.3 | XP_005260727.1 |
| XM_006723545.3 | XP_006723608.1 |
| XM_011529173.2 | XP_011527475.1 |

In mice, SIRPα gene locus has 8 exons, exon 1, exon 2, exon 3, exon 4, exon 5, exon 6, exon 7, and exon 8 (FIG. 1). The mouse SIRPα protein also has an extracellular region, a transmembrane region, and a cytoplasmic region, and the signal peptide is located at the extracellular region. The nucleotide sequence for mouse SIRPα cDNA is NM_007547.4 (SEQ ID NO: 1), the amino acid sequence for mouse SIRPα is NP_031573.2 (SEQ ID NO: 2). The location for each exon and each region in the mouse SIRPα nucleotide sequence and amino acid sequence is listed below:

TABLE 3

| Mouse SIRPα (approximate location) | NM_007547.4 4031 bp (SEQ ID NO: 1) | NP_031573.2 509aa (SEQ ID NO: 2) |
|---|---|---|
| Exon 1 | 1-526 | 1-27 |
| Exon 2 | 527-883 | 28-146 |
| Exon 3 | 884-1201 | 147-252 |
| Exon 4 | 1202-1537 | 253-364 |
| Exon 5 | 1538-1651 | 365-402 |
| Exon 6 | 1652-1676 | 403-411 |
| Exon 7 | 1677-1716 | 412-424 |
| Exon 8 | 1717-4018 | 425-509 |
| Signal peptide | 445-537 | 1-31 |
| Extracellular region (excluding signal peptide region) | 538-1557 | 32-371 |
| Transmembrane region | 1558-1632 | 372-396 |
| Cytoplasmic region | 1633-1971 | 397-509 |
| Replaced region in one example | 538-861 | 32-139 |

The mouse SIRPα gene (Gene ID: 19261) is located in Chromosome 2 of the mouse genome, which is located from 129592665 to 129632228, of NC_000068.7 (GRCm38.p4 (GCF_000001635.24)). The 5'-UTR is from 129,593,205 to 129,593,612, exon 1 is from 129,593,205 to 129,593,694, the first intron is from 129,593,695 to 129,608,903, exon 2 is from 129,608,904 to 129,609,260, the second intron is from 129,609,261 to 129,615,446, exon 3 is from 129,615,447 to 129,615,764, the third intron is from 129,615,765 to 129,616,222, exon 4 is from 129,616,223 to 129,616,558, the fourth intron is from 129,616,559 to 129,618,456, exon 5 is from 129,618,457 to 129,618,570, the fifth intron is from 129,618,571 to 129,621,202, exon 6 is from 129,621,203 to 129,621,227, the sixth intron is from 129,621,228 to 129,627,945, exon 7 is from 129,627,946 to 129,627,985, the seventh intron is from 129,627,986 to 129,629,926, exon 8 is from 129,629,927 to 129,632,228, the 3'-UTR is from 129,630,185 to 129,632,228, base on transcript NM_007547.4.

Thus, exon 1 in mouse SIRPα roughly corresponds to exon 2 in human SIRPα, exon 2 in mouse SIRPα roughly corresponds to exon 3 in human SIRPα, exon 3 in mouse SIRPα roughly corresponds to exon 4 in human SIRPα, exon 4 in mouse SIRPα roughly corresponds to exon 5 in human SIRPα, exon 5 in mouse SIRPα roughly corresponds to exon 6 in human SIRPα, exon 6 in mouse SIRPα roughly corresponds to exon 7 in human SIRPα, exon 7 in mouse SIRPα roughly corresponds to exon 8 in human SIRPα, and exon 8 in mouse SIRPα roughly corresponds to exon 9 in human SIRPα.

All relevant information for mouse SIRPα locus can be found in the NCBI website with Gene ID: 19261, which is incorporated by reference herein in its entirety.

The mouse SIRPα has several transcript variants. A portion of these sequences can also be replaced by corresponding human sequences. These variants are summarized in Table 4.

TABLE 4

| Mouse SIRPα transcript variants | Amino acid sequences |
|---|---|
| NM_001177647.2 (SEQ ID NO: 9) | NP_001171118.1 (SEQ ID NO: 10) |
| NM_001291019.1 (SEQ ID NO: 11) | NP_001277948.1 (SEQ ID NO: 12) |
| NM_001291020.1 (SEQ ID NO: 13) | NP_001277949.1 (SEQ ID NO: 14) |
| NM_001291021.1 (SEQ ID NO: 15) | NP_001277950.1 (SEQ ID NO: 16) |

FIG. 25 shows the alignment between mouse SIRPα amino acid sequence (NP_031573.2; SEQ ID NO: 2) and human SIRPα amino acid sequence (NP_542970.1; SEQ ID NO: 4). Thus, the corresponding amino acid residue or region between human and mouse SIRPα can also be found in FIG. 25.

SIRPα genes, proteins, and locus of the other species are also known in the art. For example, the gene ID for SIRPα in *Rattus norvegicus* is 25528, the gene ID for SIRPα in *Macaca mulatta* (Rhesus monkey) is 717811, the gene ID for SIRPα in *Canis lupus familiaris* (dog) is 609452, and the gene ID for SIRPα in *Sus scrofa* (pig) is 494566. The relevant information for these genes (e.g., intron sequences, exon sequences, amino acid residues of these proteins) can be found, e.g., in NCBI database.

The present disclosure provides human or chimeric (e.g., humanized) SIRPα nucleotide sequence and/or amino acid sequences. In some embodiments, the entire sequence of mouse exon 1, exon 2, exon 3, exon 4, exon 5, exon 6, exon 7, exon 8, the signal peptide, the extracellular region, the transmembrane region, and/or the cytoplasmic region are replaced by the corresponding human sequence.

In some embodiments, a "region" or "portion" of mouse exon 1, exon 2, exon 3, exon 4, exon 5, exon 6, exon 7, exon 8, signal peptide, the extracellular region, the transmembrane region, and/or the cytoplasmic region is replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues.

In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, exon 9, signal peptide, the extracellular region, the transmembrane region, and/or the cytoplasmic region. In some embodiments, a region, a portion, or the entire sequence of mouse exon 2 is replaced by a region, a portion, or the entire sequence of human exon 3.

In some embodiments, a "region" or "portion" of mouse exon 1, exon 2, exon 3, exon 4, exon 5, exon 6, exon 7, exon 8, signal peptide, the extracellular region, the transmembrane region, and/or the cytoplasmic region is deleted.

Thus, in some embodiments, the present disclosure also provides a chimeric (e.g., humanized) SIRPα nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse SIRPα mRNA sequence (e.g., SEQ ID NO: 1), mouse SIRPα amino acid sequence (e.g., SEQ ID NO: 2), or a portion thereof (e.g., exon 1, exon 2, exon 3, exon 4, exon 5, exon 6, exon 7, or exon 8); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human SIRPα mRNA sequence (e.g., SEQ ID NO: 3), human SIRPα amino acid sequence (e.g., SEQ ID NO: 4), or a portion thereof (e.g., exon 1, exon 2, exon 3, exon 4, exon 5, exon 6, exon 7, exon 8, or exon 9).

In some embodiments, the sequence encoding amino acids 32-139 of mouse SIRPα (SEQ ID NO: 2) is replaced. In some embodiments, the sequence is replaced by a sequence encoding a corresponding region of human SIRPα (e.g., amino acids 31-138 of human SIRPα (SEQ ID NO: 4).

In some embodiments, the nucleic acids as described herein are operably linked to a promotor or regulatory element, e.g., an endogenous mouse SIRPα promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse SIRPα nucleotide sequence (e.g., exon 1, exon 2, exon 3, exon 4, exon 5, exon 6, exon 7, exon 8, or SEQ ID NO: 1, 9, 11, 13, or 15).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse SIRPα nucleotide sequence (e.g., exon 1, exon 2, exon 3, exon 4, exon 5, exon 6, exon 7, exon 8, or SEQ ID NO: 1, 9, 11, 13, or 15).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human SIRPα nucleotide sequence (e.g., exon 1, exon 2, exon 3, exon 4, exon 5, exon 6, exon 7, exon 8, exon 9, or SEQ ID NO: 3).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human SIRPα nucleotide sequence (e.g., exon 1, exon 2, exon 3, exon 4, exon 5, exon 6, exon 7, exon 8, exon 9, or SEQ ID NO: 3).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse SIRPα amino acid sequence (e.g., exon 1, exon 2, exon 3, exon 4, exon 5, exon 6, exon 7, exon 8, or SEQ ID NO: 2, 10, 12, 14, or 16).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse SIRPα amino acid sequence (e.g., exon 1, exon 2, exon 3, exon 4, exon 5, exon 6, exon 7, exon 8, or SEQ ID NO: 2, 10, 12, 14, or 16).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human SIRPα amino acid sequence (e.g., exon 1, exon 2, exon 3, exon 4, exon 5, exon 6, exon 7, exon 8, exon 9, or SEQ ID NO: 4).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human SIRPα amino acid sequence (e.g., exon 1, exon 2, exon 3, exon 4, exon 5, exon 6, exon 7, exon 8, exon 9, or SEQ ID NO: 4).

The present disclosure also provides a humanized SIRPα mouse amino acid sequence, wherein the amino acid sequence is selected from the group consisting of:

a) an amino acid sequence shown in SEQ ID NO: 8, 25, 26, 27 or 28;
b) an amino acid sequence having a homology of at least 90% with or at least 90% identical to the amino acid sequence shown in SEQ ID NO: 8, 25, 26, 27 or 28;
c) an amino acid sequence encoded by a nucleic acid sequence, wherein the nucleic acid sequence is able to hybridize to a nucleotide sequence encoding the amino acid shown in SEQ ID NO: 8, 25, 26, 27 or 28 under a low stringency condition or a strict stringency condition;
d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 8, 25, 26, 27 or 28;
e) an amino acid sequence that is different from the amino acid sequence shown in SEQ ID NO: 8, 25, 26, 27 or 28 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 8, 25, 26, 27 or 28.

The present disclosure also relates to a SIRPα nucleic acid (e.g., DNA or RNA) sequence, wherein the nucleic acid sequence can be selected from the group consisting of:

a) a nucleic acid sequence as shown in SEQ ID NO: 6, 7, 17, 18, 19, 20, 21, 22, 23, or 24, or a nucleic acid sequence encoding a homologous SIRPα amino acid sequence of a humanized mouse;
b) a nucleic acid sequence that is shown in SEQ ID NO: 5;
c) a nucleic acid sequence that is able to hybridize to the nucleotide sequence as shown in SEQ ID NO: 5, 6, 7, 17, 18, 19, 20, 21, 22, 23, or 24 under a low stringency condition or a strict stringency condition;
d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 5, 6, 7, 17, 18, 19, 20, 21, 22, 23, or 24;
e) a nucleic acid sequence that encodes an amino acid sequence, wherein the amino acid sequence has a homology of at least 90% with or at least 90% identical to the amino acid sequence shown in SEQ ID NO: 8, 25, 26, 27 or 28;
f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 8, 25, 26, 27 or 28;

g) a nucleic acid sequence that encodes an amino acid sequence, wherein the amino acid sequence is different from the amino acid sequence shown in SEQ ID NO: 8, 25, 26, 27 or 28 by no more than 10, 9, 8, 7, 6, 5, 4, 3, 2 or no more than 1 amino acid; and/or h) a nucleic acid sequence that encodes an amino acid sequence, wherein the amino acid sequence comprises a substitution, a deletion and/or insertion of one or more amino acids to the amino acid sequence shown in SEQ ID NO: 8, 25, 26, 27 or 28.

The present disclosure further relates to a SIRPα genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 5, 6, 7, 17, 18, 19, 20, 21, 22, 23, or 24.

The disclosure also provides an amino acid sequence that has a homology of at least 90% with, or at least 90% identical to the sequence shown in SEQ ID NO: 8, 25, 26, 27 or 28, and has protein activity. In some embodiments, the homology with the sequence shown in SEQ ID NO: 8, 25, 26, 27 or 28 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 8, 25, 26, 27 or 28 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 5, 6, 7, 17, 18, 19, 20, 21, 22, 23, or 24, and encodes a polypeptide that has protein activity. In some embodiments, the homology with the sequence shown in SEQ ID NO: 5, 6, 7, 17, 18, 19, 20, 21, 22, 23, or 24 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 5, 6, 7, 17, 18, 19, 20, 21, 22, 23, or 24 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of identical residues (percent identity) and the percentage of residues conserved with similar physicochemical properties (percent homology), e.g. leucine and isoleucine, can be used to measure sequence similarity. Residues conserved with similar physicochemical properties are well known in the art. The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) SIRPα from an endogenous non-human SIRPα locus.

Genetically Modified Animals

As used herein, the term "genetically-modified non-human animal" refers to a non-human animal having genetic modification (e.g., exogenous DNA) in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the genetic modification in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous SIRPα locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one portion of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized SIRPα gene or a humanized SIRPα nucleic acid. In some embodiments, at least one or more portions of the gene or the nucleic acid is from the human SIRPα gene, at least one or more portions of the gene or the nucleic acid is from a non-human SIRPα gene. In some embodiments, the gene or the nucleic acid comprises a sequence that encodes a SIRPα protein. The encoded SIRPα protein is functional or has at least one activity of the human SIRPα protein or the non-human SIRPα protein, e.g., binding to human or non-human CD47, phosphorylation of its cytoplasmic ITIM motif after binding to CD47, inhibiting phagocytosis, and/or downregulating immune response.

In some embodiments, the chimeric protein or the chimeric polypeptide is a humanized SIRPα protein or a humanized SIRPα polypeptide. In some embodiments, at least one or more portions of the amino acid sequence of the protein or the polypeptide is from a human SIRPα protein, and at least one or more portions of the amino acid sequence of the protein or the polypeptide is from a non-human SIRPα protein. The humanized SIRPα protein or the humanized SIRPα polypeptide is functional or has at least one activity of the human SIRPα protein or the non-human SIRPα protein.

In some embodiments, the humanized SIRPα protein or the humanized SIRPα polypeptide can bind to mouse CD47, inhibit phagocytosis, and/or downregulate immune response. In some embodiments, the humanized SIRPα protein or the humanized SIRPα polypeptide cannot bind to mouse CD47, thus cannot inhibit phagocytosis.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized SIRPα animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human SIRPα locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in U.S.20150106961, which is incorporated herein by reference in its entirety. In some embodiments, the mouse can include a replacement of all or part of mature SIRPα coding sequence with human mature SIRPα coding sequence.

The mouse genetic background can also affect the interaction of CD47 and SIRPα in the mouse. In mice with C57BL/6 background, the mouse SIRPα has a relatively weak binding affinity with humanized or human CD47 protein. In contrast, in mice with BALB/c background, the binding affinity between mouse SIRPα and human (or humanized) CD47 protein is similar to the binding affinity between mouse SIRPα and mouse CD47 protein. Thus, in some embodiments, the humanized CD47 mouse with C57BL/6 background can be used to test the toxicity of anti-hCD47 antibodies. In some embodiments, the humanized CD47 mouse with BALB/c background can be used to test the toxicity of anti-hCD47 antibodies and/or the efficacy of anti-hCD47 antibodies in terms of inhibiting tumor growth. In some embodiments, mice (any background) with both humanized CD47 and humanized SIRPα can be used to test the toxicity of anti-hCD47 antibodies and/or the efficacy of anti-hCD47 antibodies in terms of inhibiting tumor growth.

Genetically modified non-human animals can comprise a modification of an endogenous non-human SIRPα locus. In some embodiments, the modification can comprise a human nucleic acid sequence encoding at least a portion of a mature SIRPα protein (e.g., at least 10%, 20%, 30%, 40%, 50%, 60%, 70%, 80%, 90%, 95%, 96%, 97%, 98%, or 99% identical to the mature SIRPα protein sequence). Although genetically modified cells are also provided that can comprise the modifications described herein (e.g., ES cells, somatic cells), in many embodiments, the genetically modified non-human animals comprise the modification of the endogenous SIRPα locus in the germline of the animal.

Genetically modified animals can express a human SIRPα and/or a chimeric (e.g., humanized) SIRPα from endogenous mouse loci, wherein the endogenous mouse SIRPα gene has been replaced with a human SIRPα gene and/or a nucleotide sequence that encodes a region of human SIRPα sequence or an amino acid sequence that is at least 10%, 20%, 30%, 40%, 50%, 60%, 70&, 80%, 90%, 95%, 96%, 97%, 98%, or 99% identical to the human SIRPα sequence. In various embodiments, an endogenous non-human SIRPα locus is modified in whole or in part to comprise human nucleic acid sequence encoding at least one protein-coding sequence of a mature SIRPα protein.

In some embodiments, the genetically modified mice express the human SIRPα and/or chimeric SIRPα (e.g., humanized SIRPα) from endogenous loci that are under control of mouse promoters and/or mouse regulatory elements. The replacement(s) at the endogenous mouse loci provide non-human animals that express human SIRPα or chimeric SIRPα (e.g., humanized SIRPα) in appropriate cell types and in a manner that does not result in the potential pathologies observed in some other transgenic mice known in the art. The human SIRPα or the chimeric SIRPα (e.g., humanized SIRPα) expressed in animal can maintain one or more functions of the wildtype mouse or human SIRPα in the animal. For example, SIRPα can bind to human or non-human CD47, and downregulate immune response, e.g., downregulate immune response by at least 10%, 20%, 30%, 40%, or 50%. Furthermore, in some embodiments, the animal does not express endogenous SIRPα. As used herein, the term "endogenous SIRPα" refers to SIRPα protein that is expressed from an endogenous SIRPα nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human SIRPα (e.g., SEQ ID NO: 4). In some embodiments, the genome comprises a sequence encoding an amino acid sequence that is at least 70%, 75%, 80%, 85%, 90%, 95%, 99%, or 100% identical to SEQ ID NO: 8, 25, 26, 27 or 28.

The genome of the genetically modified animal can comprise a replacement at an endogenous SIRPα gene locus of a sequence encoding a region of endogenous SIRPα with a sequence encoding a corresponding region of human SIRPα. In some embodiments, the sequence that is replaced is any sequence within the endogenous SIRPα gene locus, e.g., exon 1, exon 2, exon 3, exon 4, exon 5, exon 6, exon 7, exon 8, 5'-UTR, 3'UTR, the first intron, the second intron, and the third intron, the fourth intron, the fifth intron, the sixth intron, or the seventh intron etc. In some embodiments, the sequence that is replaced is within the regulatory region of the endogenous SIRPα gene. In some embodiments, the sequence that is replaced is exon 2 or part thereof, of an endogenous mouse SIRPα gene locus.

The genetically modified animal can have one or more cells expressing a human or chimeric SIRPα (e.g., humanized SIRPα) having an extracellular region and a cytoplasmic region, wherein the extracellular region comprises a sequence that is at least 50%, 60%, 70%, 80%, 90%, 95%, 99% identical to the extracellular region of human SIRPα. In some embodiments, the extracellular region of the humanized SIRPα has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human SIRPα.

Because human SIRPα and non-human SIRPα (e.g., mouse SIRPα) sequences, in many cases, are different, antibodies that bind to human SIRPα will not necessarily have the same binding affinity with non-human SIRPα or have the same effects to non-human SIRPα. Therefore, the genetically modified animal having a human or a humanized extracellular region can be used to better evaluate the effects of anti-human SIRPα antibodies in an animal model. In some embodiments, the genome of the genetically modified animal comprises a sequence encoding an amino acid sequence that corresponds to part or the entire sequence of exon 3 of human SIRPα, part or the entire sequence of the extracellular region of human SIRPα (with or without signal peptide), or part or the entire sequence of amino acids 31-138 of SEQ ID NO: 4.

In some embodiments, the non-human animal can have, at an endogenous SIRPα gene locus, a nucleotide sequence encoding a chimeric human/non-human SIRPα polypeptide, wherein a human portion of the chimeric human/non-human SIRPα polypeptide comprises a portion of human SIRPα extracellular region, and wherein the animal expresses a functional SIRPα on a surface of a cell of the animal. The human portion of the chimeric human/non-human SIRPα polypeptide can comprise a portion of exon 3 of human SIRPα. In some embodiments, the human portion of the chimeric human/non-human SIRPα polypeptide can comprise a sequence that is at least 80%, 85%, 90%, 95%, or 99% identical to amino acids 31-138 of SEQ ID NO: 4.

In some embodiments, the non-human portion of the chimeric human/non-human SIRPα polypeptide comprises the transmembrane region, and/or the cytoplasmic region of an endogenous non-human SIRPα polypeptide. There may be several advantages that are associated with the transmembrane and/or cytoplasmic regions of an endogenous non-human SIRPα polypeptide. For example, once CD47 binds to SIRPα, they can properly transmit extracellular signals into the cells and regulate the downstream pathway. A human or humanized transmembrane and/or cytoplasmic regions may not function properly in non-human animal cells. In some embodiments, a few extracellular amino acids that are close to the transmembrane region of SIRPα are also derived from endogenous sequence.

Furthermore, the genetically modified animal can be heterozygous with respect to the replacement at the endogenous SIRPα locus, or homozygous with respect to the replacement at the endogenous SIRPα locus.

In some embodiments, the humanized SIRPα locus lacks a human SIRPα 5'-UTR. In some embodiment, the humanized SIRPα locus comprises a rodent (e.g., mouse) 5'-UTR. In some embodiments, the humanization comprises a human 3'-UTR. In appropriate cases, it may be reasonable to presume that the mouse and human SIRPα genes appear to be similarly regulated based on the similarity of their 5'-flanking sequence. As shown in the present disclosure, humanized SIRPα mice that comprise a replacement at an endogenous mouse SIRPα locus, which retain mouse regulatory elements but comprise a humanization of SIRPα encoding sequence, do not exhibit obvious pathologies. Both genetically modified mice that are heterozygous or homozygous for humanized SIRPα are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized SIRPα gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized SIRPα in the genome of the animal.

In some embodiments, the non-human mammal comprises the genetic construct as described herein. In some embodiments, a non-human mammal expressing human or humanized SIRPα is provided. In some embodiments, the tissue-specific expression of human or humanized SIRPα protein is provided.

In some embodiments, the expression of human or humanized SIRPα in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human SIRPα protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized SIRPα protein.

Vectors

The present disclosure relates to a targeting vector, comprising: a) a DNA fragment homologous to the 5' end of a region to be altered (5' arm), which is selected from the SIRPα gene genomic DNAs in the length of 100 to 10,000 nucleotides; b) a desired/donor DNA sequence encoding a donor region; and c) a second DNA fragment homologous to the 3' end of the region to be altered (3' arm), which is selected from the SIRPα gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000068.7; c) the DNA fragment homologous to the 3' end of the region to be altered (3' arm) is selected from the nucleotide sequences that have at least 90% homology to the NCBI accession number NC_000068.7.

In some embodiments, a) the DNA fragment homologous to the 5' end of a region to be altered (5' arm) is selected from the nucleotides from the position 129607346 to the position 129608914 of the NCBI accession number NC_000068.7; c) the DNA fragment homologous to the 3' end of the region to be altered (3' arm) is selected from the nucleotides from the position 129609239 to the position 129610638 of the NCBI accession number NC_000068.7.

In some embodiments, the length of the selected genomic nucleotide sequence in the targeting vector can be about 3 kb, about 3.5 kb, about 4 kb, about 4.5 kb, or about 5 kb.

In some embodiments, the region to be altered is exon 1, exon 2, exon 3, exon 4, exon 5, exon 6, exon 7, or exon 8 of SIRPα gene (e.g., exon 2 of mouse SIRPα gene).

The targeting vector can further include a selected gene marker.

In some embodiments, the sequence of the 5' arm is shown in SEQ ID NO: 29; and the sequence of the 3' arm is shown in SEQ ID NO: 30.

In some embodiments, the sequence is derived from human (e.g., 1915110-1915433 of NC_000020.11). For example, the target region in the targeting vector is a part or entirety of the nucleotide sequence of a human SIRPα, preferably exon 2 of the human SIRPα. In some embodiments, the nucleotide sequence of the humanized SIRPα encodes the entire or the part of human SIRPα protein (e.g., SEQ ID NO: 4).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., “Delivery technologies for genome editing,” Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous SIRPα gene locus, a sequence encoding a region of an endogenous SIRPα with a sequence encoding a corresponding region of human or chimeric SIRPα. In some embodiments, the replacement occurs in a germ cell, a somatic cell, a blastocyst, or a fibroblast, etc. The nucleus of a somatic cell or the fibroblast can be inserted into an enucleated oocyte.

Figure 17:
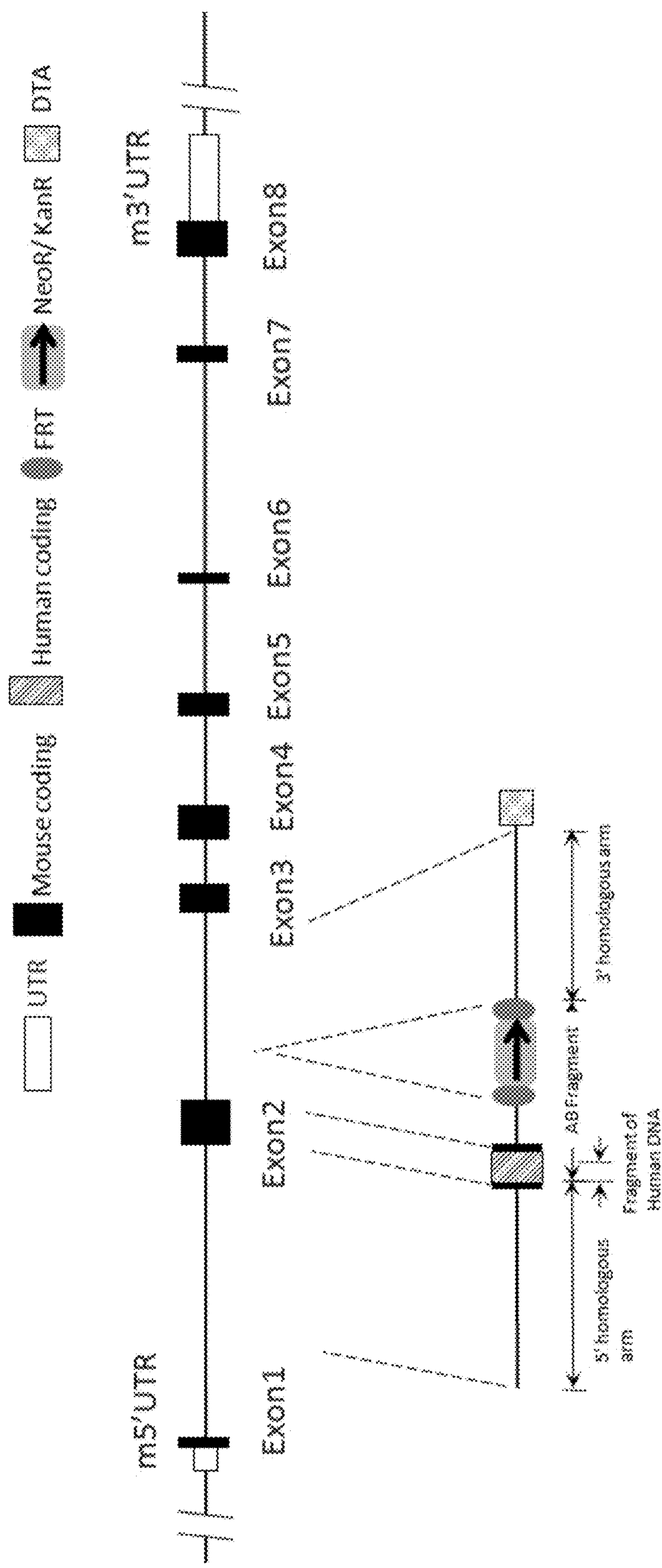
FIG. 17 is a schematic diagram showing gene targeting strategy using embryonic stem (ES) cells.

FIG. 17 shows a humanization strategy for a mouse SIRPα locus. In FIG. 17, the targeting strategy involves a vector comprising the 5' end homologous arm, human SIRPα gene fragment, 3' homologous arm. The process can involve replacing endogenous SIRPα sequence with human sequence by homologous recombination. In some embodiments, the cleavage at the upstream and the downstream of the target site (e.g., by zinc finger nucleases, TALEN or CRISPR) can result in DNA double strand break, and the homologous recombination is used to replace endogenous SIRPα sequence with human SIRPα sequence.

Thus, in some embodiments, the methods for making a genetically modified, humanized animal, can include the step of replacing at an endogenous SIRPα locus (or site), a nucleic acid encoding a sequence encoding a region of endogenous SIRPα with a sequence encoding a corresponding region of human SIRPα. The sequence can include a region (e.g., a part or the entire region) of exon 1, exon 2, exon 3, exon 4, exon 5, exon 6, exon 7, exon 8, and/or exon 9 of a human SIRPα gene. In some embodiments, the sequence includes a region of exon 3 of a human SIRPα gene (e.g., amino acids 31-138 of SEQ ID NO: 4). In some embodiments, the region is located within the extracellular region of SIRPα. In some embodiments, the endogenous SIRPα locus is exon 2 of mouse SIRPα.

In some embodiments, the methods of modifying a SIRPα locus of a mouse to express a chimeric human/mouse SIRPα peptide can include the steps of replacing at the endogenous mouse SIRPα locus a nucleotide sequence encoding a mouse SIRPα with a nucleotide sequence encoding a human SIRPα, thereby generating a sequence encoding a chimeric human/mouse SIRPα.

In some embodiments, the nucleotide sequence encoding the chimeric human/mouse SIRPα can include a first nucleotide sequence encoding a region of the extracellular region of mouse SIRPα (with or without the mouse or human signal peptide sequence); a second nucleotide sequence encoding a region of the extracellular region of human SIRPα; a third nucleotide sequence encoding the transmembrane region, and/or the cytoplasmic region of a mouse SIRPα.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a SIRPα gene humanized animal model, involving the following steps:

(a) providing the cell (e.g. a fertilized egg cell) based on the methods described herein;
(b) culturing the cell in a liquid culture medium;
(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 or BALB/c mouse).

In some embodiments, the non-human mammal in step (c) is a female with pseudo pregnancy (or false pregnancy).

In some embodiments, the fertilized eggs for the methods described above are C57BL/6 or BALB/c fertilized eggs. Other fertilized eggs that can also be used in the methods as described herein include, but are not limited to, FVB/N fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized SIRPα protein, e.g., in a physiologically appropriate manner, provide a variety of uses that include, but are not limited to, developing therapeutics for human diseases and disorders, and assessing the toxicity and/or efficacy of these human therapeutics in the animal models.

In various aspects, genetically modified animals are provided that express human or humanized SIRPα, which are useful for testing agents that can decrease or block the interaction between SIRPα and CD47 or the interaction between SIRPα and other SIRPα receptors or ligands (e.g., surfactant protein A and D), testing whether an agent can increase or decrease the immune response, and/or determining whether an agent is an SIRPα agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-SIRPα antibody for the treatment of cancer. The methods involve administering the anti-SIRPα antibody to the animal as described herein, wherein the animal has a tumor; and determining the inhibitory effects of the anti-SIRPα antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-SIRPα antibody or anti-CD47 antibody prevents CD47 from binding to SIRPα. In some embodiments, the anti-SIRPα antibody or anti-CD47 antibody cannot prevent CD47 from binding to SIRPα (e.g., endogenous SIRPα).

In some embodiments, the genetically modified animals can be used for determining whether an anti-SIRPα antibody is a SIRPα agonist or antagonist. In some embodiments, the methods as described herein are also designed to determine the effects of the agent (e.g., anti-SIRPα antibodies) on SIRPα, e.g., whether the agent can stimulate macrophages, whether the agent can initiate an antitumor T-cell immune response, and/or whether the agent can upregulate the immune response or downregulate immune response. In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-SIRPα antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-SIRPα antibody or anti-CD47 antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the antibody is designed for treating hepatocellular, ovarian, colon, or cervical carcinomas. In some embodiments, the antibody is designed for treating advanced breast cancer, advanced ovarian cancer, and/or advanced refractory solid tumor. In some embodiments, the antibody is designed for treating metastatic solid tumors, NSCLC, melanoma, non-Hodgkin lymphoma, colorectal cancer, and multiple myeloma. In some embodiments, the treatment is designed for treating acute myeloid leukemia, non-Hodgkin's lymphoma, bladder cancer, or breast cancer.

In some embodiments, the antibody is designed for treating various autoimmune diseases. Thus, the methods as described herein can be used to determine the effectiveness of an antibody in inhibiting immune response.

The present disclosure also provides methods of determining toxicity of an antibody (e.g., anti-SIRPα antibody or anti-CD47 antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the SIRPα gene function, human SIRPα antibodies, drugs for human SIRPα targeting sites, the drugs or efficacies for human SIRPα targeting sites, the drugs for immune-related diseases and antitumor drugs.

Humanized CD47 Animal

CD47 is a ~50 kDa heavily glycosylated, ubiquitously expressed membrane protein of the immunoglobulin superfamily with a single IgV-like domain at its N-terminus, a highly hydrophobic stretch with five membrane-spanning segments and an alternatively spliced cytoplasmic C-terminus.

Overexpression of CD47 has been found in nearly all types of tumors. Also, CD47 expression on cancer stem cells (CSCs) implies its role in cancer recurrence. It can increase the chance of CSC survival, which in turn could repopulate a new tumor mass and cause a tumor relapse.

CD47 down-regulation is also involved in the clearance of red blood cells (RBCs) and platelets by splenic macrophages, which may cause hemolytic anemia and idiopathic thrombocytopenic purpura, respectively. Thus, when CD47 antagonists are used as therapies, it is also very important to assess its toxicities.

A detailed description of CD47 and its function can be found, e.g., in Liu, Xiaojuan, et al. "Is CD47 an innate immune checkpoint for tumor evasion?." Journal of hematology & oncology 10.1 (2017): 12; Huang et al. "Targeting CD47: the achievements and concerns of current studies on cancer immunotherapy." Journal of thoracic disease 9.2 (2017): E168; which are incorporated by reference herein in the entirety.

In human genomes, CD47 gene (Gene ID: 961) locus has 11 exons, exon 1, exon 2, exon 3, exon 4, exon 5, exon 6, exon 7, exon 8, exon 9, exon 10, and exon 11. The CD47 protein has an extracellular N-terminal IgV domain, five transmembrane domains, a short C-terminal intracellular tail. In addition, it has two extracellular regions and two intracellular regions between neighboring transmembrane domains. The signal peptide is located at the extracellular N-terminal IgV domain of CD47. The nucleotide sequence for human CD47 mRNA is NM_001777.3 (SEQ ID NO: 91), and the amino acid sequence for human CD47 is NP_001768.1 (SEQ ID NO: 92). The location for each exon and each region in human CD47 nucleotide sequence and amino acid sequence is listed below:

TABLE 5

| Human CD47 (approximate location) | NM_001777.3 5346 bp (SEQ ID NO: 91) | NP_001768.1 323 aa (SEQ ID NO: 92) |
|---|---|---|
| Exon 1 | 1-226 | 1-15 |
| Exon 2 | 227-580 | 16-133 |
| Exon 3 | 581-670 | 134-163 |
| Exon 4 | 671-778 | 164-199 |
| Exon 5 | 779-871 | 200-230 |
| Exon 6 | 872-964 | 231-261 |
| Exon 7 | 965-1057 | 262-292 |
| Exon 8 | 1058-1089 | 293-303 |
| Exon 9 | 1090-1114 | 304-311 |
| Exon 10 | 1115-1147 | 312-322 |
| Exon 11 | 1148-5346 | 323 |
| Signal peptide | 181-234 | 1-18 |
| Donor region in one example | 247-558* (with point mutation 375(T→C)) | 23-126 |

The extracellular N-terminal IgV domain is 19-141 of SEQ ID NO: 92, and the C-terminal intracellular tail is located at 290-323 of SEQ ID NO: 92. Thus, the donor region is located within the extracellular N-terminal IgV domain.

Human CD47 also have several transcript variants. These variants are summarized below.

TABLE 6

| Human CD47 transcript variants | Amino acid sequences |
| --- | --- |
| NM_001777.3 (5346bp) | NP_001768.1 (323 aa) |
| NM_198793.2 (5288bp) | NP_942088.1 (305 aa) |
| XM_005247909.1 (5021bp) | XP_005247966.1 (293 aa) |
| XM_005247908.1 (5078bp) | XP_005247965.1 (312 aa) |

In mice, CD47 gene locus has 10 exons, exon 1, exon 2, exon 3, exon 4, exon 5, exon 6, exon 7, exon 8, exon 9, and exon 10. The mouse CD47 protein also has an extracellular N-terminal IgV domain, five transmembrane domains, and a short C-terminal intracellular tail, and the signal peptide is located at the extracellular N-terminal IgV domain of CD47. The nucleotide sequence for mouse CD47 cDNA is NM_010581.3 (SEQ ID NO: 93), the amino acid sequence for mouse CD47 is NP_034711.1 (SEQ ID NO: 94). The location for each exon and each region in the mouse CD47 nucleotide sequence and amino acid sequence is listed below:

TABLE 7

| Mouse CD47 (approximate location) | NM_010581.3 1928 bp (SEQ ID NO: 93) | NP_034711.1 324 aa (SEQ ID NO: 94) |
| --- | --- | --- |
| Exon 1 | 1-179 | 1-15 |
| Exon 2 | 180-527 | 16-131 |
| Exon 3 | 528-590 | 132-152 |
| Exon 4 | 591-680 | 153-182 |
| Exon 5 | 681-788 | 183-218 |
| Exon 6 | 789-881 | 219-249 |
| Exon 7 | 882-974 | 250-280 |
| Exon 8 | 975-1067 | 281-311 |
| Exon 9 | 1068-1099 | 312-322 |
| Exon 10 | 1100-1919 | 323-324 |
| Signal peptide | 134-187 | 1-18 |
| Replaced region in one example | 200-505 | 23-124 |

The mouse CD47 gene (Gene ID: 16423) is located in Chromosome 16 of the mouse genome, which is located from 49855253 to 49912424, of NC_000082.6 (GRCm38.p4 (GCF 000001635.24)). The 5'-UTR is from 49855618 to 49855786, exon 1 is from 49,855,618 to 49,855,832, the first intron is from 49,855,833 to 49,867,764, exon 2 is from 49,867,765 to 49,868,112, the second intron is from 49,868,113 to 49,869,017, exon 3 is from 49,869,018 to 49,869,080, the third intron is from 49,869,081 to 49,884,164, exon 4 is from 49,884,165 to 49,884,254, the fourth intron is from 49,884,255 to 49,894,176, exon 5 is from 49,894,177 to 49,894,284, the fifth intron is from 49,894,285 to 49,895,368, exon 6 is from 49,895,369 to 49,895,461, the sixth intron is from 49,895,462 to 49,896,355, exon 7 is from 49,896,356 to 49,896,448, the seventh intron is from 49,896,449 to 49,898,039, exon 8 is from 49,898,040 to 49,898,132, the eighth intron is from 49,898,133 to 49,906,780, exon 9 is from 49,906,781 to 49,906,812, the ninth intron is from 49,906,813 to 49,910,868, exon 10 is from 49,910,869 to 49,915,010, the 3'-UTR is from 49910878 to 49,915,010, based on transcript NM_010581.3. All relevant information for mouse CD47 locus can be found in the NCBI website with Gene ID: 16423, which is incorporated by reference herein in its entirety.

Like human CD47, the mouse CD47 has several transcript variants. A portion of these sequences can also be replaced by corresponding human sequences. Some exemplary sequences are shown in Table 8.

TABLE 8

| Mouse CD47 sequence | |
| --- | --- |
| mRNA sequence | Amino acid sequence |
| NM_010581.3 (1928bp) | NP_034711.1 (324aa) |
| XM_006521809.3 (3101bp) | XP_006521872.1 (320aa) |
| XM_006521806.3 (3114bp) | XP_006521869.1 (342aa) |
| XM_006521807.3 (3081bp) | XP_006521870.1 (331aa) |
| XM_006521810.3 (3024bp) | XP_006521873.1 (312aa) |
| XM_006521808.3 (3051bp) | XP_006521871.1 (321aa) |
| XM_006521811.3 (2993bp) | XP_006521874.1 (303aa) |

FIG. 26 shows the alignment between mouse CD47 amino acid sequence (NP_034711.1; SEQ ID NO: 94) and human CD47 amino acid sequence (NP_001768.1; SEQ ID NO: 92). Thus, the corresponding amino acid residue or region between human and mouse CD47 can also be found in FIG. 26.

CD47 genes, proteins, and locus of the other species are also known in the art. For example, the gene ID for CD47 in *Rattus norvegicus* is 29364, the gene ID for CD47 in *Macaca mulatta* (Rhesus monkey) is 704980, the gene ID for CD47 in *Canis lupus familiaris* (dog) is 478552, and the gene ID for CD47 in *Cavia porcellus* (domestic guinea pig) is 100727770. The relevant information for these genes (e.g., intron sequences, exon sequences, amino acid residues of these proteins) can be found, e.g., in NCBI database.

The present disclosure provides human or chimeric (e.g., humanized) CD47 nucleotide sequence and/or amino acid sequences. In some embodiments, the entire sequence of mouse exon 1, exon 2, exon 3, exon 4, exon 5, exon 6, exon 7, exon 8, exon 9, exon 10, signal peptide, the extracellular N-terminal IgV domain, the transmembrane domains (e.g., the first transmembrane domain, the second transmembrane domain, the third transmembrane domain, the fourth transmembrane domain, and/or the fifth transmembrane domain), and/or the C-terminal intracellular region are replaced by the corresponding human sequence. As used herein, the first transmembrane domain refers to the first transmembrane domain starting from the N-terminal of CD47. Similarly, the second, third, fourth, and fifth transmembrane domain refers to the second, third, fourth, and fifth transmembrane domain starting from the N-terminal of CD47.

In some embodiments, a "region" or "portion" of mouse exon 1, exon 2, exon 3, exon 4, exon 5, exon 6, exon 7, exon 8, exon 9, exon 10, signal peptide, the extracellular N-terminal IgV domain, the transmembrane domains (e.g., the first transmembrane domain, the second transmembrane domain, the third transmembrane domain, the fourth transmembrane domain, and/or the fifth transmembrane domain), and/or the C-terminal intracellular region is replaced by the corresponding human sequence.

In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, exon 9, exon 10, signal peptide, the extracellular N-terminal IgV domain, the transmembrane domains (e.g., the first transmembrane domain, the second transmembrane domain, the third transmembrane domain, the fourth transmembrane domain, and/or the fifth transmembrane domain), and/or the C-terminal intracellular region. In some embodiments, a region, a portion, or the entire sequence of mouse exon 2 is replaced by a region, a portion, or the entire sequence of human exon 2.

In some embodiments, a "region" or "portion" of mouse exon 1, exon 2, exon 3, exon 4, exon 5, exon 6, exon 7, exon 8, exon 9, exon 10, signal peptide, the extracellular N-terminal IgV domain, the transmembrane domains (e.g., the first transmembrane domain, the second transmembrane domain, the third transmembrane domain, the fourth transmembrane domain, and/or the fifth transmembrane domain), and/or the C-terminal intracellular region is deleted.

Thus, in some embodiments, the present disclosure also provides a chimeric (e.g., humanized) CD47 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse CD47 mRNA sequence (e.g., SEQ ID NO: 93), mouse CD47 amino acid sequence (e.g., SEQ ID NO: 94), or a portion thereof (e.g., exon 1, exon 2, exon 3, exon 4, exon 5, exon 6, exon 7, exon 8, exon 9, or exon 10); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human CD47 mRNA sequence (e.g., SEQ ID NO: 91), human CD47 amino acid sequence (e.g., SEQ ID NO: 92), or a portion thereof (e.g., exon 1, exon 2, exon 3, exon 4, exon 5, exon 6, exon 7, exon 8, exon 9, exon 10, or exon 11).

In some embodiments, the sequence encoding amino acids 23-124 of mouse CD47 (SEQ ID NO: 94) is replaced. In some embodiments, the sequence is replaced by a sequence encoding a corresponding region of human CD47 (e.g., amino acids 23-126 of human CD47 (SEQ ID NO: 92)).

In some embodiments, the nucleic acids as described herein are operably linked to a promotor or regulatory element, e.g., an endogenous mouse CD47 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse CD47 nucleotide sequence (e.g., exon 1, exon 2, exon 3, exon 4, exon 5, exon 6, exon 7, exon 8, exon 9, exon 10, or SEQ ID NO: 93).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse CD47 nucleotide sequence (e.g., exon 1, exon 2, exon 3, exon 4, exon 5, exon 6, exon 7, exon 8, exon 9, exon 10, or SEQ ID NO: 93).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human CD47 nucleotide sequence (e.g., exon 1, exon 2, exon 3, exon 4, exon 5, exon 6, exon 7, exon 8, exon 9, exon 10, exon 11, or SEQ ID NO: 91).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human CD47 nucleotide sequence (e.g., exon 1, exon 2, exon 3, exon 4, exon 5, exon 6, exon 7, exon 8, exon 9, exon 10, exon 11, or SEQ ID NO: 91).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse CD47 amino acid sequence (e.g., exon 1, exon 2, exon 3, exon 4, exon 5, exon 6, exon 7, exon 8, exon 9, exon 10, or SEQ ID NO: 94).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse CD47 amino acid sequence (e.g., exon 1, exon 2, exon 3, exon 4, exon 5, exon 6, exon 7, exon 8, exon 9, exon 10, or SEQ ID NO: 94).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human CD47 amino acid sequence (e.g., exon 1, exon 2, exon 3, exon 4, exon 5, exon 6, exon 7, exon 8, exon 9, exon 10, exon 11, or SEQ ID NO: 92).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human CD47 amino acid sequence (e.g., exon 1, exon 2, exon 3, exon 4, exon 5, exon 6, exon 7, exon 8, exon 9, exon 10, exon 11, or SEQ ID NO: 92).

In some embodiments, the percentage identity with the sequence shown in SEQ ID NO: 101 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

Cells, tissues, and animals (e.g., mouse) are also provided that comprise the nucleotide sequences as described herein, as well as cells, tissues, and animals (e.g., mouse) that express human or chimeric (e.g., humanized) CD47 from an endogenous non-human CD47 locus.

In one aspect, the disclosure provides a genetically-modified, non-human animal whose genome comprises at least one chromosome comprising a sequence encoding a human or chimeric CD47.

In some embodiments, the sequence encoding the human or chimeric CD47 is operably linked to an endogenous regulatory element at the endogenous CD47 gene locus in the at least one chromosome.

In some embodiments, the sequence encoding a human or chimeric CD47 comprises a sequence encoding an amino acid sequence that is at least 50%, 55%, 65%, 70%, 75%, 80%, 85%, 90%, 95%, 99%, or 100% identical to human CD47 (SEQ ID NO: 92).

In some embodiments, the sequence encoding a human or chimeric CD47 comprises a sequence encoding an amino acid sequence that is at least 50%, 55%, 65%, 70%, 75%, 80%, 85%, 90%, 95%, 99%, or 100% identical to SEQ ID NO: 101.

In some embodiments, the sequence encoding a human or chimeric CD47 comprises a sequence that is at least 50%, 55%, 65%, 70%, 75%, 80%, 85%, 90%, 95%, 99%, or 100% identical to amino acids 23-126 of SEQ ID NO: 92.

In some embodiments, the animal is a mammal, e.g., a monkey, a rodent or a mouse. In some embodiments, the animal is a BALB/c mouse or a C57BL/6 mouse.

In some embodiments, the animal does not express endogenous CD47. In some embodiments, the animal has one or more cells expressing human or chimeric CD47.

In some embodiments, the animal has one or more cells expressing human or chimeric CD47, and the expressed human or chimeric CD47 can bind to endogenous SIRPα. In some embodiments, the animal has one or more cells expressing human or chimeric CD47, and the expressed human or chimeric CD47 cannot bind to endogenous SIRPα.

In another aspect, the disclosure is related to a genetically-modified, non-human animal, wherein the genome of the animal comprises a replacement of a sequence encoding a region of endogenous CD47 with a sequence encoding a corresponding region of human CD47 at an endogenous CD47 gene locus.

In some embodiments, the sequence encoding the corresponding region of human CD47 is operably linked to an endogenous regulatory element at the endogenous CD47 locus, and one or more cells of the animal expresses a chimeric CD47.

In some embodiments, the animal does not express endogenous CD47. In some embodiments, the replaced locus is the extracellular N-terminal IgV domain of CD47.

In some embodiments, the animal has one or more cells expressing a chimeric CD47 having an extracellular N-terminal IgV domain, wherein the extracellular N-terminal IgV domain comprises a sequence that is at least 50%, 60%, 70%, 80%, 90%, 95%, or 99% identical to the extracellular N-terminal IgV domain of human CD47.

In some embodiments, the extracellular N-terminal IgV domain of the chimeric CD47 has a sequence that has at least 10, 20, 30, 40, 50, 60, 70, 80, 90, or 100 contiguous amino acids that are identical to a contiguous sequence present in the extracellular N-terminal IgV domain of human CD47.

In some embodiments, the animal is a mouse, and the replaced endogenous CD47 locus is exon 1, exon 2, exon 3, exon 4, exon 5, exon 6, exon 7, exon 8, exon 9, and/or exon 10 of the endogenous mouse CD47 gene.

In some embodiments, the animal is heterozygous with respect to the replacement at the endogenous CD47 gene locus. In some embodiments, the animal is homozygous with respect to the replacement at the endogenous CD47 gene locus.

In another aspect, the disclosure is related to methods for making a genetically-modified, non-human animal. The methods involve replacing in at least one cell of the animal, at an endogenous CD47 gene locus, a sequence encoding a region of an endogenous CD47 with a sequence encoding a corresponding region of human CD47.

In some embodiments, the sequence encoding the corresponding region of human CD47 comprises exon 2 of a human CD47 gene.

In some embodiments, the sequence encoding the corresponding region of CD47 comprises at least 100, 150, 200, 250, or 300 nucleotides of exon 2 of a human CD47 gene.

In some embodiments, the sequence encoding the corresponding region of human CD47 encodes a sequence that is at least 90% identical to amino acids 23-126 of SEQ ID NO: 92.

In some embodiments, the locus is located within the extracellular N-terminal IgV domain of CD47.

In some embodiments, the animal is a mouse, and the locus is exon 1, exon 2, exon 3, exon 4, exon 5, exon 6, exon 7, exon 8, exon 9, and/or exon 10 of the mouse CD47 gene (e.g., exon 2).

In another aspect, the disclosure is also related to a non-human animal comprising at least one cell comprising a nucleotide sequence encoding a chimeric CD47 polypeptide, wherein the chimeric CD47 polypeptide comprises at least 50 contiguous amino acid residues that are identical to the corresponding contiguous amino acid sequence of a human CD47, wherein the animal expresses the chimeric CD47.

In some embodiments, the chimeric CD47 polypeptide has at least 50 contiguous amino acid residues that are identical to the corresponding contiguous amino acid sequence of a human CD47 extracellular N-terminal IgV domain.

In some embodiments, the chimeric CD47 polypeptide comprises a sequence that is at least 90%, 95%, or 99% identical to amino acids 23-126 of SEQ ID NO: 92.

In some embodiments, the nucleotide sequence is operably linked to an endogenous CD47 regulatory element of the animal.

In some embodiments, the chimeric CD47 polypeptide comprises five endogenous CD47 transmembrane regions and/or an endogenous CD47 C-terminal intracellular tail.

In some embodiments, the nucleotide sequence is integrated to an endogenous CD47 gene locus of the animal.

In some embodiments, the chimeric CD47 has at least one mouse CD47 activity and/or at least one human CD47 activity.

In another aspect, the disclosure is also related to methods of making a genetically-modified mouse cell that expresses a chimeric CD47. The methods involve replacing, at an endogenous mouse CD47 gene locus, a nucleotide sequence encoding a region of mouse CD47 with a nucleotide sequence encoding a corresponding region of human CD47, thereby generating a genetically-modified mouse cell that includes a nucleotide sequence that encodes the chimeric CD47, wherein the mouse cell expresses the chimeric CD47.

In some embodiments, the chimeric CD47 comprises: an extracellular N-terminal IgV domain of human CD47; and one or more transmembrane domains of mouse CD47 and/or a C-terminal intracellular tail of mouse CD47.

In some embodiments, the nucleotide sequence encoding the chimeric CD47 is operably linked to an endogenous CD47 regulatory region, e.g., promoter.

In some embodiments, the animal further comprises a sequence encoding an additional human or chimeric protein (e.g., SIRPα, programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), CD137, or TNF Receptor Superfamily Member 4 (OX40)).

In some embodiments, the additional human or chimeric protein is SIRPα and/or PD-1.

In one aspect, the disclosure also provides methods of determining effectiveness of a CD47 antagonist (e.g., an anti-CD47 antibody) for the treatment of cancer. The methods involve administering the CD47 antagonist to the animal described herein, wherein the animal has a tumor; and determining the inhibitory effects of the CD47 antagonist to the tumor.

In some embodiments, the animal comprises one or more cells that express SIRPα. In some embodiments, the tumor comprises one or more cells that express CD47.

In some embodiments, the tumor comprises one or more cancer cells that are injected into the animal.

In some embodiments, determining the inhibitory effects of the CD47 antagonist (e.g., an anti-CD47 antibody) to the tumor involves measuring the tumor volume in the animal.

In some embodiments, the tumor cells are melanoma cells, non-small cell lung carcinoma (NSCLC) cells, small cell lung cancer (SCLC) cells, non-Hodgkin lymphoma cells, bladder cancer cells, prostate cancer cells, breast cancer cells, ovarian cancer cells, colorectal cancer cells, and/or refractory solid tumor cells.

In another aspect, the disclosure also provides methods of determining effectiveness of a CD47 antagonist (e.g., an anti-CD47 antibody) and an additional therapeutic agent for the treatment of a tumor. The methods involve administering the CD47 antagonist and the additional therapeutic agent to the animal as described herein, wherein the animal has a tumor; and determining the inhibitory effects on the tumor.

In some embodiments, the animal further comprises a sequence encoding a human or chimeric SIRPα.

In some embodiments, the additional therapeutic agent is an anti-SIRPα antibody.

In some embodiments the additional therapeutic agent is an anti-PD-1 antibody, an anti-PD-L1 antibody, an anti-CTLA4 antibody, an anti-CD20 antibody, an anti-EGFR antibody, or an anti-CD319 antibody.

In some embodiments, the tumor comprises one or more tumor cells that express CD47.

In some embodiments, the tumor is caused by injection of one or more cancer cells into the animal.

In some embodiments, determining the inhibitory effects of the treatment involves measuring the tumor volume in the animal.

In some embodiments the tumor comprises melanoma cells, non-small cell lung carcinoma (NSCLC) cells, small cell lung cancer (SCLC) cells, non-Hodgkin lymphoma cells, bladder cancer cells, prostate cancer cells, breast cancer cells, ovarian cancer cells, colorectal cancer cells, and/or refractory solid tumor cells.

In another aspect, the disclosure further provides methods of determining toxicity of an agent (e.g., a CD47 antagonist). The methods involve administering the agent to the animal as described herein; and determining weight change of the animal. In some embodiments, the method further involve performing a blood test (e.g., determining red blood cell count).

In one aspect, the disclosure relates to proteins comprising an amino acid sequence, wherein the amino acid sequence is one of the following:

(e) an amino acid sequence set forth in SEQ ID NO: 101;
(f) an amino acid sequence that is at least 90%, 91%, 92%, 93%, 94%, 95%, 96%, 97%, 98%, or 99% identical to SEQ ID NO: 101;
(g) an amino acid sequence that is different from the amino acid sequence set forth in SEQ ID NO: 101 by no more than 10, 9, 8, 7, 6, 5, 4, 3, 2 or 1 amino acid; and
(h) an amino acid sequence that comprises a substitution, a deletion and/or insertion of one, two, three, four, five or more amino acids to the amino acid sequence set forth in SEQ ID NO: 101.

In some embodiments, provided herein are cells comprising the proteins disclosed herein. In some embodiments, provided herein are animals having the proteins disclosed herein.

In another aspect, the disclosure relates to nucleic acids comprising a nucleotide sequence, wherein the nucleotide sequence is one of the following:

(d) a sequence that encodes the protein as described herein;
(e) SEQ ID NO: 99 or SEQ ID NO: 100;
(f) a sequence that is at least 90%, 91%, 92%, 93%, 94%, 95%, 96%, 97%, 98%, or 99% identical to SEQ ID NO: 99 or SEQ ID NO: 100.

In some embodiments, provided herein are cells comprising the nucleic acids disclosed herein. In some embodiments, provided herein are animals having the nucleic acids disclosed herein.

In another aspect, the disclosure also provides a genetically-modified, non-human animal whose genome comprise a disruption in the animal's endogenous CD47 gene, wherein the disruption of the endogenous CD47 gene comprises deletion of exon 2 or part thereof of the endogenous CD47 gene.

In some embodiments, the disruption of the endogenous CD47 gene further comprises deletion of one or more exons or part of exons selected from the group consisting of exon 1, exon 3, exon 4, exon 5, exon 6, exon 7, exon 8, exon 9, and exon 10 of the endogenous CD47 gene.

In some embodiments, the disruption of the endogenous CD47 gene further comprises deletion of one or more introns or part of introns selected from the group consisting of intron 1, intron 2, intron 3, intron 4, intron 5, intron 6, intron 7, intron 8, and intron 9 of the endogenous CD47 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous CD47 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, exon 5, exon 6, exon 7, exon 8, exon 9, or exon 10 (e.g., deletion of at least 300 nucleotides of exon 2).

Genetically Modified Animal Model with Two or More Human or Chimeric Genes

The present disclosure further relates to methods for generating genetically modified animal model with two or more human or chimeric genes. The animal can comprise a human or chimeric SIRPα gene and a sequence encoding one or more additional human or chimeric protein.

In some embodiments, the additional human or chimeric protein can be CD47, programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), CD137, or TNF Receptor Superfamily Member 4 (TNFRSF4 or OX40).

In some embodiments, the additional human or chimeric protein is CD47. The animal can have a human or chimeric SIRPα gene as described herein and a human or chimeric CD47 gene as described herein. The animal can be used to determine the toxicities and the efficacy of an anti-SIRPα antibody or an anti-CD47 antibody at the same time. In some embodiments, one or more exons of CD47 are replaced by human sequences. In some embodiments, the replaced CD47 region is exon 2 of the endogenous mouse CD47 gene.

The methods of generating genetically modified animal model with two or more human or chimeric genes (e.g., humanized genes) can include the following steps:

(a) using the methods of introducing human SIRPα gene or chimeric SIRPα gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD28, TIGIT, TIM-3, GITR, OX40, CD137, or CD47. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/117984, PCT/CN2017/120388; each of which is incorporated herein by reference in its entirety.

In some embodiments, the SIRPα humanization is directly performed on a genetically modified animal having a human or chimeric CD47, PD-1, CTLA-4, BTLA, PD-L1, CD27, CD28, TIGIT, TIM-3, GITR, CD137, or OX40 gene.

In some embodiments, the SIRPα humanization is directly performed on a genetically modified animal having a human or chimeric CD47.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-SIRPα antibody and an additional therapeutic agent for the treatment of cancer. The methods include administering the anti-SIRPα antibody and the additional therapeutic agent to the animal, wherein the animal has a tumor; and determining the inhibitory effects of the combined treatment to the tumor. In some embodiments, the additional therapeutic agent is an antibody that specifically binds to CD47, PD-1, CTLA-4, BTLA, PD-L1, CD27, CD28, TIGIT, TIM-3, GITR, CD137, or OX40. In some embodiments, the additional therapeutic agent is an anti-CTLA4 antibody (e.g., ipilimumab), an anti-CD20 antibody (e.g., rituximab), an anti-EGFR antibody (e.g., cetuximab), and an anti-CD319 antibody (e.g., elotuzumab), or anti-PD-1 antibody (e.g., nivolumab).

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD47, CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the treatment is designed for treating acute myeloid leukemia, non-Hodgkin's lymphoma, bladder cancer, and breast cancer.

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

C57BL/6 mice were purchased from the China Food and Drugs Research Institute National Rodent Experimental Animal Center.

EcoRI, BamHI, ASeI restriction enzymes were purchased from NEB (Catalog numbers: R3101M, R3136M, and R0526S).

Ambion in vitro transcription kit from Ambion, catalog number AM1354.

UCA kit was obtained from Beijing BioCytogen Co., Ltd. (Catalog number: BCG-DX-001)

Reverse Transcription Kit was obtained from Takara (Catalog number: 6110A).

TOP10 competent cells were purchased from the Tiangen Biotech (Beijing) Co. (Catalog number: CB104-02).

Cas9 mRNA from SIGMA, catalog number CAS9MRNA-1EA.

AIO kit was obtained from Beijing Biocytogen Co., Ltd. (Catalog number: BCG-DX-004).

pHSG299 plasmid was from Takara (Catalog number 3299).

Anti-mCD3 antibody was obtained from BD (Catalog number: 553057).

PerCP/Cy5.5 anti-mouse TCR β chain (mTcRβ PerCP) antibody was purchased from Biolegend (Catalog number: 109228).

Alexa Fluor® 647 anti-mouse CD47 antibody (mCD47 Alexa Fluor 647, AF647) was purchased from Biolegend (Catalog number 127510).

PE anti-human CD47 (hCD47 PE) antibody was purchased from Biolegend, Catalog number 323108.

PE anti-mouse CD172a (SIRPα) antibody (mSIRPα PE) was purchased from Biolegend, Catalog number 144012.

APC anti-human CD172a/b (SIRPα/β) Antibody (hSIRPα APC) was purchased from Biolegend (Catalog number: 323810).

PE anti-mouse CD11b (mCD11b PE) antibody was purchased from Biolegend, Catalog number 101208.

FITC anti-mouse F4/80 (mF4/80 FITC) antibody was purchased from Biolegend, Catalog number 123108.

Flow cytometer was purchased from BD Biosciences (model: FACS Calibur™)

Example 1: Sequence Design for Humanization of SIRPα

The human SIRPα gene and the mouse SIRPA gene both have multiple transcript variants. The sequence design below was based on one transcript variant.

One transcript variant of the mouse SIRPα gene (Gene ID: 19261) is NM_007547.4 with the corresponding protein NP_031573.2. The mRNA sequence is shown in SEQ ID NO: 1. The corresponding protein sequence is shown in SEQ ID NO: 2. In this experimental design, the majority of exon 2 of mouse SIRPα was replaced with the corresponding sequence of human SIRPα (gene ID: 140885; transcript NM_080792.2 (SEQ ID NO: 3) corresponding to NP_542970.1 (SEQ ID NO: 4)).

Figure 2:
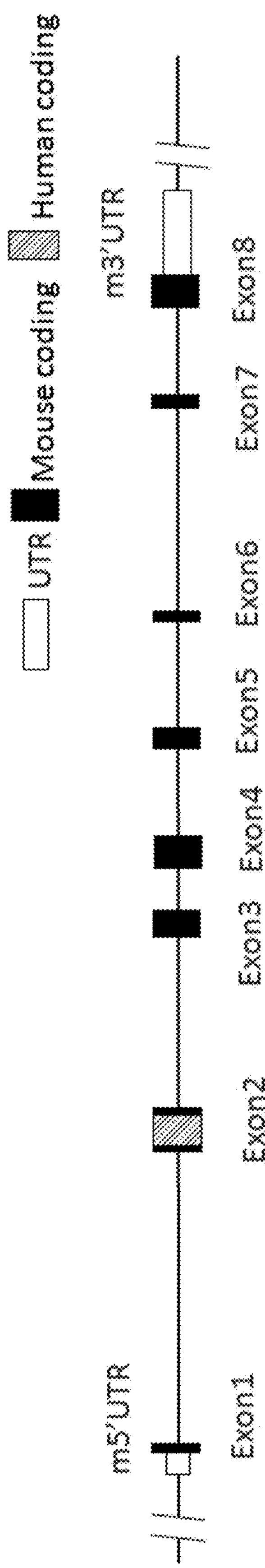
FIG. 2 is a schematic diagram showing humanized SIRPα gene.

A schematic diagram that compares the mouse SIRPα gene and the human SIRPα gene is shown in FIG. 1. The humanized SIRPα gene is shown in FIG. 2. A portion of the humanized SIRPα gene containing the human SIRPα sequence is shown in SEQ ID NO: 5:

```
                                       (SEQ ID NO: 5)
GAGCCACGGGGgaggaggagctgcaggtgattcagcctgacaagtccgtg
ttggttgcagctggagagacagccactctgcgctgcactgcgacctctct
gatccctgtggggcccatccagtggttcagaggagctggaccaggccggg
aattaatctacaatcaaaaagaaggccacttcccccgggtaacaactgtt
tcagacctcacaaagagaaacaacatggacttttccatccgcatcggtaa
catcaccccagcagatgccggcacctactactgtgtgaagttccggaaag
ggagccccgatgacgtggagtttaagtctggagcaGGAACAGAGGTCT
```

SEQ ID NO: 5 shows only the modified portion of DNA sequence, wherein the italicized underlined region is from human SIRPα.

The coding region sequence, mRNA sequence and the encoded amino acid sequence thereof of the modified humanized SIRPα are respectively set forth in SEQ ID NO: 6, SEQ ID NO: 7, and SEQ ID NO: 8.

Since the human SIRPα gene and the mouse SIRPα gene both have multiple transcript variants, the sequence design disclosed herein can be applied to other transcript variants. For example, the following mouse transcript variants and corresponding amino acid sequences of SIRPα can be used: NM_001177647.2→NP_001171118.1 (mRNA sequence set forth in SEQ ID NO: 9, corresponding to amino sequence set forth in SEQ ID NO: 10); NM_001291019.1→NP_001277948.1 (mRNA sequence set forth in SEQ ID NO: 11, corresponding to amino acid sequence set forth in SEQ ID NO: 12); NM_001291020.1→NP_001277949.1 (mRNA sequence set forth in SEQ ID NO: 13, corresponding to amino acid sequence shown in SEQ ID NO: 14); and NM_001291021.1→NP_001277950.1 (mRNA sequence shown in SEQ ID NO: 15, corresponding to amino acid sequence set forth in SEQ ID NO: 16).

Similarly, the following human SIRPα transcript variants and corresponding amino acid sequences can be used: NM_001040022.1→NP_001035111.1, NM_001040023.1→NP_001035112.1, NM_001330728.1→NP_001317657.1, XM_005260670.3→XP_005260727.1, XM_006723545.3→XP_006723608.1, and XM_011529173.2→XP_011527475.1.

The CDS sequences of humanized SIRPα gene based on the transcript variants are set forth in SEQ ID NOs: 17-20; the mRNA sequences are set forth in SEQ ID NOs: 21-24; and the amino acid sequences are set forth SEQ ID NOs: 25-28.

Example 2: Design and Construction of pClon-4G-SIRPα Vector

Figure 3:
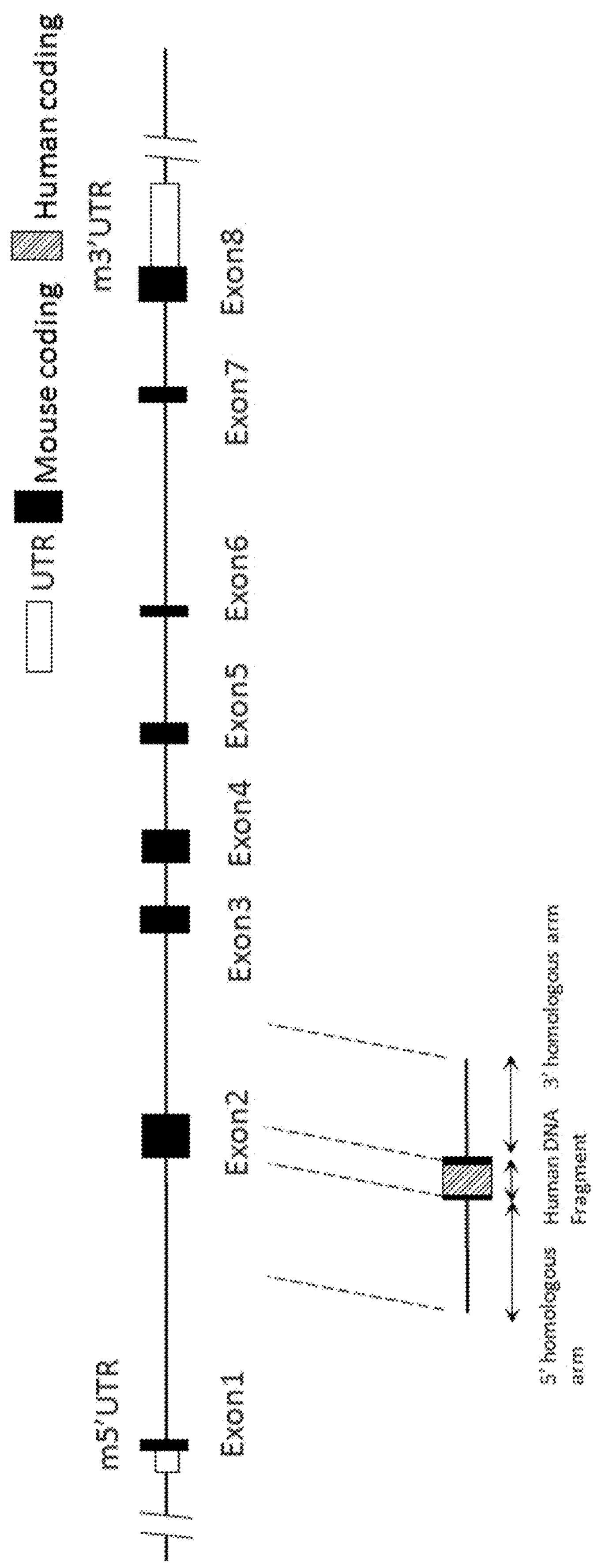
FIG. 3 is a schematic diagram showing gene targeting strategy.

A targeting strategy is shown in FIG. 3. As shown in FIG. 3, the 5' homologous arm, and the 3' homologous arm were designed, amplified and ligated to the corresponding sequence of human SIRPα. The 5' homologous arm (SEQ ID NO: 29) corresponds to nucleotides 129607346-129608914 of NC_000068.7. The 3' homologous arm (SEQ ID NO: 30) corresponds to nucleotides 129609239-129610638 of NC_000068.7, and the gene fragment from human SIRPα (SEQ ID NO: 31) corresponds to nucleotides 1915110-1915433 of NC_000020.11.

The table below shows the primers used to construct the 5' homologous arm (LR), the 3' homologous arm (RR), the human fragment (A), and their respective lengths.

TABLE 9

| Fragment | Length (bp) | Primer sequence |
|---|---|---|
| LR | 1620bp | F: 5'-tacctttaagaaggagatatacatgctcgagcacatctgccatgaaaattggatct-3' (SEQ ID NO: 32)<br>R: 5'-atcacctgcagctcctcctcccccgtggctcctgggaagaaagat-3' (SEQ ID NO: 33) |
| A | 364bp | F: 5'-tcttcccaggagccacgggggaggaggagctgcaggtgattcagc-3' (SEQ ID NO: 34)<br>R: 5'-agtacatagacctctgttcctgctccagacttaaactccacgtca-3' (SEQ ID NO: 35) |
| RR | 1453bp | F: 5'-tggagtttaagtctggagcaggaacagaggtctatgtactcggtaag-3' (SEQ ID NO: 36)<br>R: 5'-tcggttgttagcagccggatctcaggcggccgcgttcaggacagctcccactggtggg-3' (SEQ ID NO: 37) |

Mouse DNA (C57BL/6 background) or a BAC library was used as amplification template to produce the LR and RR fragments. Human DNA was used as amplification template to produce the A fragment. AIO kit was sued to ligate the three pieces into the pClon-4G plasmid to produce the pClon-4G-SIRPα vector.

Example 3: Verification of pClon-4G-SIRPα Vector

Figure 4:
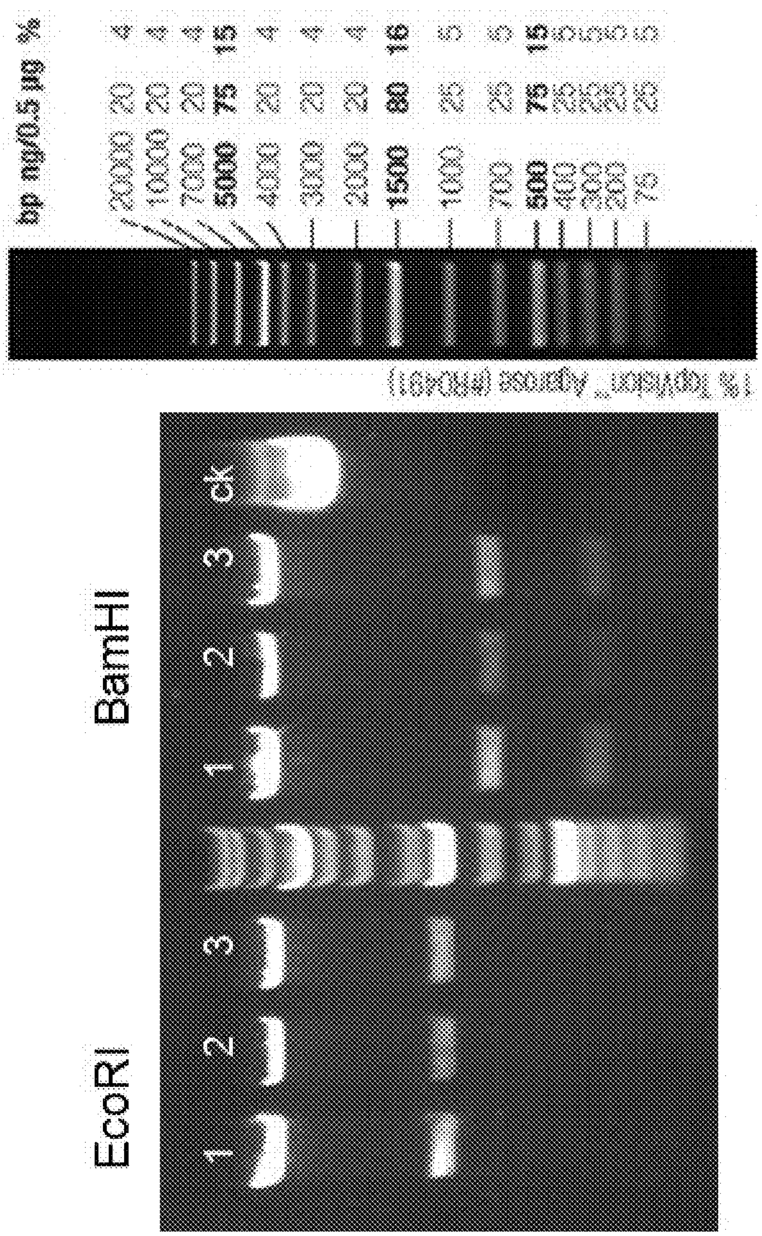
FIG. 4 shows the restriction enzymes digestion results of the plasmid pClon-4G-SIRPα (The numbers 1, 2, 3 indicate three different pClon-4G-SIRPα clones. ck indicates control plasmid without restriction enzyme digestion).

Three pClon-4G-SIRPα clones were randomly selected and tested by three sets of restriction enzymes. Among them, EcoRI digestion should produce 1371 bp+5439 bp fragments, BamHI digestion should produce 52 bp+321 bp+900 bp+5537 bp fragments. The results are shown in FIG. 4. Plasmids 1, 2, 3 all showed expected results. The sequences of plasmids 1 and 2 were further verified by sequencing. Plasmid 2 was used in the following experiments.

Example 4: sgRNA Design

The target sequence determines the targeting specificity of small guide RNA (sgRNA) and the efficiency of Cas9 cleavage at the target gene. Therefore, target sequence selection is important for sgRNA vector construction.

The 5'-terminal targeting sites (sgRNA1 to sgRNA10) and the 3'-terminal targeting sites (sgRNA11 to sgRNA21) were designed and synthesized. The 5'-terminal targeting sites and the 3'-terminal targeting sites are located on exon 2 of mouse SIRPα gene. The targeting site sequences on SIRPα are as follows:

```
sgRNA-1 target sequence (SEQ ID NO: 38):
5'-AGTTCCTTCCCCGTGGCTCCTGG-3'

sgRNA-2 target sequence (SEQ ID NO: 39):
5'-AGCCACGGGGAAGGAACTGAAGG-3'

sgRNA-3 target sequence (SEQ ID NO: 40):
5'-CACCTTCAGTTCCTTCCCCGTGG-3'

sgRNA-4 target sequence (SEQ ID NO: 41):
5'-AAATCAGTGTCTGTTGCTGCTGG-3'

sgRNA-5 target sequence (SEQ ID NO: 42):
5'-CACTTTGACCTCCTTGTTGCCGG-3'

sgRNA-6 target sequence (SEQ ID NO: 43):
5'-TTGACCTCCTTGTTGCCGGTGGG-3'

sgRNA-7 target sequence (SEQ ID NO: 44):
5'-GGGTCCCACCGGCAACAAGGAGG-3'

sgRNA-8 target sequence (SEQ ID NO: 45):
5'-TGTTGCCGGTGGGACCCATTAGG-3'

sgRNA-9 target sequence (SEQ ID NO: 46):
5'-ACTCCTCTGTACCACCTAATGGG-3'

sgRNA-10 target sequence (SEQ ID NO: 47):
5'-CTGTAGATCAACAGCCGGCTTGG-3'

sgRNA-11 target sequence (SEQ ID NO: 48):
5'-CGAAACTGTAGATCAACAGCCGG-3'

sgRNA-12 target sequence (SEQ ID NO: 49):
5'-CTGTTGATCTACAGTTTCGCAGG-3'

sgRNA-13 target sequence (SEQ ID NO: 50):
5'-TCTGAAACATTTCTAATTCGAGG-3'

sgRNA-14 target sequence (SEQ ID NO: 51):
5'-TACTACTAAGAGAAACAATATGG-3'

sgRNA-15 target sequence (SEQ ID NO: 52):
5'-CTGGGGTGACATTACTGATACGG-3'

sgRNA-16 target sequence (SEQ ID NO: 53):
5'-AATGTCACCCCAGCAGATGCTGG-3'

sgRNA-17 target sequence (SEQ ID NO: 54):
5'-GTAGATGCCAGCATCTGCTGGGG-3'

sgRNA-18 target sequence (SEQ ID NO: 55):
5'-CCTGACACAGAAATACAATCTGG-3'

sgRNA-19 target sequence (SEQ ID NO: 56):
5'-CACAGAAATACAATCTGGAGGGG-3 '
```

-continued

```
sgRNA-20 target sequence (SEQ ID NO: 57):
5'-ACAATCTGGAGGGGGAACAGAGG-3'

sgRNA-21 target sequence (SEQ ID NO: 58):
5'-GGAACAGAGGTCTATGTACTCGG-3'
```

Example 5: Testing sgRNA Activity

Figure 5:
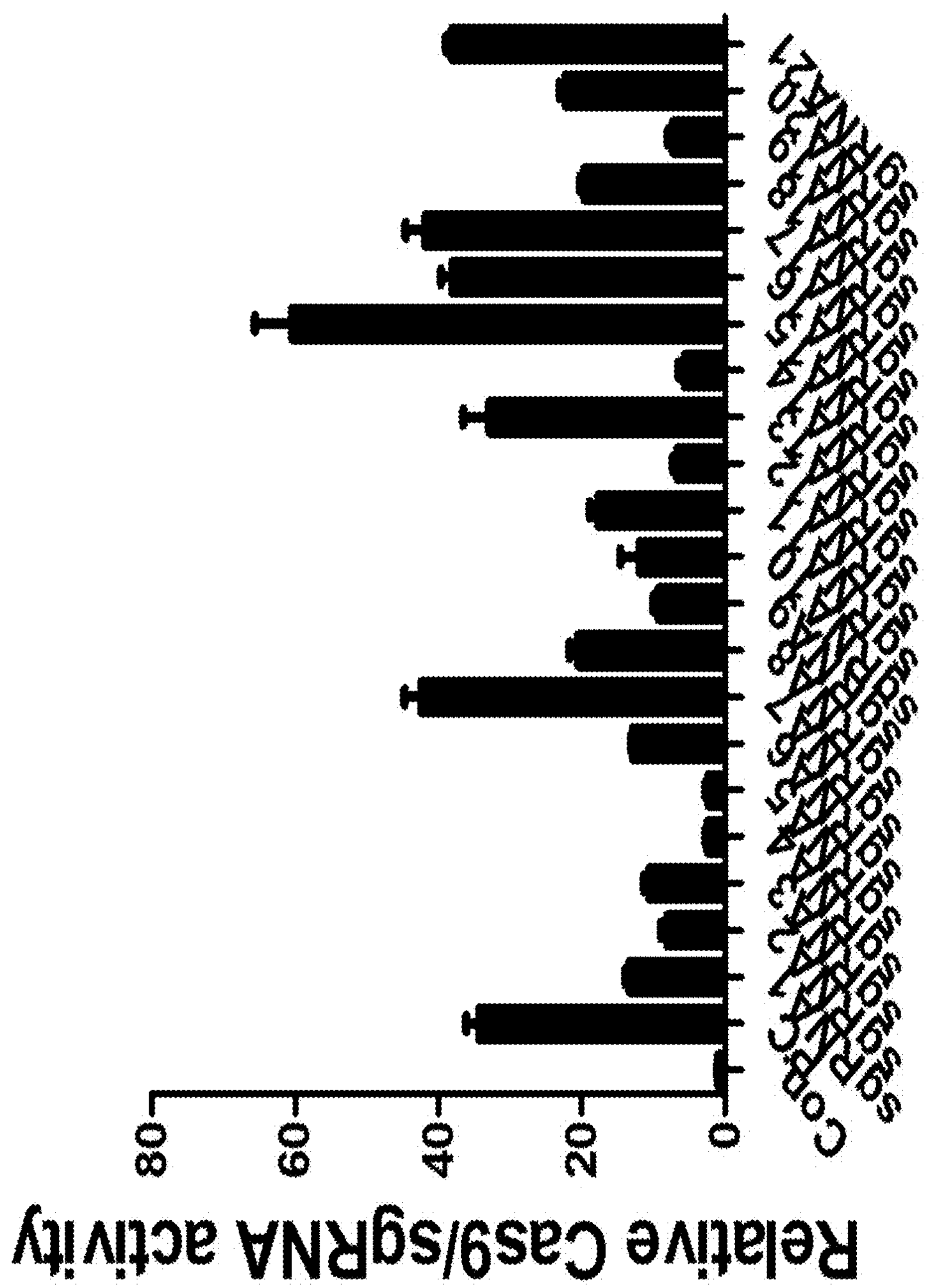
FIG. 5 is a graph showing activity testing results for sgRNA1-sgRNA21 (Con is a negative control; PC is a positive control).

The UCA kit was used to detect the activities of sgRNA (FIG. 5). The results show that the sgRNAs have different activities. Two of them sgRNA7 and sgRNA17 were selected for further experiments. Specifically, TAGG was added to the 5' end of the upstream sequence, and AAAC was added to the 5' end of the downstream sequence.

The synthesized sgRNA sequences based on sgRNA7 and sgRNA17 are listed below:

TABLE 10

| sgRNA7 and sgRNA17 sequences | |
|---|---|
| **sgRNA7** | |
| SEQ ID NO: 59 | Upstream: 5'-GTCCCACCGGCAACAAGG-3' |
| SEQ ID NO: 60 (adding TAGG to obtain a forward oligonucleotide sequence) | Forward: 5'-TAGGGTCCCACCGGCAACAAGG-3' |
| SEQ ID NO: 61 | Downstream: 5'-CCTTGTTGCCGGTGGGAC-3' |
| SEQ ID NO: 62 (complementary strand was added with AAAC to obtain a reverse oligonucleotide sequence) | Reverse: 5'-AAACCCTTGTTGCCGGTGGGAC-3' |
| **sgRNA17** | |
| SEQ ID NO: 63 | Upstream: 5'-TAGATGCCAGCATCTGCTG-3' |
| SEQ ID NO: 64 (adding TAGG to obtain a forward oligonucleotide sequence) | Forward: 5'-TAGGTAGATGCCAGCATCTGCTG-3' |
| SEQ ID NO: 65 | Downstream: 5'-CAGCAGATGCTGGCATCTA-3' |
| SEQ ID NO: 66 (complementary strand was added with AAAC to obtain a reverse oligonucleotide sequence) | Reverse: 5'-AAACCAGCAGATGCTGGCATCTA-3' |

Example 6: Constructing the pT7-sgRNA G2 Plasmid

Figure 6:
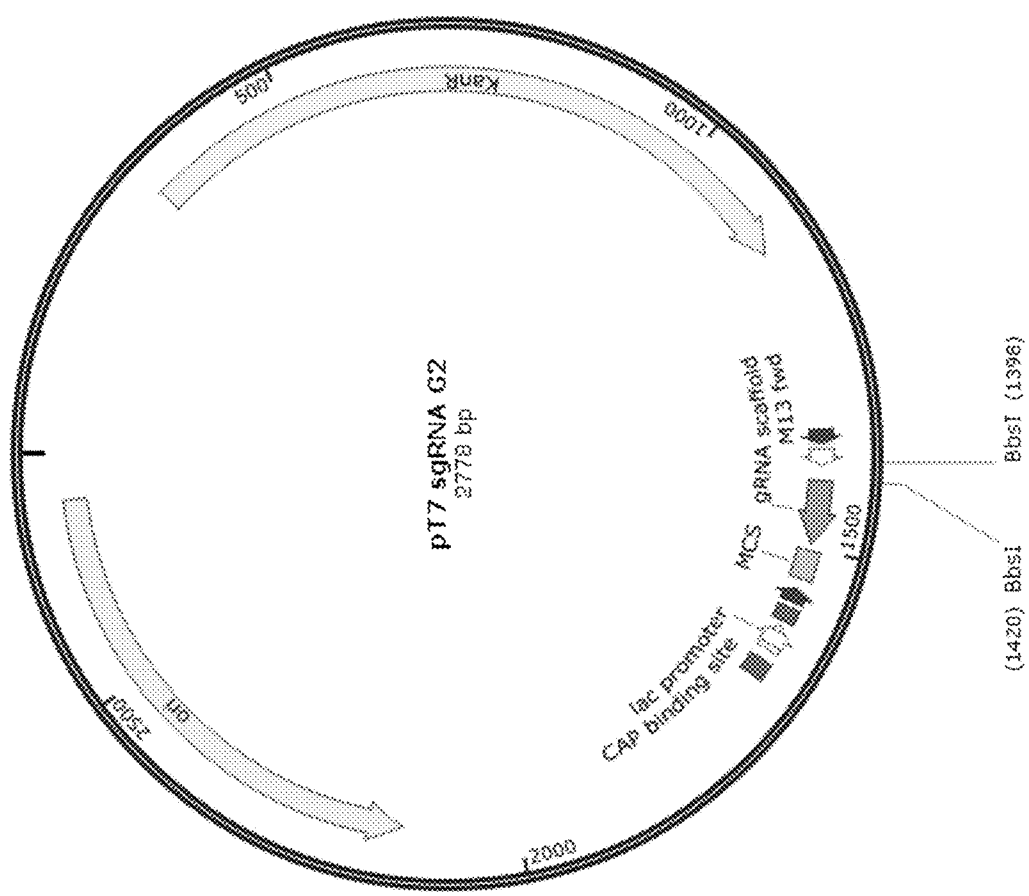
FIG. 6 is a schematic diagram showing the structure of pT7-sgRNA G2 plasmid.

A map of pT7-sgRNA G2 vector is shown in FIG. 6. Synthesized DNA fragment containing T7 promoter and the sgRNA scaffold was ligated to the backbone plasmid pHSG299 with restriction enzyme digestion (EcoRI and BamHI). The sequence of the plasmids was confirmed by sequencing.

The DNA fragment containing the T7 promoter and sgRNA scaffold is set forth in SEQ ID NO: 67:

```
GAATTCTAATACGACTCACTATAGGGGGTCTTCGAGAAGACCTGTTTTAG

AGCTAGAAATAGCAAGTTAAAATAAGGCTAGTCCGTTATCAACTTGAAAA

AGTGGCACCGAGTCGGTGCTTTTAAAGGATCC
```

Example 7: Constructing Recombinant Expression Vectors pT7-sgRNA-S7 and pT7-sgRNA-S17

After annealing the forward and reverse oligonucleotides in Example 5, the oligonucleotides were ligated to pT7-sgRNA plasmids to produce the expression vectors pT7-sgRNA-S7 and pT7-sgRNA-S17. The ligation reaction is set up as follows:

TABLE 11

| The ligation reaction mix (10 μL) | |
|---|---|
| Double stranded fragment | 1 μL (0.5 μM) |
| pT7-sgRNA G2 vector | 1 μL (10 ng) |
| T4 DNA Ligase | 1 μL (5 U) |
| 10 × T4 DNA Ligase buffer | 1 μL |
| 50% PEG4000 | 1 μL |
| $H_2O$ | Add to 10 μL |

The ligation reaction was carried out at room temperature for 10 to 30 minutes. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Randomly selected clones were sequenced to verify their sequences. The vectors pT7-sgRNA-S7 and pT7-sgRNA-S17 with correct sequences were selected for subsequent experiments.

Example 8: Microinjection and Embryo Transfer Using C57BL/6 Mice

The pre-mixed Cas9 mRNA, pClon-4G-SIRPα plasmid and in vitro transcription products of pT7-sgRNA-S7, pT7-sgRNA-S17 plasmids were injected into the cytoplasm or nucleus of mouse fertilized eggs (C57BL/6 background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mouse population was further expanded by cross-mating and self-mating to establish stable mouse lines. The humanized mouse was named as B-hSIRPα.

Example 9: Verification of Genetically Modified Humanized Mouse Models

1. Genotype Determination for F0 Generation Mice

PCR analysis was performed using mouse tail genomic DNA of F0 generation B-hSIRPα mice. The primers are shown below with their relative genomic locations.

```
5' end primers:
Upstream: L-GT-F (SEQ ID NO: 68), left side of 5'
homologous arm:
5'-CATCAAGCCTGTTCCCTCCTTGTGT-3'

Downstream: L-GT-R (SEQ ID NO: 69), in exon 2:
5'-CTTAAACTCCACGTCATCGGGGCTC-3'

3' end primers:
Upstream: R-GT-F (SEQ ID NO: 70), in exon 2:
5'-TCAAAAAGAAGGCCACTTCCCCCGGG-3'

Downstream: R-GT-R (SEQ ID NO: 71), right side of
3' homologous arm:
5'-CAAGCTGTAGAGACAGATGGGCAGG-3'
```

If the desired human sequence was inserted into the correct positions in the genome, PCR experiments using the primers above should generate only one band. The 5' end PCR experiment should produce a band at about 2,047 bp, and the 3' end PCR experiment should produce a band at about 1,836 bp.

TABLE 12

| The PCR reaction mix (20 μL) | |
|---|---|
| 2 × PCR buffer | 10 μL |
| dNTP (2 mM) | 4 μL |
| Upstream primer (10 μM) | 0.6 μL |
| Downstream primer (10 μM) | 0.6 μL |
| Mouse tail genomic DNA | 100 ng |
| KOD-FX (1 U/μL) | 0.4 μL |
| $H_2O$ | Add to 20 μL |

TABLE 13

| The PCR reaction conditions | | |
|---|---|---|
| Temperature | Time | Cycles |
| 94° C. | 5 min | 1 |
| 94° C. | 30 sec | 15 |
| 67° C. (−0.7° C./cycle) | 30 sec | |
| 68° C. | 1 kb/min | |
| 94° C. | 30 sec | 25 |
| 56° C. | 30 sec | |
| 68° C. | 1 kb/min | |
| 68° C. | 10 min | 1 |
| 4° C. | 10 min | 1 |

Figures 7A, 7B:
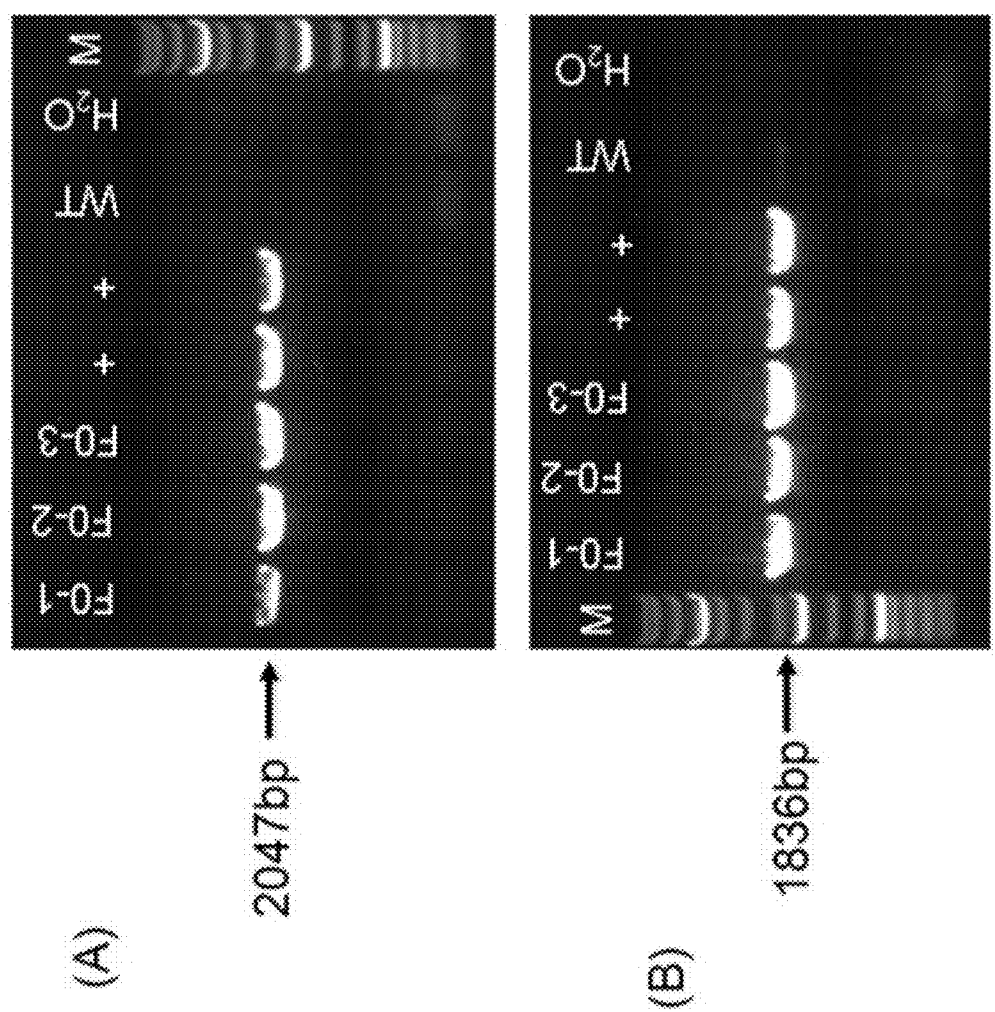
FIGS. 7A-7B show PCR identification results of samples collected from tails of F0 generation mice (WT is wildtype; + is positive control. Mice labeled with F0-1, F0-2, and F0-3 are positive).

Results are shown in FIGS. 7A-7B. F0-1, F0-2, and F0-3 had PCR products with the correct size and thus the human sequences were correctly inserted into the mouse genome.

2. Genotype Determination for F1 Generation Mice

F1 generation mice were obtained by cross-mating F0 generation mice with wildtype mice in the same background. PCR experiments were performed using mouse tail genomic DNA from F1 mice. The PCR primers, setup, and conditions were the same as those used in genotyping the F0 generation mice.

Figures 8A, 8B:
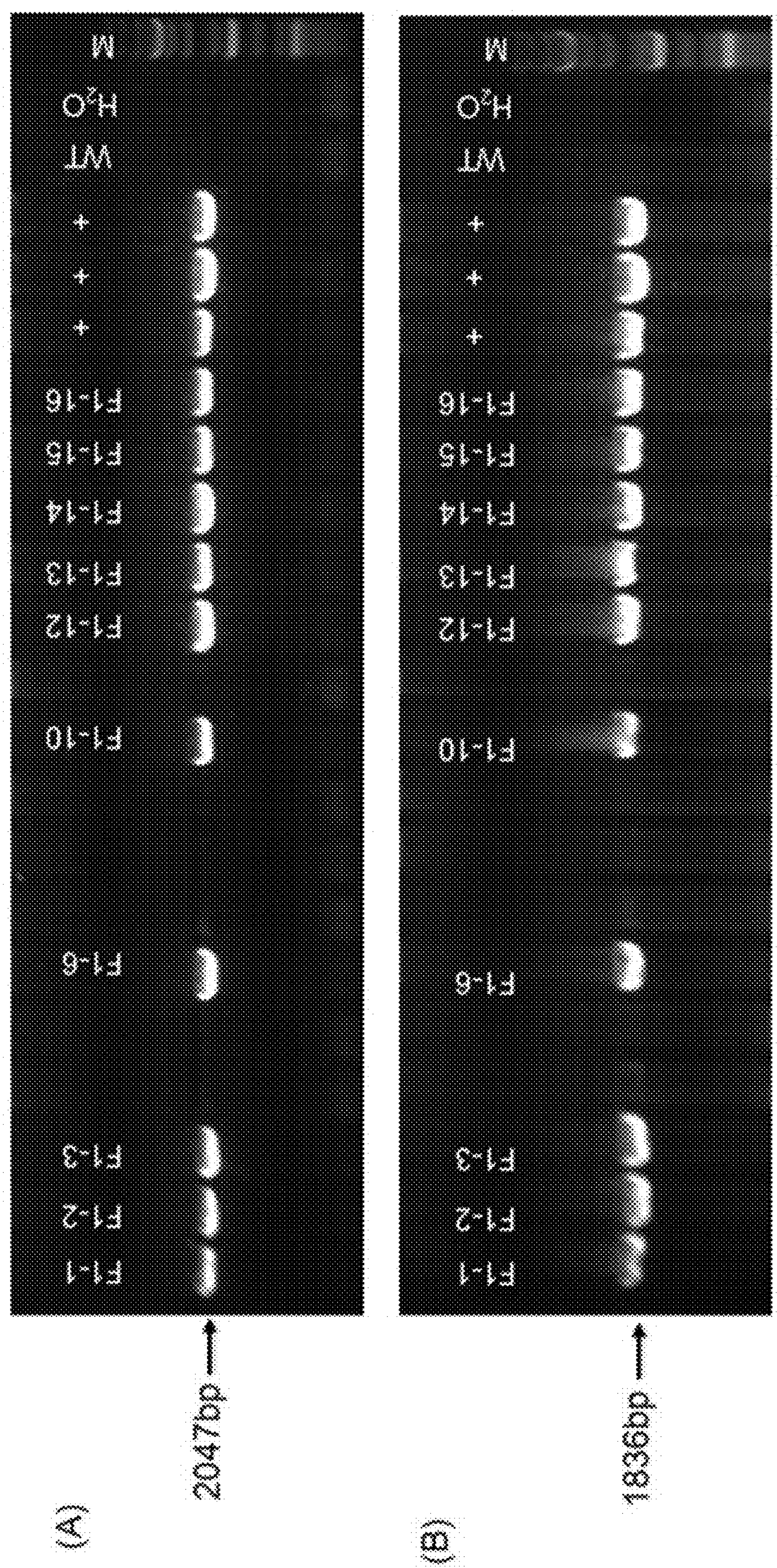
FIGS. 8A-8B show PCR identification result of samples collected from tails of F1 generation mice (WT is wildtype; Mice labeled with F1-1, F1-2, F1-3, F1-6, F1-10, F1-12, F1-13, F1-14, F1-15, F1-16 are positive).

Results are shown in FIGS. 8A-8B. Ten F1 generation mice F1-1, F1-2, F1-3, F1-6, F1-10, F1-12, F1-13, F1-14, F1-15, and F1-16 had PCR products with the correct size and thus the human sequences were correctly inserted into the mouse genome.

Furthermore, Southern blot was used on the ten mice to confirm that there was no random insertion. Genomic DNA was extracted from mouse tail, digested with AseI restriction enzyme, blotted, and hybridized with probes P1 and P2. P1 and P2 are located on 5' homologous arm and on the right side of the 3' homologous arm. The primers for synthesizing P1 and P2 are as follows:

```
P1-F:
                                    (SEQ ID NO: 72)
5'-GCAGGACAGTGAGCAACTGATGACA-3'

P1-R:
                                    (SEQ ID NO: 73)
5'-GCACAGTGGCCTAACTACCTTCCTG-3'

P2-F:
                                    (SEQ ID NO: 74)
5'-GGTAGTGCCCATGAAGCTGGTACTC-3'

P2-R:
                                    (SEQ ID NO: 75)
5'-GGCCACCACATTATGGCTTTCTCCT-3'
```

The hybridization result for a humanized SIRPα mouse should generate a 2.8 kb and a 5.2 kb band, while the wildtype mouse should have a 8.0 kb band.

Figures 9A, 9B:
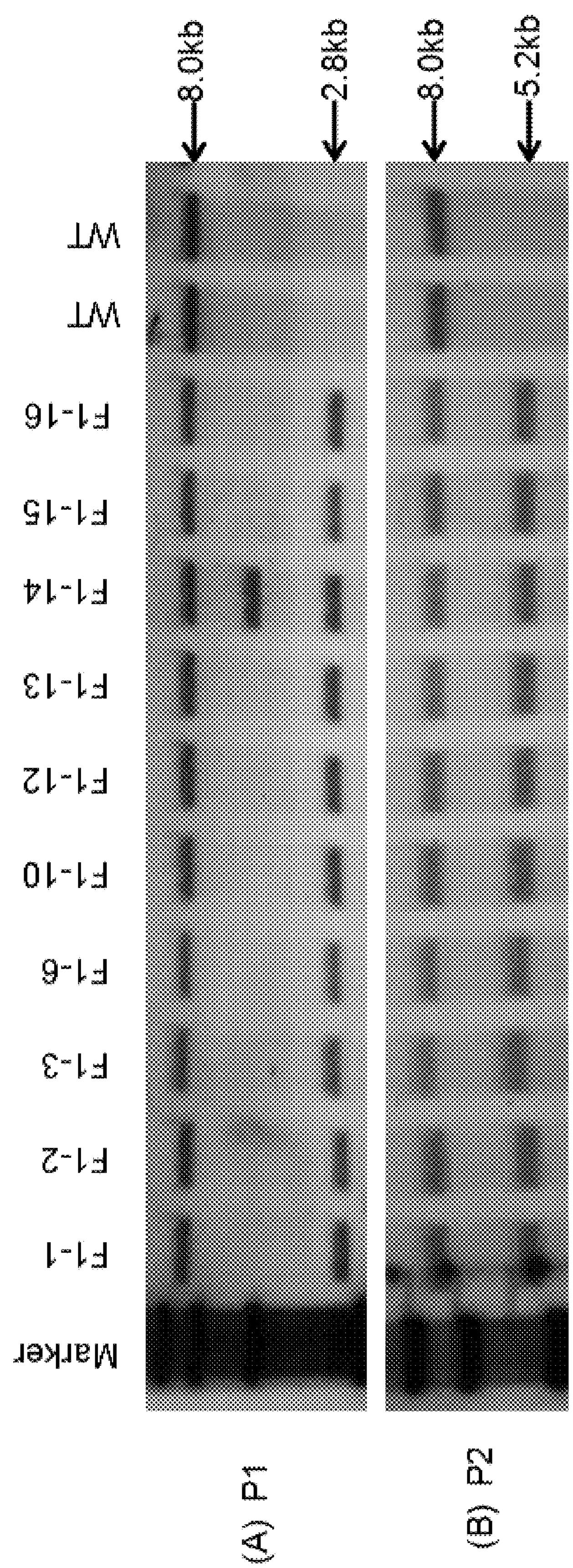
FIGS. 9A-9B show Southern blot results for F1 generation mice (WT is wildtype; the mice labeled with F1-1, F1-2, F1-3, F1-6, F1-10, F1-12, F1-13, F1-15, and F1-16 did not have random insertion).

As shown in FIG. 9, F1-1, F1-2, F1-3, F1-6, F1-10, F1-12, F1-13, F1-15, and F1-16 had no random insertion. F1-14 may have random insertions.

These results show that the methods described herein can be used to generate humanized SIRPα mice with stable and inheritable genetic modifications.

3. Expression Analysis in Humanized Mice

Homozygous humanized SIRPα mice (B-hSIRPα) were obtained by cross-mating F1 generation mice. A humanized homozygous B-hSIRPα mouse was selected (4-6 weeks old) for this experiment. Two wildtype mice in the same background (C57BL/6) were used as controls.

7.5 μg of mouse anti-CD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS and RT-PCR.

Figures 10A, 10B, 10C, 10D, 10E, 10F:
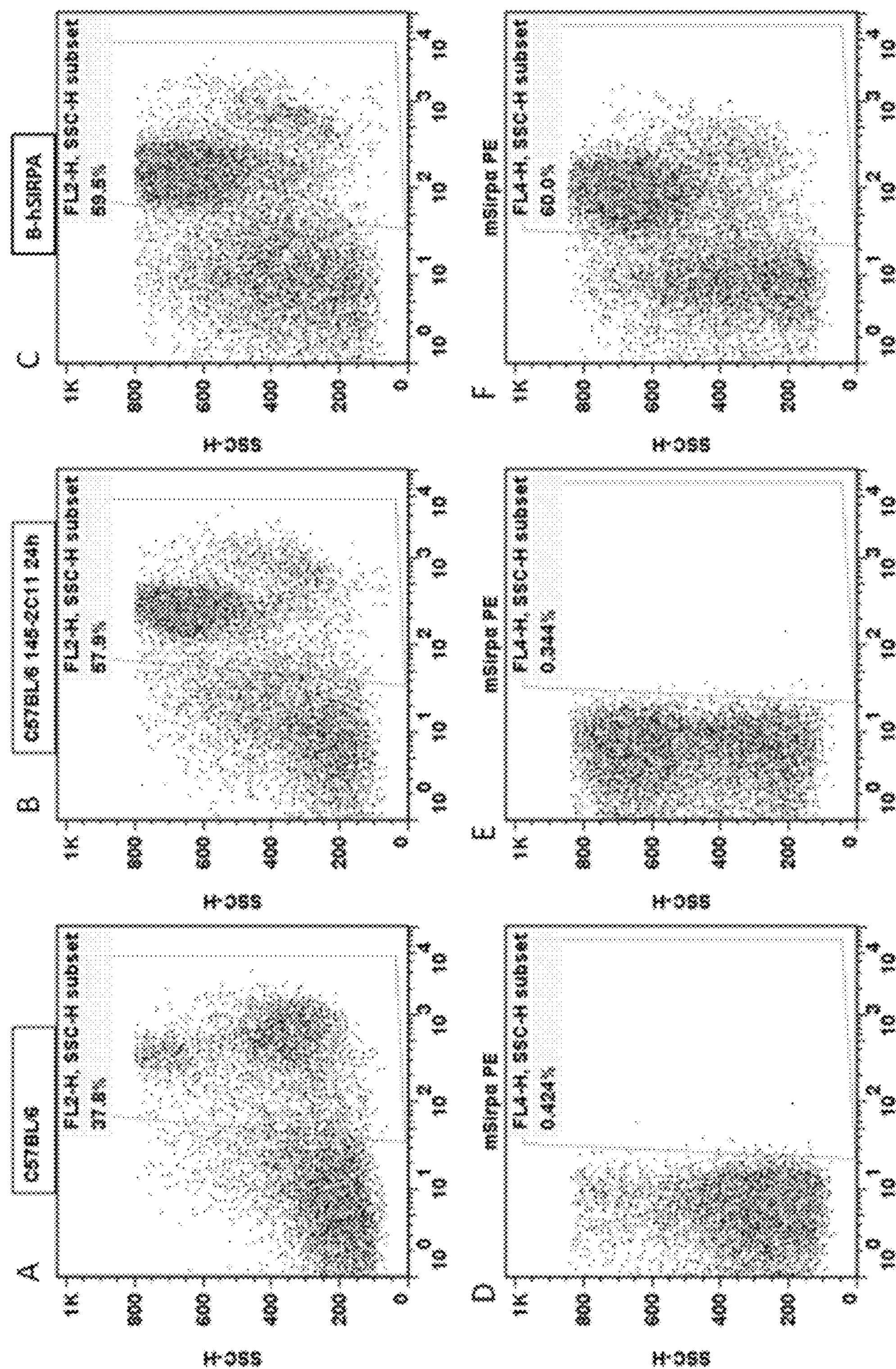
FIGS. 10A-10F are flow cytometry results of wildtype C57BL/6 mice (FIGS. 10A, 10B, 10D, and 10E) and homozygous humanized SIRPα mice (B-hSIRPα) (FIGS. 10C, 10F). Anti-CD3 antibody was used to activate spleen cells in FIGS. 10B, 10C, 10E, 10F. Flow cytometry analysis was performed with antibody against mouse SIRPα (mSIRPα PE) (FIGS. 10A-10C) and antibody against human SIRPα (hSIRPα APC) (FIGS. 10D-10F). In the control groups, no spleen cells stained with hSIRPα APC were observed in wildtype mice (FIGS. 10D and 10E); in humanized SIRPα groups, spleen cells stained with hSIRPα APC were observed in humanized SIRPα mice (FIG. 10F).

FACS: Flow cytometry was performed with wildtype C57BL/6 mice (FIGS. 10A, 10B, 10D, and 10E) and humanized SIRPα mice (FIGS. 10C, 10F). Anti-CD3 antibody was used to activate spleen cells in FIGS. 10B, 10C, 10E, 10F. Flow cytometry was performed with antibody against mouse SIRPα (mSIRPα PE) (FIGS. 10A-10C) and antibody against human SIRPα (hSIRPα APC) (FIGS. 10D-10E). In the control groups, cells stained with mSIRPα PE were observed in wildtype mice (FIGS. 10A-10B); and antibody against mouse SIRPα cross reacted with humanized SIRPα in homozygous B-hSIRPα mice (FIG. 10C). Cells stained with hSIRPα APC were observed only in B-hSIRPα mice (FIG. 10F), but not in wildtype C47BL/6 mice with or without anti-CD3 antibody activation.

RT-PCR: RT-PCR experiments were performed to confirm the genetic makeup of humanized hSIRPα mice (B-hSIRPα). mRNA was extracted from spleens of B-hSIRPα mice and reverse-transcribed into cDNA. The primers that were used to target human hSIRPα (hSIRPα) mRNA sequence and mouse hSIRPα (mSIRPα) mRNA sequence are as follows:

```
mSirpa RT-PCR F2:
                                    (SEQ ID NO: 76)
5'-TTGCTGCTGGGGATTCGAC-3'

mSirpa RT-PCR R2:
                                    (SEQ ID NO: 77)
5'-CTGCTGGGGTGACATTACTGAT-3'

hSIRPα RT-PCR F1:
                                    (SEQ ID NO: 78)
5'-CCTGACAAGTCCGTGTTGG-3'

hSIRPα RT-PCR R1:
                                    (SEQ ID NO: 79)
5'-CTCCTCTGAACCACTGGATGG-3'
```

The primers targeting mouse Sirpa sequence should generate a PCR band of about 210 bp. The primers targeting human SIRPα sequence should generate a PCR band of about 100 bp.

Figure 11:
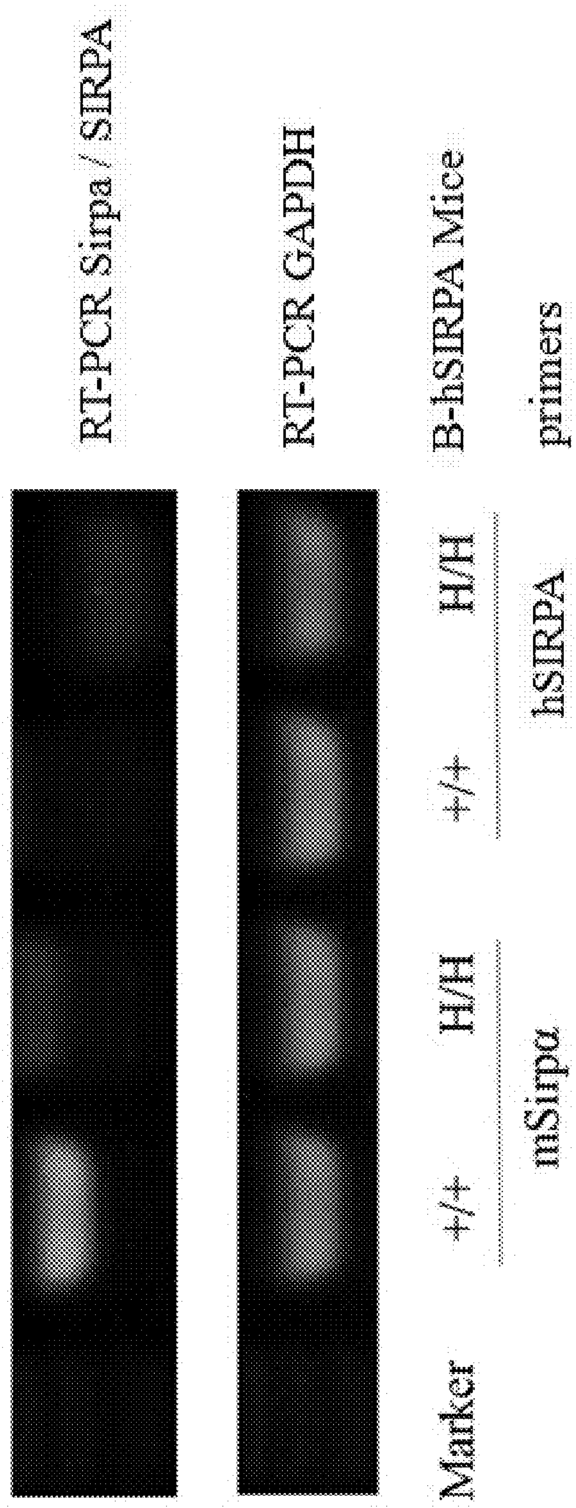
FIG. 11 shows results from RT-PCR experiments (+/+ indicates wildtype C57BL/6 mice; H/H indicates homozygous humanized SIRPα mice; and GAPDH was used as a control).

PCR was performed. GAPDH was used as an internal control. Results are shown in FIG. 11. Mice Sirpa mRNA was detected in activated spleen cells of wildtype C57BL/6 mice. Human SIRPα mRNA was detected in homozygous B-hSIRPα mice.

Example 10: SIRPα Knockout Mice

Since the cleavage of Cas9 results in DNA double strand break, and the homologous recombination repair may result in insertion/deletion mutations, it is possible to obtain SIRPα knockout mice when preparing the humanized SIRPα. A pair of primers was thus designed with one primer on the left side of the 5' target site and the other primer on the right side of the 3' target site. These primers are shown below:

```
KO-F:
                                    (SEQ ID NO: 80)
5'-GTCTTGAGTTACAGGCTCATGTGGGG-3'

KO-R:
                                    (SEQ ID NO: 81)
5'-CCCATTATACCTGCTGCGAGCCAC-3'
```

Figure 12:
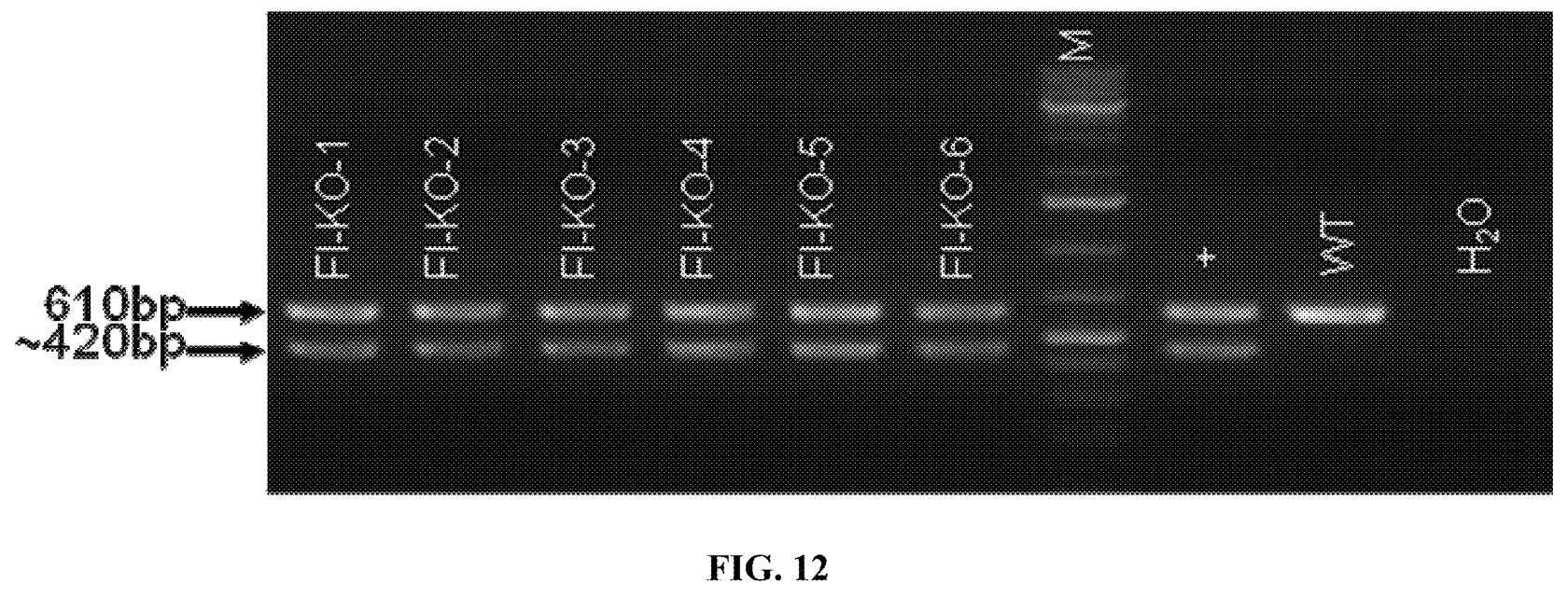

This pair of primers should yield one PCR band at about 610 bp for wildtype mice, a band at about 420 for homozygous SIRPα knockout mice, and two bands for heterozygous mice. Results are shown in FIG. 12. The 6 tested mice were all heterozygous SIRPα knockout mice.

The PCR reaction systems and conditions are listed in Table 14 and Table 15 below.

TABLE 14

| | |
|---|---|
| 2 × PCR buffer | 10 μL |
| dNTP (2 mM) | 4 μL |
| Upstream primer (0.2 μM) | 0.6 μL |
| Downstream primer (0.2 μM) | 0.6 μL |
| Genomic DNA from mouse tail | 100 ng |
| KOD-FX (1 U/μL) | 0.4 μL |
| $ddH_2O$ | Add to 20 μL |

TABLE 15

| Temperature | Duration | Cycles |
|---|---|---|
| 94° C. | 5 min | 1 |
| 98° C. | 10 sec | 35 |
| 62° C. | 30 sec | |
| 68° C. | 1 kb/min | |
| 68° C. | 10 min | 1 |
| 4° C. | 10 min | 1 |

Example 11: Making CD47 Humanized Mice sgRNAs that target the 5'-terminal targeting sites (sgRNA6-CD47) and the 3'-terminal targeting sites (sgRNA9-CD47) of mouse CD47 were designed and synthesized. The synthesized sgRNA sequences are listed in the following table:

TABLE 16

| | |
|---|---|
| **sgRNA6-CD47 sequences** | |
| SEQ ID NO: 95 | Upstream: 5'-taggcatgaagtgaactcta--3' |
| SEQ ID NO: 96 | Downstream: 5'-aaactagagttcacttcatg-3' |
| **sgRNA9-CD47 sequences** | |
| SEQ ID NO: 97 | Upstream: 5'-taggataagcgcgatgcca-3' |
| SEQ ID NO: 98 | Downstream: 5'-aaactggcatcgcgcttat-3' |

The plasmid backbone was obtained from Takara (Catalog No. 3299). The DNA fragment containing T7 promoter and sgRNA scaffold was synthesized, and linked to the backbone vector by restriction enzyme digestion (EcoRI and BamHI) and ligation.

After annealing, the sgRNA oligonucleotides were ligated to pT7-sgRNA plasmids (linearized with BbsI) to produce the expression vectors pT7-CD47-6 and pT7-CD47-9. Clones were randomly selected and sequenced to verify their sequences. The vectors with correct sequences were selected for subsequent experiments.

Genomic DNA 12533-12838 on exon 2 of mouse CD47 gene (NCBI accession no. NC_000082.6) was replaced with the corresponding portion of human CD47 gene, producing humanized mouse with the modified CD47 sequence as follows (the chimeric portion; SEQ ID NO: 99):

tatatgcagattgtaatgaaatattttgtgtatgtattccaggttcagc tcaactactgttt*aataaaacaaaatctgtagaattcacgttttgtaatg*

*acactgtcgtcattccatgctttgttactaatatggaggcacaaaacact*

*actgaagtatacgtaaagtggaaatttaaaggaagagatatCtacacctt*

*tgatggagctctaaacaagtccactgtccccactgactttagtagtgcaa*

*aaattgaagtctcacaattactaaaaggagatgcctctttgaagatggat*

*aagagtgatgctgtctcacacacaggaaactacacttgtgaagtaacaga*

*attaaccagagaaggtgaaacgatc*atagagctgaaaaaccgcacgggta

-continued agtgacacagtttgcctgttttgaaacgtgtgttgagatatggttgccac tgtgggagtgctgtaaggtggaaccttgcagaagtc SEQ ID NO: 99 shows only the modified portion of DNA sequence, wherein the italicized underlined region is from human CD47. The capital letter indicates a point mutation. The mRNA sequence of humanized CD47 gene is set forth in SEQ ID NO: 100, corresponding to the amino acid sequence as shown in SEQ ID NO: 101. The same methods described herein can be used to generate other variants of humanized versions of mouse CD47 gene and the transgenic mice containing these variants.

The pre-mixed Cas9 mRNA, pClon-4G-CD47 plasmid and in vitro transcription products of pT7-CD47-6, pT7-CD47-9 plasmids were injected into the cytoplasm or nucleus of mouse fertilized eggs (C57BL/6 background or BALB/c background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mouse population was further expanded by cross-mating with the same background or self-mating with each other to establish stable mouse lines.

The humanized mouse in C57BL/6 background was named as B-hCD47(C57BL/6), and the humanized mouse in BALB/c background was named as B-hCD47(BALB/c).

Further binding experiments showed that human CD47 or humanized CD47 proteins have a relatively weak binding affinity with mouse SIRPα in B-hCD47(C57BL/6) mice. In contrast, human CD47 or humanized CD47 proteins can bind to mouse SIRPα in B-hCD47(BALB/c) mice, and the binding affinity is similar to the binding affinity between mouse SIRPα and mouse CD47 protein. The binding between mouse and human CD47 proteins and SIRPα proteins in different mouse background was evaluated and described in Example 16.

Example 12: Mice with Two or More Humanized Genes

Mice containing the humanized SIRPα gene (e.g., animal model with humanized SIRPα prepared using the methods as described in the present disclosure) can also be used to prepare an animal model with double-humanized or multi-humanized genes. For example, in Example 8, the embryonic stem cell used in the microinjection and embryo transfer process can be selected from the embryos of other genetically modified mice to obtain double- or multiple-gene modified mouse models. The fertilized eggs of B-hSIRPα mice can also be further genetically engineered to produce mouse lines with one or more humanized or otherwise genetically modified mouse models. In addition, the humanized SIRPα homozygote or heterozygote animal can be mated with other genetically modified homozygous or heterozygous animal models (or through IVF), and the progeny can be then screened. According to the Mendel's laws, there is a chance to obtain the double-gene or multiple-gene modified heterozygous animal models, and then the obtained heterozygous can be mated with each other to finally obtain the double-gene or multiple-gene modified homozygotes.

In the case of generating double humanized CD47/SIRPα mice, since the mouse CD47 gene and SIRPα gene are located on different chromosomes, the double humanized CD47/SIRPα mouse model was obtained by crossing the CD47 humanized mice with SIRPα humanized mice.

Figures 13A, 13B:
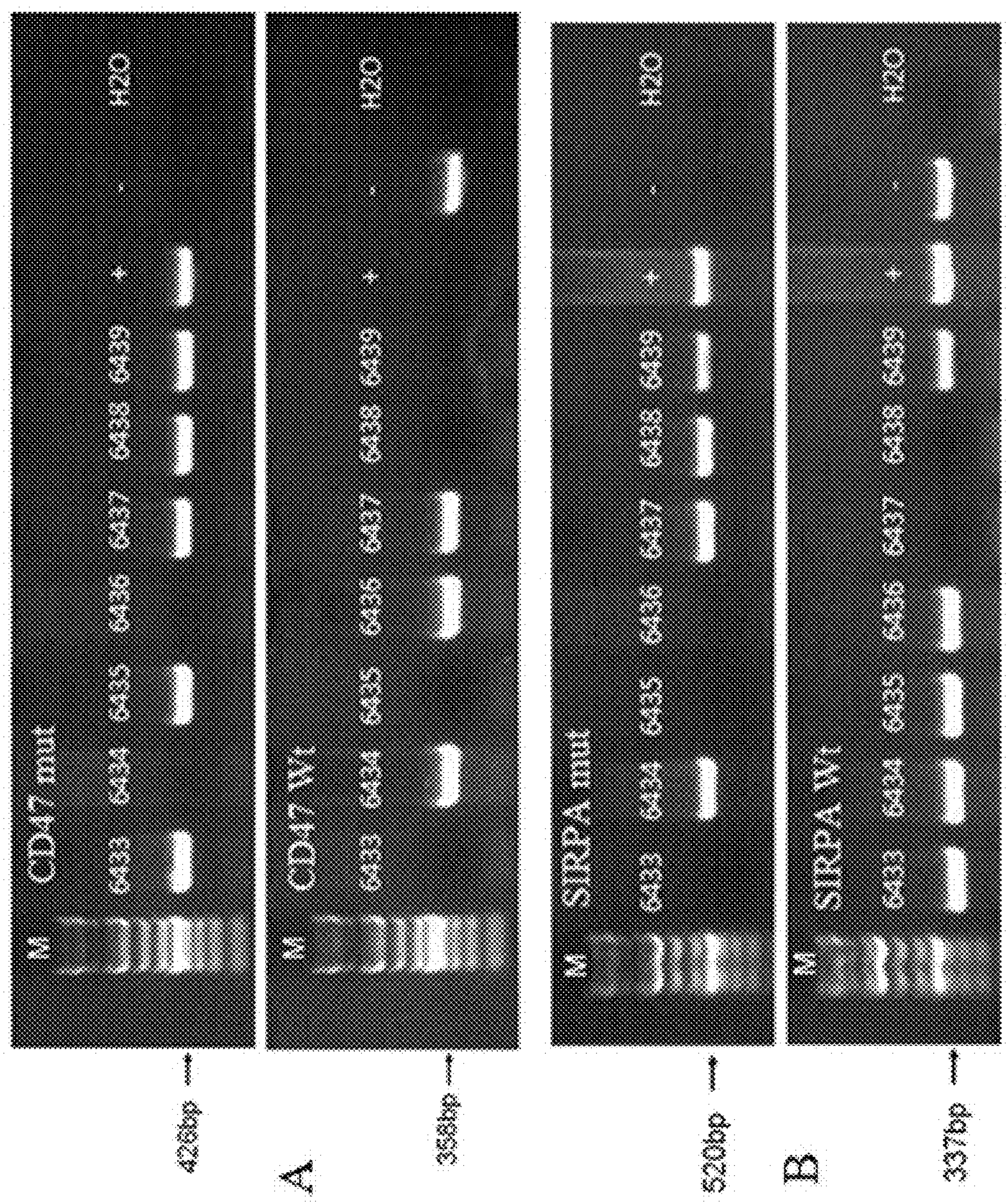
FIG. 13A shows PCR results using primers targeting CD47 gene (+ is a control from a homozygous humanized CD47 mouse. − is wildtype). Results show that mice numbered 6433, 6435, 6438, and 6439 are homozygous for humanized CD47. The mice numbered 6434 and 6436 have wildtype CD47 genes. The mouse number 6437 is a heterozygous humanized CD47 mouse.
FIG. 13B shows PCR results using primers targeting SIRPα gene (+ is a control from a heterozygous humanized SIRPα mouse. − is wildtype). Results show that mice numbered 6437 and 6438 are homozygous for humanized SIRPα. The mice numbered 6433, 6435, and 6436 have wildtype SIRPα genes. The mice number 6434 and 6439 are heterozygous humanized SIRPα mice.

PCR analysis was performed on the mouse tail genomic DNA of double humanized CD47/SIRPα mice using four pairs of primers. The specific sequences and product lengths are shown in the table below. The reaction system and reaction conditions are shown in Table 18 and Table 19. The results for a number of humanized CD47/SIRPα mice are shown in FIG. 13. In FIG. 13A, the mice numbered 6433, 6435, 6438, and 6439 are homozygous humanized CD47 mice, and the mouse numbered 6437 is heterozygous for humanized CD47; in FIG. 13B, the mice numbered 6437 and 6438 are homozygous humanized SIRPα mice, and the mice numbered 6434 and 6439 are heterozygous humanized SIRPα mice. Together, the results in FIG. 13A and FIG. 13B show that the mouse numbered 6438 is homozygous double humanized mice ($CD47^{H/H}$/$SIRP\alpha^{H/H}$); the mouse numbered 6439 is a double humanized mouse that is homozygous for the humanized CD47 gene and heterozygous for the SIRPα gene ($CD47^{H/H}$/$SIRP\alpha^{H/+}$); and the mouse numbered 6437 is a double humanized mouse that is heterozygous for the humanized CD47 gene and homozygous for humanized SIRPα gene ($CD47^{H/+}$/$SIRPA^{H/H}$).

TABLE 17

Primer sequences

| Primer | Sequence | Product length |
|---|---|---|
| CD47 WT | F: 5'-GGTAAATTTATCCCCAAGATGCATGGTA-3' (SEQ ID NO: 82)<br>R: 5'-ACAAACATTTCTTCGGTGCTTTGCG-3' (SEQ ID NO: 83) | WT: 358bp |
| CD47 MUT | F: 5'-GGTAAATTTATCCCCAAGATGCATGGTA-3' (SEQ ID NO: 82)<br>R: 5'-TGGGGACAGTGGACTTGTTTAGAGC-3' (SEQ ID NO: 84) | Mut: 426bp |
| SIRPα MUT | F: 5'-AGCTATGTGGCTTAGCACTCTGTGC-3' (SEQ ID NO: 85)<br>R: 5'-CTTAAACTCCACGTCATCGGGGCTC-3' (SEQ ID NO: 69) | Mut: 520bp |
| SIRPα WT | F: 5'-GTCTTGAGTTACAGGCTCATGTGGGG-3' (SEQ ID NO: 80)<br>R: 5'-CGAGGAACGTATTCTCCTGCGAAAC-3' (SEQ ID NO: 86) | WT: 337bp |

TABLE 18

PCR reaction system

| Composition | Volume |
|---|---|
| 2 × Master Mix | 10 μL |
| Upstream primer (10 μM) | 0.5 μL |
| Downstream primer (10 μM) | 0.5 μL |
| Mouse tail genomic DNA (100-200 ng/20 ml) | 2 μL |
| $ddH_2O$ | Add to 20 μL |

TABLE 19

PCR amplification reaction condition

| Temperature | Time | Cycles |
|---|---|---|
| 95° C. | 5 min | 1 |
| 95° C. | 30 sec | 30 |
| 59° C. | 30 sec | |
| 72° C. | 30 sec | |
| 72° C. | 10 min | 1 |
| 4° C. | 10 min | 1 |

Protein expression in the double humanized CD47/SIRPα mice was further examined. A homozygous double humanized SIRPA/SIRPα mice (4-6 weeks old) was selected for the study. Two wildtype C57BL/6 mice were selected as controls.

7.5 μg of mouse anti-CD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS and RT-PCR.

Figures 14A, 14B, 14C, 14D, 14E, 14F:
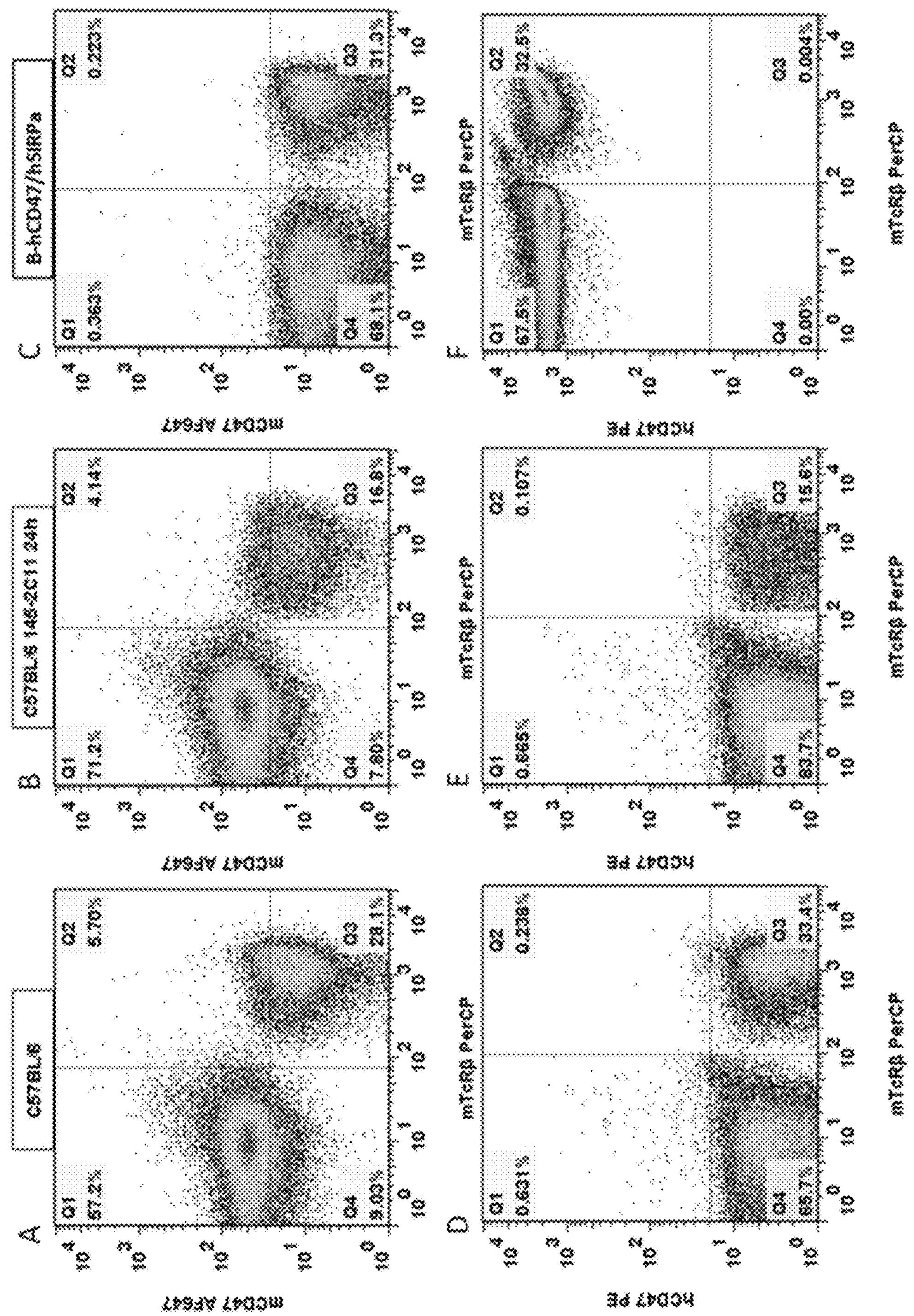
FIGS. 14A-14F are flow cytometry results of wildtype C57BL/6 mice (FIGS. 14A, 14B, 14D, and 14E) and double humanized CD47/SIRPα homozygous mice (FIGS. 14C, 14F). Anti-CD3 antibody was used to activate spleen cells in FIGS. 14B, 14C, 14E and 14F. Flow cytometry analysis was performed with (1) antibody against mouse CD47 (mCD47 Alexa Fluor 647, AF647) and antibody against mouse TcRβ (mTcRβ PerCP) (FIGS. 14A-14C); (2) antibody against human CD47 (hCD47 PE) and antibody against mouse TcRGβ (mTcRβ PerCP) (FIGS. 14D-14F). In the control groups, no spleen cells stained with hCD47 PE were observed in wildtype mice (FIGS. 14D and 14E); in double humanized CD47/SIRPα groups, spleen cells stained with hCD47 PE were observed (FIG. 14F).
Figures 15A, 15B, 15C, 15D, 15E, 15F:
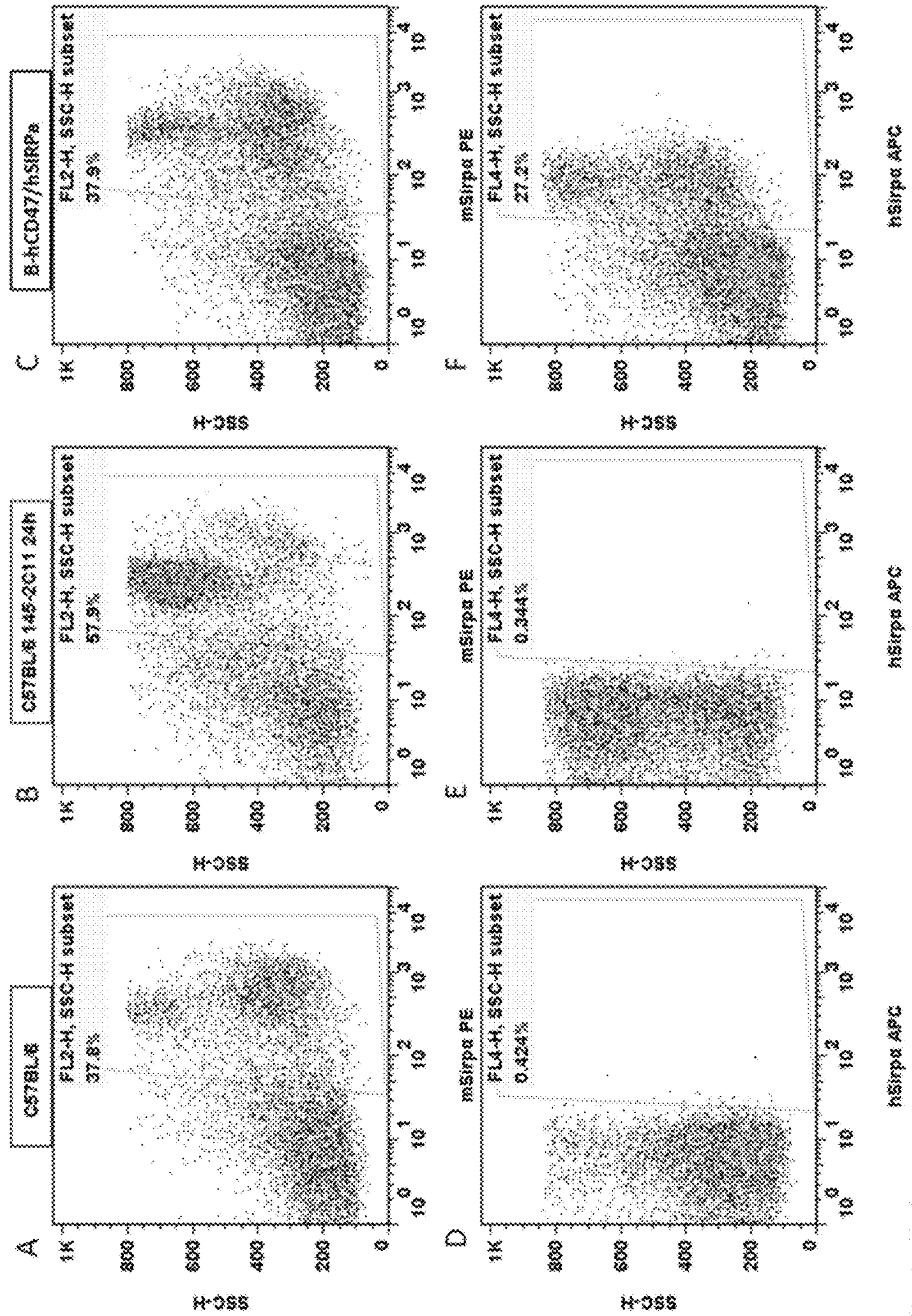
FIGS. 15A-15F are flow cytometry results of wildtype C57BL/6 mice (FIGS. 15A, 15B, 15D, and 15E) and double humanized CD47/SIRPα homozygous mice (FIGS. 15C, 15F). Anti-CD3 antibody was used to activate spleen cells in FIGS. 15B, 15C, 15E and 15F. Flow cytometry was performed with antibody against mouse SIRPα (mSIRPα PE) (FIGS. 15A-15C) and antibody against human SIRPα (hSIRPα APC) (FIGS. 15D-15F). In the control groups, no spleen cells stained with hSIRPα APC were observed in wildtype mice (FIGS. 15D and 15E); in double humanized CD47/SIRPα groups, spleen cells stained with hSIRPα APC were observed (FIG. 15F).

FACS: Flow cytometry was performed with 1) antibody against mouse CD47 (mCD47 AF647) and antibody against mouse TcRβ (mTcRβ PerCP) (FIGS. 14A-14C); and 2) antibody against human CD47 (hCD47 PE), and antibody against mouse TcRβ (mTcRβ PerCP) (FIGS. 14D-14F); 3) antibody against mouse SIRPα (mSIRPα PE) (FIGS. 15A-15C); and 4) antibody against human SIRPα (hSIRPα APC) (FIGS. 15D-15F).

As shown in FIGS. 14A-14F and FIGS. 15A-15F, no spleen cells stained with hCD47 PE or hSIRPα APC were observed in wildtype C57BL/6 mice with or without anti-CD3 antibody activation. Spleen cells stained with hCD47 PE or hSIRPα APC were observed in transgenic mice homozygous for both humanized CD47 and humanized SIRPα (homozygous $CD47^{H/H}$/$SIRP\alpha^{H/H}$).

RT-PCR: RT-PCR experiments were performed to confirm the genetic makeup of $CD47^{H/H}$/$SIRP\alpha^{H/H}$ mice. Total RNA was extracted from spleens and reverse-transcribed into cDNA.

The primer pair mCD47 RT-PCR F2: 5'-GTCATCCCTTGCATCGTCCG-3' (SEQ ID NO: 87) and mCD47 RT-PCR R2: GTCATCCCTTGCATCGTCCG (SEQ ID NO: 88) was used to amplify a 230 bp sequence of mouse CD47.

The primer pair hCD47 RT-PCR F1: ACACTGTCGTCATTCCATGCT (SEQ ID NO: 89) and hCD47 RT-PCR R1: CCTGTGTGTGAGACAGCATCA (SEQ ID NO: 90) was used to amplify an approximately 226 bp sequence of human CD47.

The primer pair mSirpα RT-PCR F2 (SEQ ID NO: 76) and mSirpα RT-PCR R2 (SEQ ID NO: 77) was used to amplify an approximately 210 bp sequence of mouse SIRPα.

The primer pair hSIRPα RT-PCR (SEQ ID NO: 78) and hSIRPα RT-PCR R1 (SEQ ID NO: 79) was used to amplify an approximately 100 bp sequence of human SIRPα.

Figure 16:
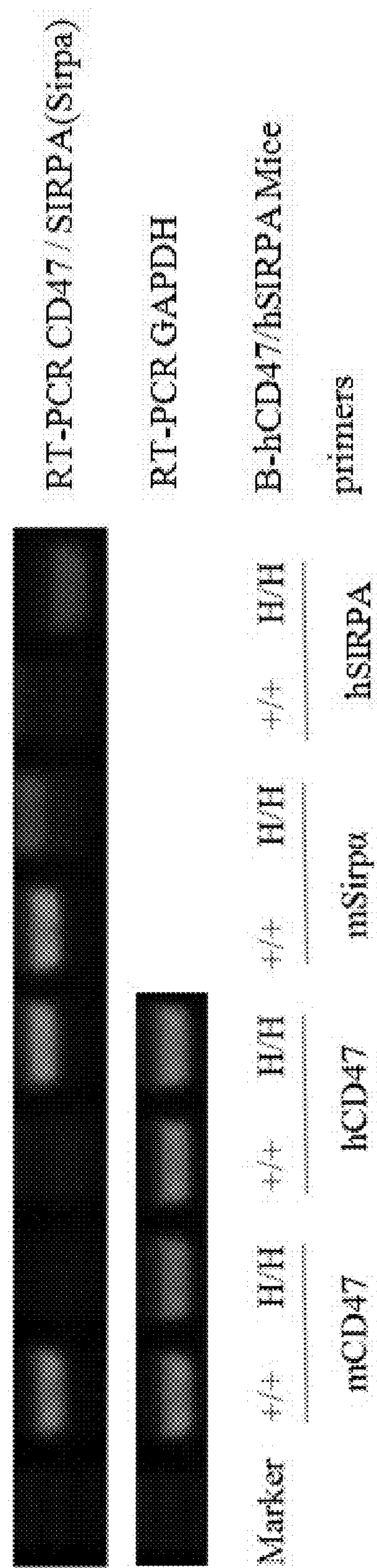
FIG. 16 shows results from RT-PCR experiments amplifying sequences from human CD47 mRNA, mouse CD47 mRNA, human SIRPα mRNA and mouse SIRPα mRNA in double humanized CD47/SIRPα mice. +/+ indicates wildtype C57BL/6 mice; H/H in the figure indicates that the mouse is homozygous for both humanized CD47 and humanized SIRPα; and GAPDH was used as a control. Mouse CD47 mRNA and mouse SIRPα mRNA were detected in wildtype C57BL/6 mice. Human CD47 mRNA and human SIRPα mRNA were detected in double humanized CD47/SIRPα mice.

GAPDH was used as an internal control. RT-PCR results are shown in FIG. 16. Mouse CD47 mRNA and mouse SIRPα mRNA were detected in wildtype C57BL/6 mice after anti-CD3 antibody activation. mRNA of human CD47 and human SIRPα were detected in $CD47^{H/H}$/$SIRP\alpha^{H/H}$ mice.

The $CD47^{H/H}$/$SIRP\alpha^{H/H}$ mice can be used to further prepare a triple transgenic mouse model that are homozygous for humanized CD47, humanized SIRPα, and humanized PD-1. CD47, SIRPα, and PD-1 are all on different chromosomes. Mating (or IVF) $CD47^{H/H}$/$SIRP\alpha^{H/H}$ mice with humanized PD-1 mouse (e.g. B-hPD-1 mice), followed by screening and further mating, can produce triple humanized CD47/SIRPα/PD-1 mice.

Example 13. Methods Based on Embryonic Stem Cell Technologies

The non-human mammals described herein can also be prepared through other gene editing systems and approaches, including but not limited to: gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other techniques.

Based on the genetic map of mouse SIRPα (FIG. 2), a gene targeting strategy was designed as shown in FIG. 17. FIG. 17 shows the design of the recombinant vector. Since the objective is to replace exon 2 of the mouse SIRPα gene in whole or in part with the corresponding sequence in human SIRPα gene, a recombinant vector that contains a 5' homologous arm (4268 bp), a 3' homologous arm (4653 bp) and a sequence fragment from human SIRPα (324 bp) is designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm. Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are then screened by using the positive clone marker gene, and Southern Blot technique can be used for DNA recombination identification. For the selected positive clones, the cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wildtype mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (neo, etc.), and then the humanized SIRPα homozygous mice can be obtained by mating these mice with each other. The methods of genotyping and analyzing the F1 heterozygous mice or F2 homozygous mice are similar to the methods described above.

Example 14: Pharmacological Testing of Antibodies Using Humanized SIRPα Mouse Model Humanized SIRPα mice (B-hSIRPα) (9 weeks old) were subcutaneously injected with mouse colon cancer cell MC38-hCD47 (MC38-hCD47 cells were genetically modified to express human CD47, and did not express mouse CD47) ($5\times10^5$/100 μl PBS). When the tumor volume grew to about 100 $mm^3$, the mice were randomly divided to a control group and treatment groups (n=5/group). Each of the treatment groups was treated with one anti-human SIRPα antibodies (Ab1, Ab2, Ab3, and Ab4). The dosage was 10 mg/kg. The control group was injected with physiological saline. The administration frequency was one injection every three days (six injections in total). The mice were measured for their tumor size and body weight twice a week, and were euthanized when tumor size reached 3000 $mm^3$.

Figure 18:
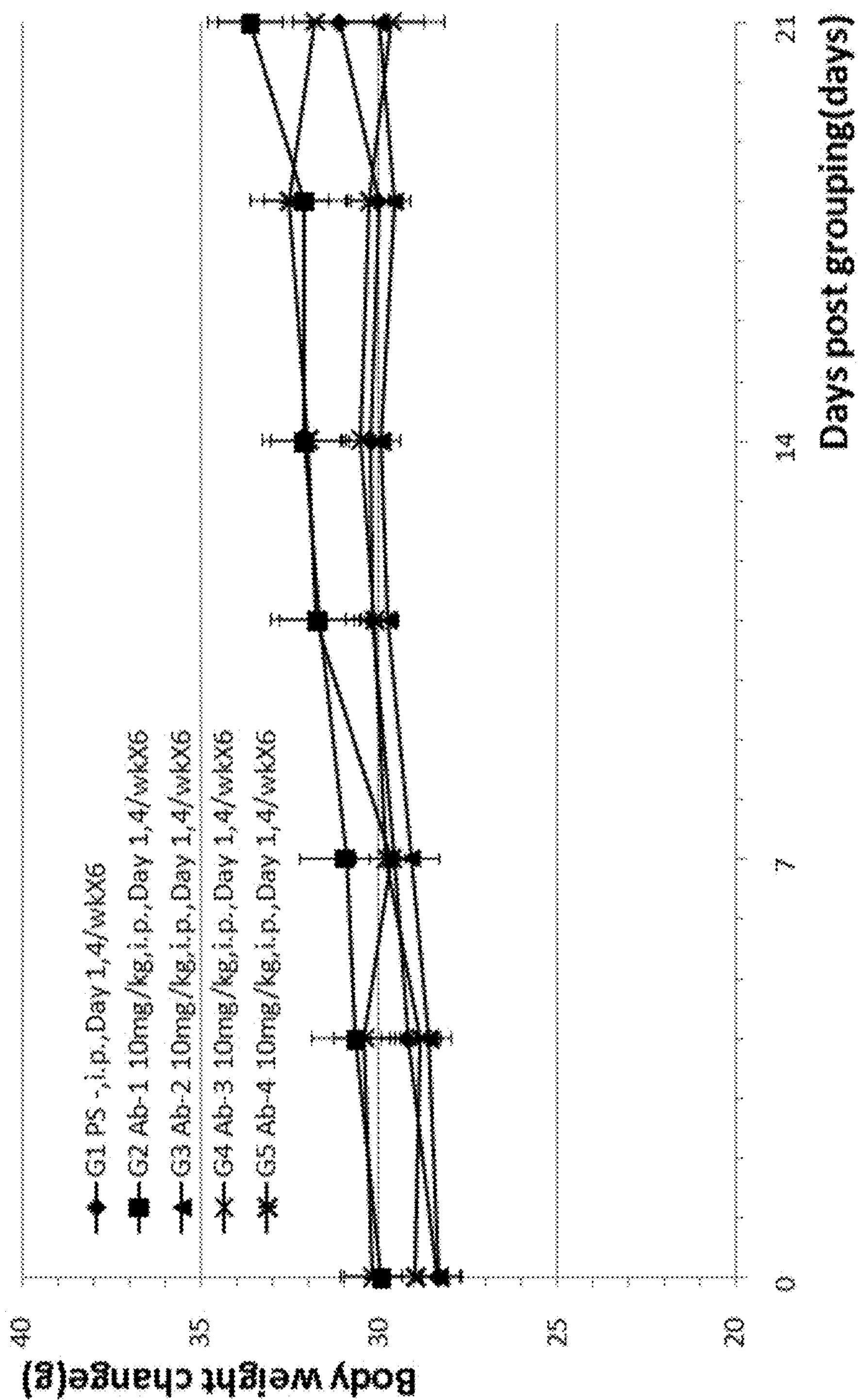
FIG. 18. Mouse colon cancer cells that express human CD47 (MC38-hCD47) were injected into humanized SIRPα mice (B-hSIRPα). Antitumor efficacy studies were performed with four anti-hSIRPα antibodies (10 mg/kg). The average weights of the mice in groups G1-G5 had no significant difference.
Figure 19:
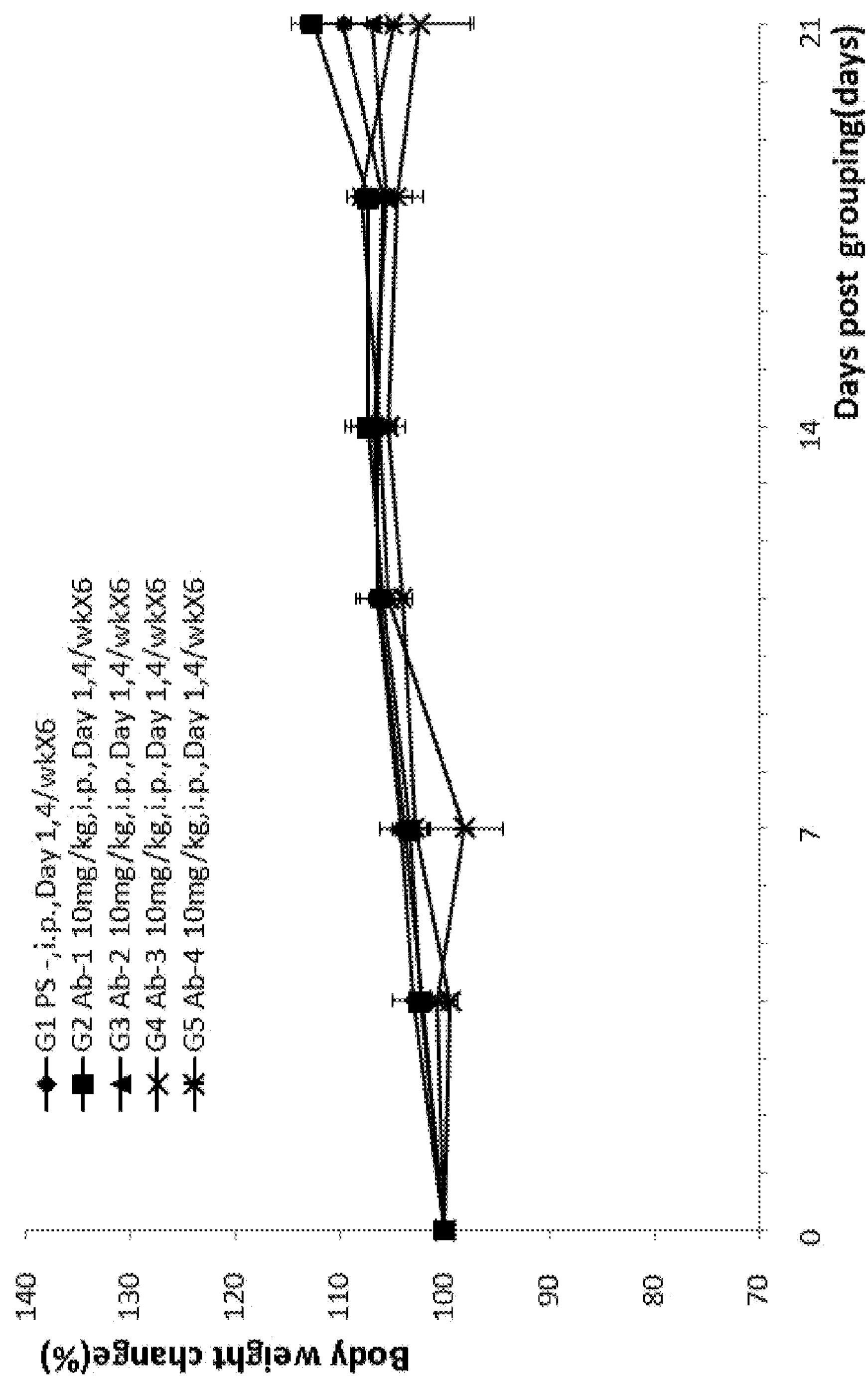
FIG. 19. Mouse colon cancer cells that express human CD47 (MC38-hCD47) were injected into humanized SIRPα mice (B-hSIRPα). Antitumor efficacy studies were performed with four anti-hSIRPα antibodies (10 mg/kg). The weight change percentage of the mice is shown in the figure.
Figure 20:
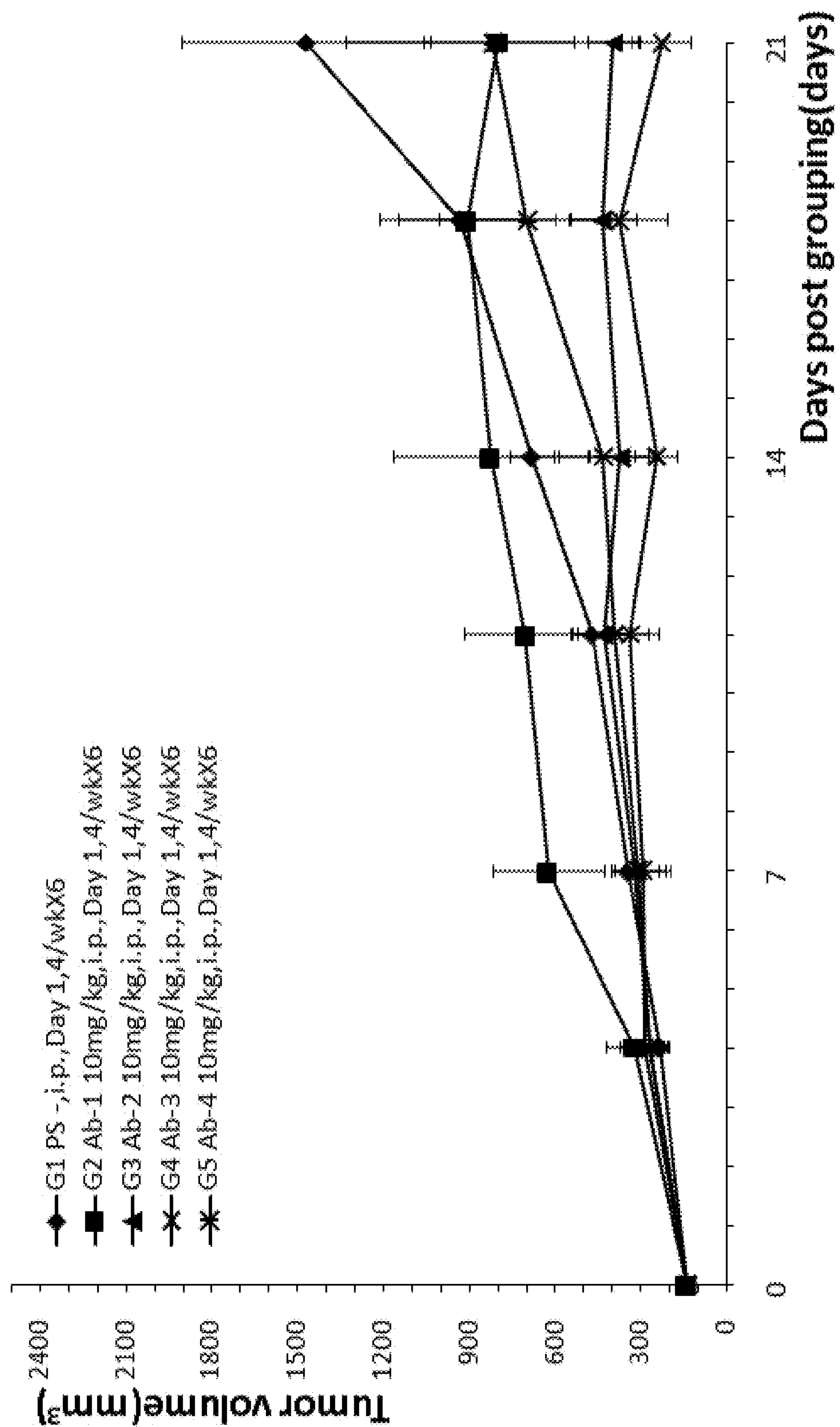
FIG. 20. Mouse colon cancer cells that express human CD47 (MC38-hCD47) were injected into humanized SIRPα mice (B-hSIRPα). Antitumor efficacy studies were performed with four anti-hSIRPA antibodies (10 mg/kg). The average tumor size in each group is shown in the figure.

Overall, the animals in each group were generally healthy, and the body weights of all the treatment groups were not significantly different from the control group (FIG. 18 and FIG. 19) at the end of the experiment (21 days after grouping), indicating that the anti-hSIRPα antibodies were well tolerated by the mice and did not cause obvious toxic effects.

The tumor sizes were different in different groups: tumor in the control group mice continued to grow, while the tumor in groups injected with anti-hSIRPα antibodies were suppressed to various extents, indicating that the anti-hSIRPα antibodies had different tumor inhibitory effects in vivo.

Table 20 shows results of this experiment, including the tumor volumes at the day of grouping, 14 days after the grouping, and at the end of the experiment (21 days after grouping), the survival rate of the mice, the number of tumor-free mice, the Tumor Growth Inhibition value ($TGI_{TV}$ %), and the statistical p value for weight and tumor volume between treatment groups and the control group

TABLE 20

| | | Tumor volume (mm$^3$) | | | | Tumor | | P value | |
|---|---|---|---|---|---|---|---|---|---|
| | | Day 0 | Day 14 | Day 21 | Survival | Free | $TGI_{TV}$ % | Weight | Tumor Volume |
| Control | G1 | 141 ± 10 | 682 ± 77 | 1469 ± 433 | 5/5 | 0/5 | N/A | N/A | N/A |
| Treatment | G2 (Ab1) | 141 ± 9 | 824 ± 343 | 797 ± 261 | 5/5 | 0/5 | 50.6 | 0.153 | 0.221 |
| | G3 (Ab2) | 141 ± 9 | 372 ± 113 | 397 ± 89 | 4/5 | 0/5 | 80.7 | 0.477 | 0.068 |
| | G4 (Ab3) | 141 ± 11 | 246 ± 75 | 229 ± 102 | 5/5 | 0/5 | 93.4 | 0.487 | 0.024 |
| | G5 (Ab4) | 141 ± 11 | 433 ± 157 | 815 ± 514 | 4/5 | 0/5 | 49.2 | 0.825 | 0.360 |

The animal weight in different groups all increased and showed no significant difference among the groups (P>0.05), indicating that the four anti-hSIRPα antibodies were well tolerated. One mouse died in the Ab2 treatment group (G3) and one mouse died in the Ab4 treatment group (G5), indicating that Ab2 and Ab4 may be toxic.

Average tumor volume for the control group (G1) is 1469±433 mm$^3$; the average volume for the treatment groups are: 797±261 mm$^3$ (G2), 397±89 mm$^3$ G3), 229±102 mm$^3$ (G4), and 815±514 mm$^3$ (G5). Mice in treatment groups all had smaller average tumor size compared to the control group (G1), with $TGI_{TV}$ values at 50.6%, 80.7%, 93.4%, and 49.2%, indicating that anti-hSIRPα antibodies had different tumor-inhibitory effects. Under the same dosage and administration frequency, Ab2 (G3), Ab3 (G4) showed significant tumor inhibitory effects ($TGI_{TV}$>60%), which were better than those of Ab1 and Ab4. This experiment shows that different anti-hSIRPα antibodies had different efficacies in terms of inhibiting tumor growth in B-hSIRPα mouse model.

This example demonstrates that the humanized SIRPα mouse model is useful for screening and testing therapeutic agents (e.g. antibodies) targeting human SIRPα. The model is useful for testing efficacies and/or toxicities of the therapeutic agents.

Example 15: Pharmacological Testing of Antibodies Using Double Humanized CD47/SIRPα Mouse Model Double humanized (CD47/SIRPα) mice (7-9 weeks old) were subcutaneously injected with mouse colon cancer cell MC38. When the tumor volume grew to about 100 mm$^3$, the mice were randomly divided to a control group and treatment groups (n=5/group). Each of the treatment groups was treated with one antibody. The six treatment groups were treated with six antibodies as follows: anti-hCD47 antibody AB1, anti-hCD47 antibody AB2, anti-hCD47 antibody AB3, anti-hSIRPα antibody Ab-S1, anti-hSIRPα antibody Ab-S2, and anti-hSIRPα antibody Ab-S3. The control group was injected with physiological saline. The mice were measured for their tumor size and weight twice a week, and were euthanized when tumor size reached 3000 mm$^3$.

Figure 21:
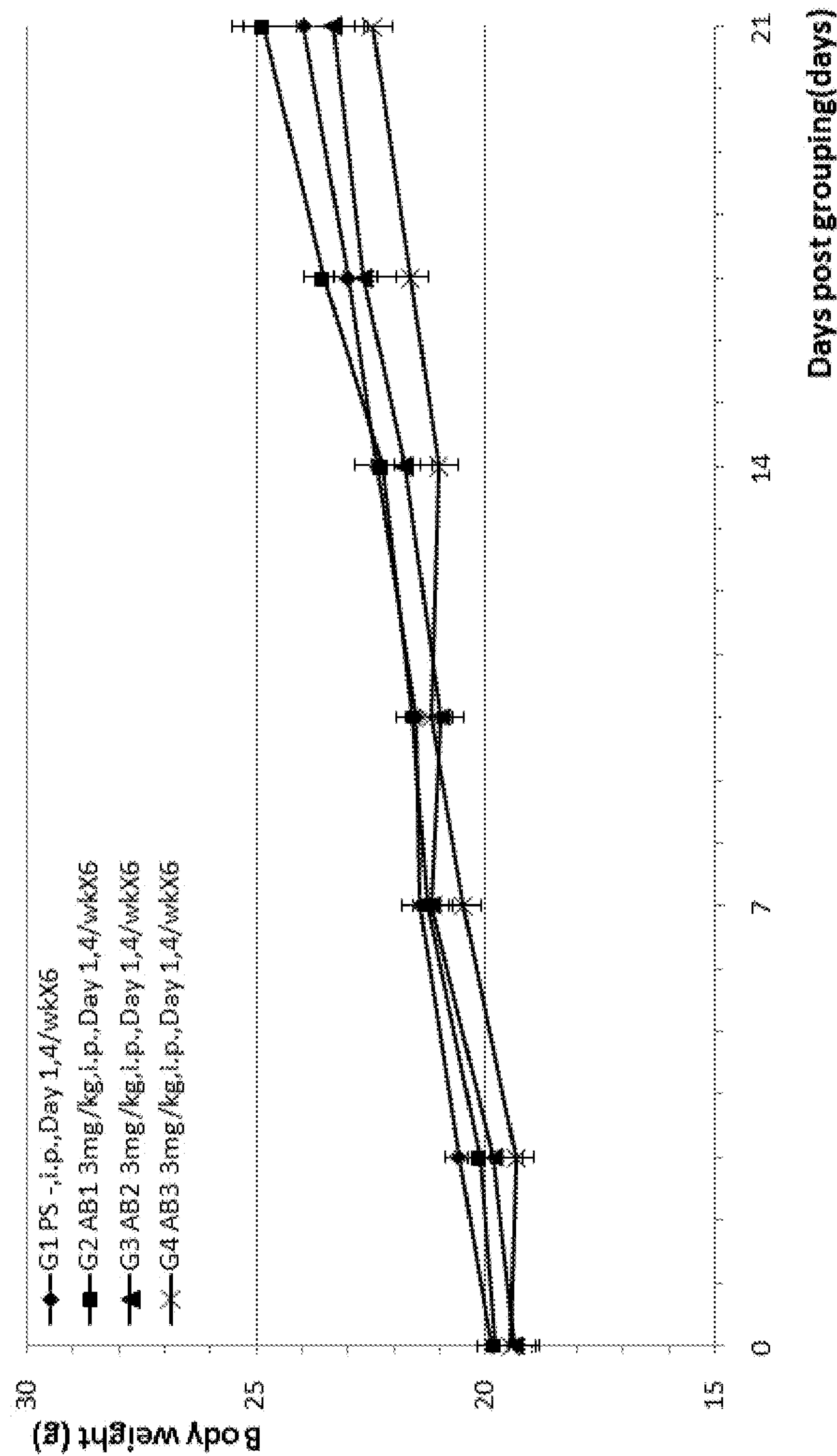
FIG. 21. Mouse colon cancer cells MC38 were injected into double humanized CD47/SIRPα mice. Antitumor efficacy studies were performed with anti-hCD47 antibodies. The average weights of the different groups are shown in the figure.
Figure 22:
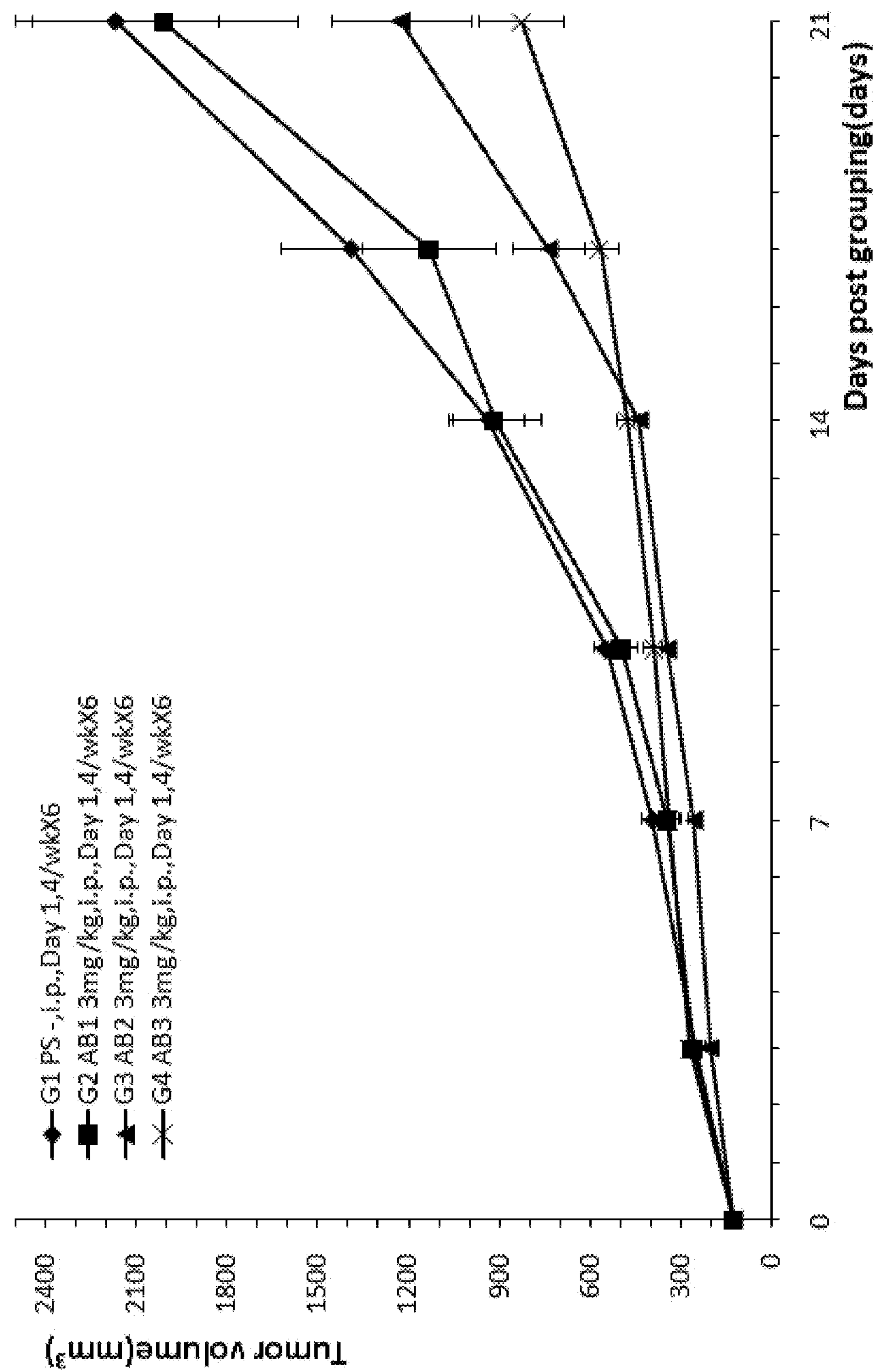
FIG. 22. Mouse colon cancer cells MC38 were injected into double humanized CD47/SIRPα mice. Antitumor efficacy studies were performed with anti-hCD47 antibodies. The average tumor size in each group is shown in the figure.
Figure 23:
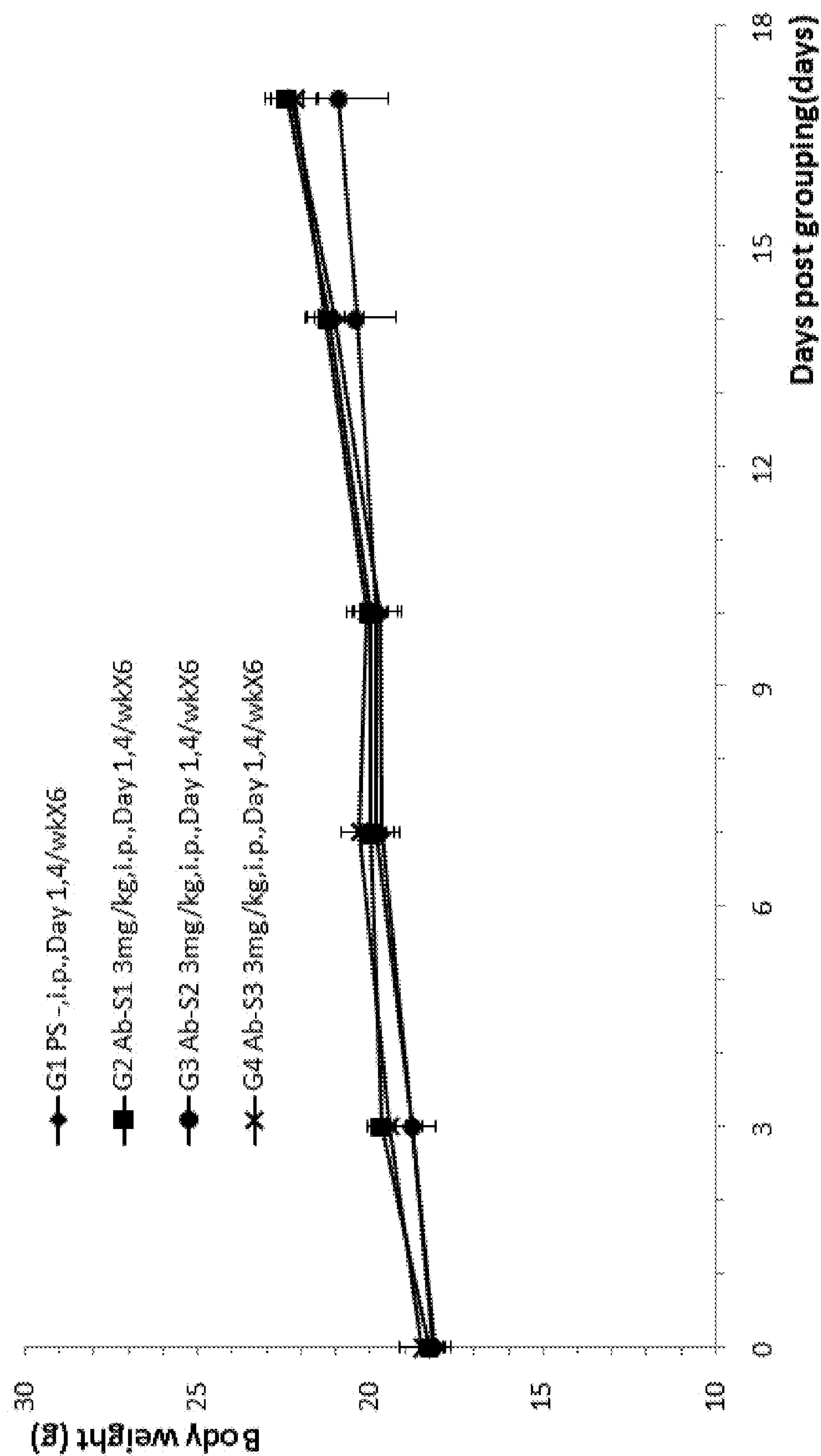
FIG. 23 Mouse colon cancer cells MC38 were injected into double humanized CD47/SIRPα mice. Antitumor efficacy studies were performed with anti-hSIRPα antibodies. The average weights of the different groups are shown in the figure.
Figure 24:
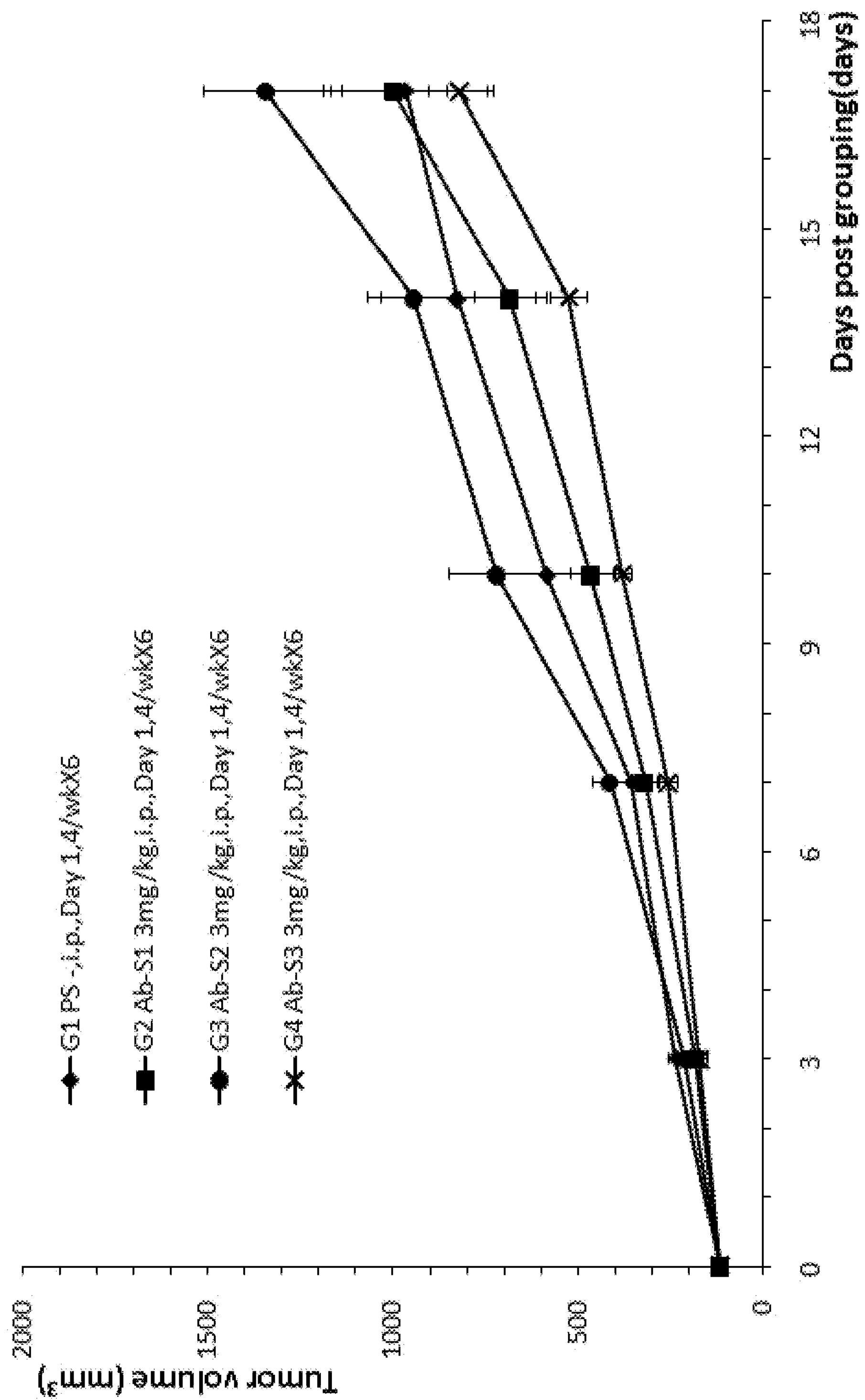
FIG. 24. Mouse colon cancer cells MC38 were injected into double humanized CD47/SIRPα mice. Antitumor efficacy studies were performed with anti-SIRPα antibodies. The average tumor size in each group is shown in the figure.

Overall, the animals in each group were healthy, and the body weights of all the treatment groups were not significantly different from the control group (FIG. 21 and FIG. 23), indicating that the three anti-hCD47 antibodies and the three anti-hSIRPα antibodies were well tolerated by the mice and did not have obvious toxic effects.

Although the body weights did not have significant difference over the course of the entire experimental period (FIG. 21 and FIG. 23), the tumor sizes were different. Tumor size in the control group continued to grow, while the tumor size in the groups injected with anti-hCD47 antibodies decreased as compared to the control group, indicating that the three anti-hCD47 antibodies had different tumor inhibitory effects.

Tumor growth in groups treated with anti-hSIRPα antibodies were also inhibited, indicating that the three anti-hSIRPα antibodies had lower tumor inhibitory effects. None of the six antibodies had obvious toxic effects to the animals.

Table 21 shows results for this experiment, including the tumor volumes at the day of grouping (day 0), 14 days after the grouping, and at the end of the experiment, the survival rate of the mice, and the Tumor Growth Inhibition value ($TGI_{TV}$ %).

TABLE 21

| | | Tumor volume (mm$^3$) | | | | |
|---|---|---|---|---|---|---|
| Anti-hCD47 antibodies | | Day 0 | Day 14 | Day 21 | Survival | $TGI_{TV}$ % |
| Control | G1 | 128 ± 12 | 939 ± 120 | 2166 ± 335 | 5/5 | N/A |
| Treatment | G2 | 128 ± 8 | 917 ± 154 | 2007 ± 438 | 5/5 | 7.8 |
| | G3 | 128 ± 9 | 440 ± 23 | 1227 ± 229 | 5/5 | 46.7 |
| | G4 | 128 ± 10 | 478 ± 37 | 828 ± 139 | 5/5 | 65.6 |

| | | Tumor volume (mm$^3$) | | | | |
|---|---|---|---|---|---|---|
| Anti-hSIRPα antibodies | | Day 0 | Day 14 | Day 17 | Survival | $TGI_{TV}$ % |
| Control | G1 | 117 ± 4 | 827 ± 208 | 967 ± 221 | 5/5 | N/A |
| Treatment | G2 | 116 ± 4 | 685 ± 96 | 999 ± 320 | 5/5 | 0 |
| | G3 | 117 ± 10 | 944 ± 125 | 1342 ± 170 | 5/5 | 0 |
| | G4 | 116 ± 5 | 527 ± 49 | 820 ± 88 | 5/5 | 17.2 |

All mice survived to the end of the experiment. In groups treated with anti-hCD47 antibodies, the average tumor volume is 2166±335 mm$^3$ in the control group (G1), 2007±438

$mm^3$ in the AB1 treatment group (G2), 1227±229 $mm^3$ in the AB2 treatment group (G3), and 828±139 $mm^3$ in the AB3 treatment group (G4). The average tumor size in G2 group did not show significant difference from that in the G1 group, while the average tumor sizes in G3 and G4 groups each showed significant ($p<0.05$) difference from that in G1 group, with the $TGI_{TV}$ % being 46.7% and 65.6% respectively. The results indicate that the three anti-hCD47 antibodies had different tumor inhibitory effects, while all were safe to use without obvious toxicity.

In groups treated with anti-hSIRPα antibodies, tumor inhibitory effects were not significant for the Ab-S1 (G2) and the Ab-S2 (G3) treatment groups compared to the control (G1) group. The Ab-S3 treatment group (G4) had an average tumor size of 820±88 $mm^3$, smaller than the control (G1) group. The results indicate that the three anti-hSIRPα antibodies had different tumor inhibitory effects, with the Ab-S3 antibody having better tumor inhibitory effects than Ab-S1 and Ab-S2.

This example demonstrates that the double humanized (CD47/SIRPα) mouse model is useful for screening and testing for therapeutic agents (e.g. antibodies) targeting human CD47 or human SIRPα. The mouse model is useful for testing efficacies of the therapeutic agents.

Example 16: Quantification of Binding Between SIRPα and Mouse or Human CD47

Experiments were performed to test the binding affinity between CD47 and SIRPα in mice with different backgrounds. Wildtype mice in C57BL6 background, wildtype mice in BALB/c background, and humanized SIRPα mice (B-hSIRPα) in C57BL/6 background were tested. Peritoneal cavity cells of mice were collected and plated on 96-well plates. Mouse CD47 proteins or human CD47 proteins were added to the wells and incubated with these cells. The cells in the wells were further incubated with a primary human antibody against mouse CD47 or human CD47, and a secondary antibody anti-human IgG (AF647-Anti-hIgG), which recognizes the primary antibodies. Fluorescent labeled antibodies against mouse CD11b (Anti-mCD11b PE) or against mouse F4/80 (Anti-mF4/80 FITC) were used to label different populations of mouse immune cells.

Figures 27A, 27B:
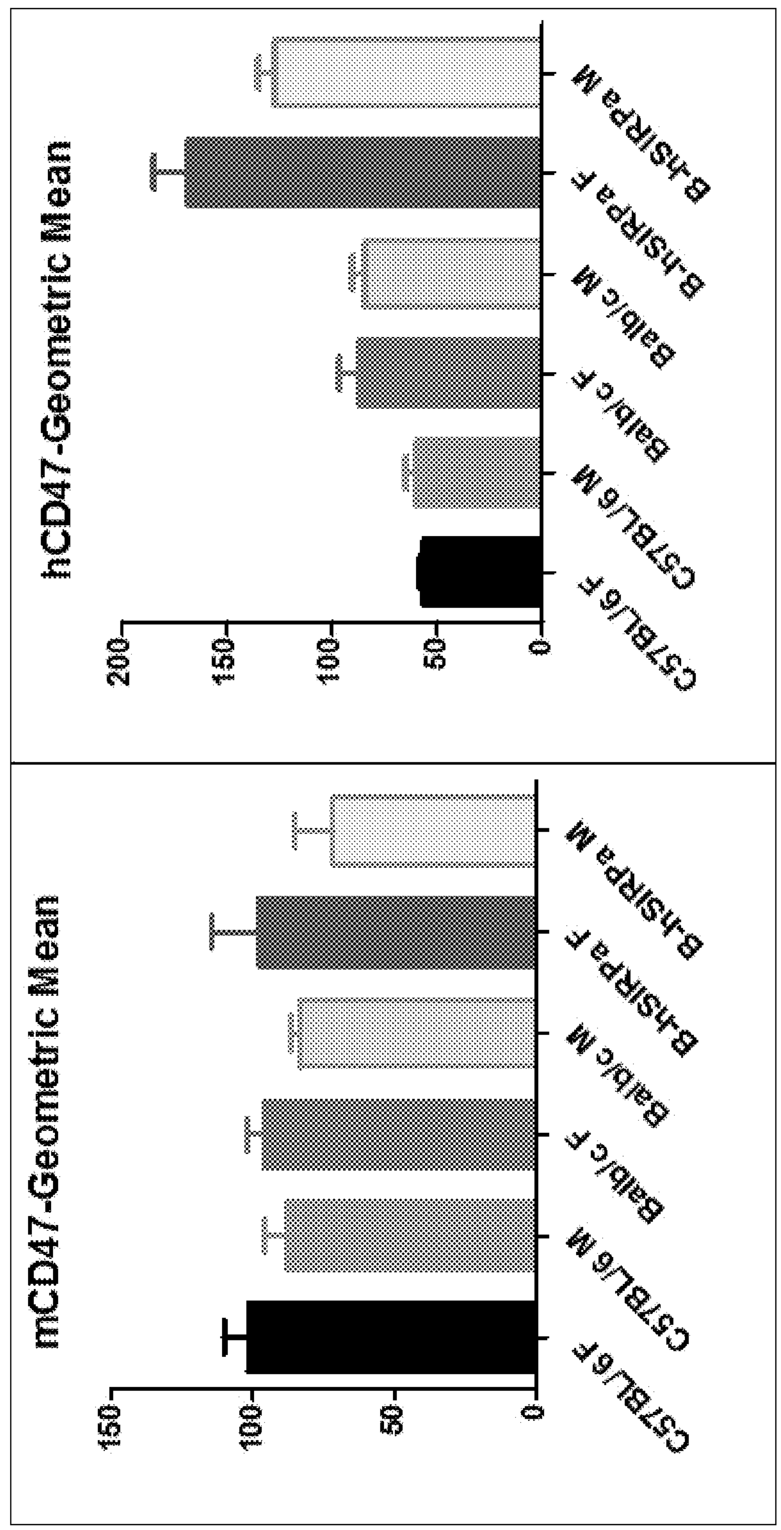
FIG. 27A shows the quantification results from flow cytometry analysis indicating the binding affinity between SIRPα and mouse CD47. The Y axis is the geometric mean of flow cytometry signal. "M" in X axis indicates male, and "F" in X axis indicates female.
FIG. 27B shows the quantification results from flow cytometry analysis indicating the binding affinity between SIRPα and human CD47. The Y axis is the geometric mean of flow cytometry signal. "M" in X axis indicates male, and "F" in X axis indicates female.

The cells were then subject to flow cytometry analysis. The results were quantified and plotted in FIGS. 27A-27B. The results show that the binding between mouse CD47 proteins and the endogenous SIRPα proteins in wildtype mice in both C57BL6 and BALB/c background had a geometric mean around 100 (FIG. 27A). Similar values were observed in humanized SIRPα mice (B-hSIRPα), indicating that the humanized SIRPα proteins in the B-hSIRPα mouse line can bind to mouse CD47 (FIG. 27A) (no significant difference were found between the B-hSIRPα mice and the wildtype mice).

The results also show that the binding between human CD47 and endogenous mouse SIRPα proteins in wildtype C57BL6 mice is weaker than in wildtype BALB/c mice (FIG. 27B). The difference is significant ($P<0.05$). The binding of human CD47 proteins to endogenous mouse SIRPα proteins in wildtype BALB/c mice was comparable to the binding of mouse CD47 proteins to endogenous mouse SIRPα proteins (no significant difference) (FIGS. 27A and 27B). In addition, human CD47 and humanized SIRPα proteins in the humanized B-hSIRPα mice had a much stronger binding affinity as compared to the binding between human CD47 and endogenous mouse SIRPα proteins (FIG. 27B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mouse whose genome comprises a chimeric SIRPα gene encoding a chimeric SIRPα protein, wherein the chimeric SIRPα gene comprises a replacement of a portion of mouse SIRPα gene exon 2 with a portion of human SIRPα gene exon 3, wherein the chimeric SIRPα gene further comprises mouse SIRPα gene exon 3 and mouse SIRPα gene exon 4, wherein the mouse expresses the chimeric SIRPα protein.

2. The mouse of claim 1, wherein the genome of the mouse comprises the chimeric SIRPα gene at an endogenous SIRPα gene locus, wherein the chimeric SIRPα gene is operably linked to an endogenous regulatory element at the endogenous SIRPα gene locus.

3. The mouse of claim 1, wherein the chimeric SIRPα gene encodes an amino acid sequence that is at least 70% identical to SEQ ID NO: 8, 25, 26, 27, or 28.

4. The mouse of claim 1, wherein the chimeric SIRPα protein comprises a sequence that is at least 90% identical to amino acids 31-138 of SEQ ID NO: 4.

5. The mouse of claim 1, wherein the mouse does not express endogenous SIRPα protein.

6. The mouse of claim 1, wherein the mouse is homozygous with respect to the chimeric SIRPα gene.

7. The mouse of claim 1, wherein the mouse further comprises a sequence encoding a human or humanized CD47.

8. The mouse of claim 1, wherein exon 2 at the endogenous SIRPα gene locus is modified by CRISPR with sgRNAs that target SEQ ID NO: 44 and SEQ ID NO: 54.

9. A genetically modified mouse or a progeny thereof, wherein the genetically modified mouse is made by a method comprising the steps of:

modifying genome of a fertilized egg or an embryo of a mouse by CRISPR with sgRNAs that target a 5'-terminal targeting site and a 3'-terminal targeting site, wherein the 5' -terminal targeting site is selected from the group consisting of target SEQ ID NOS: 39-47 and the 3'-terminal targeting site is selected from the group consisting of SEQ ID NOS: 48-58, wherein an endogenous SIRPα gene locus in the genome of the fertilized egg or the embryo is modified; and transplanting the fertilized egg or the embryo to a recipient mouse to produce the genetically-modified mouse.

10. The generically-modified mouse of claim 9, wherein the 5'-terminal targeting site is SEQ ID NO: 44 and the 3'-terminal targeting site is SEQ ID NO: 54.

11. The mouse of claim 1, wherein the chimeric SIRPα gene encodes an amino acid sequence that is at least 90% identical to SEQ ID NO: 8.

12. The mouse of claim 1, wherein the chimeric SIRPα gene encodes an amino acid sequence that is at least 90% identical to SEQ ID NO: 25.

13. The mouse of claim 1, wherein the chimeric SIRPα gene encodes an amino acid sequence that is at least 90% identical to SEQ ID NO: 26.

14. The mouse of claim 1, wherein the chimeric SIRPα gene encodes an amino acid sequence that is at least 90% identical to SEQ ID NO: 27.

15. The mouse of claim 1, wherein the chimeric SIRPα gene encodes an amino acid sequence that is at least 90% identical to SEQ ID NO: 28.

16. The mouse of claim 1, wherein at least 100 contiguous nucleotides in mouse SIRPα gene exon 2 are replaced by at least 100 contiguous nucleotides in human SIRPα gene exon 3.

17. The mouse of claim 1, wherein at least 200 contiguous nucleotides in mouse SIRPα gene exon 2 are replaced by at least 200 contiguous nucleotides in human SIRPα gene exon 3.

18. The mouse of claim 1, wherein at least 300 contiguous nucleotides in mouse SIRPα gene exon 2 are replaced by at least 300 contiguous nucleotides in human SIRPα gene exon 3.

19. The mouse of claim 1, wherein the chimeric SIRPα gene encodes an amino acid sequence that is identical to SEQ ID NO: 8.

* * * * *

UNITED STATES PATENT AND TRADEMARK OFFICE

CERTIFICATE OF CORRECTION

PATENT NO. : 10,973,212 B2
APPLICATION NO. : 16/436545
DATED : April 13, 2021
INVENTOR(S) : Yuelei Shen et al.

It is certified that error appears in the above-identified patent and that said Letters Patent is hereby corrected as shown below:

In the Claims

In Column 168, Line Number 65, Claim 10, delete "generically-modified" and insert -- genetically-modified --.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*

```
SEQUENCE LISTING

<160> NUMBER OF SEQ ID NOS: 101

<210> SEQ ID NO 1
<211> LENGTH: 4031
<212> TYPE: DNA
<213> ORGANISM: Mus musculus

<400> SEQUENCE: 1

cgggaaggtg cgggcgcgag gagggggcgc tcggccgggc cgccctcgcg ctggcctcgc     60

gacggctccg cacagcccgc actcgctctg cgagctgtcc ccgctcgcgc ttgctctccg    120

atctccgtcc ccgctccctc tccctcttcc tctccccctc tttccttctc cctcgctatc    180

cgctcccccg cccccgtgcc tctggctctg cgcctggctc cctcgggtcc gctccccttt    240

cccgccggcc tggcccggcg tcacgctccc ggagtctccc cgctcggcgg cgtctcattg    300

tgggaggggg tcagatcacc ccgccgggcg gtggcgctgg ggggcagcgg agggggaggg    360

gccttagtcg ttcgcccgcg ccgcccgccc gcctgccgag cgcgctcacc gccgctctcc    420

ctccttgctc tgcagccgcg gcccatggag cccgccggcc cggcccctgg ccgcctaggg    480

ccgctgctgc tctgcctgct gctctccgcg tcctgtttct gtacaggagc cacggggaag    540

gaactgaagg tgactcagcc tgagaaatca gtgtctgttg ctgctgggga ttcgaccgtt    600
```

-continued

```
ctgaactgca ctttgacctc cttgttgccg gtgggaccca ttaggtggta cagaggagta    660
gggccaagcc ggctgttgat ctacagtttc gcaggagaat acgttcctcg aattagaaat    720
gtttcagata ctactaagag aaacaatatg gacttttcca tccgtatcag taatgtcacc    780
ccagcagatg ctggcatcta ctactgtgtg aagttccaga aaggatcatc agagcctgac    840
acagaaatac aatctggagg gggaacagag gtctatgtac tcgccaaacc ttctccaccg    900
gaggtatccg gcccagcaga caggggcata cctgaccaga aagtgaactt cacctgcaag    960
tctcatggct tctctccccg gaatatcacc ctgaagtggt tcaaagatgg gcaagaactc   1020
cacccccttgg agaccaccgt gaaccctagt ggaaagaatg tctcctacaa catctccagc   1080
acagtcaggg tggtactaaa ctccatggat gttaattcta aggtcatctg cgaggtagcc   1140
cacatcacct tggatagaag ccctcttcgt gggattgcta acctgtctaa cttcatccga   1200
gtttcaccca ccgtgaaggt cacccaacag tccccgacgt caatgaacca ggtgaacctc   1260
acctgccggg ctgagaggtt ctaccccgag gatctccagc tgatctggct ggagaatgga   1320
aacgtatcac ggaatgacac gcccaagaat ctcacaaaga acacggatgg gacctataat   1380
tacacaagct tgttcctggt gaactcatct gctcatagag aggacgtggt gttcacgtgc   1440
caggtgaagc acgaccaaca gccagcgatc acccgaaacc ataccgtgct gggatttgcc   1500
cactcgagtg atcaagggag catgcaaacc ttccctgata ataatgctac ccacaactgg   1560
aatgtcttca tcggtgtggg cgtggcgtgt gctttgctcg tagtcctgct gatggctgct   1620
ctctacctcc tccggatcaa acagaagaaa gccaaggggt caacatcttc cacacggttg   1680
cacgagcccg agaagaacgc cagggaaata acccagatcc aggacacaaa tgacatcaac   1740
gacatcacat acgcagacct gaatctgccc aaagagaaga agcccgcacc ccgggcccct   1800
gagcctaaca accacacaga atatgcaagc attgagacag gcaaagtgcc taggccagag   1860
gataccctca cctatgctga cctggacatg gtccacctca gccgggcaca gccagccccc   1920
aagcctgagc catctttctc agagtatgct agtgtccagg tccagaggaa gtgaatgggg   1980
ctgtggtctg tactaggccc catccccaca agttttcttg tcctacatgg agtggccatg   2040
acgaggacat ccagccagcc aatcctgtcc ccagaaggcc aggtggcacg ggtcctagga   2100
ccaggggtaa gggtggcctt tgtcttccct ccgtggctct tcaacacctc ttgggcaccc   2160
acgtcccctt cttccggagg ctgggtgttg cagaaccaga gggcgaactg gagaaagctg   2220
cctggaatcc aagaagtgtt gtgcctcggc ccatcactcg tgggtctgga tcctggtctt   2280
ggcaacccca ggttgcgtcc ttgatgttcc agagcttggt cttctgtgtg gagaagagct   2340
caccatctct acccaacttg agctttggga ccagactccc tttagatcaa accgccccat   2400
ctgtggaaga actacaccag aagtcagcaa gttttcagcc aacagtgctg gcctccccac   2460
ctcccaggct gactagccct ggggagaagg aaccctctcc tcctagacca gcagagactc   2520
cctgggcatg ttcagtgtgg ccccacctcc cttccagtcc cagcttgctt cctccagcta   2580
gcactaactc agcagcatcg ctctgtggac gcctgtaaat tattgagaaa tgtgaactgt   2640
gcagtcttaa agctaaggtg ttagaaaatt tgatttatgc tgtttagttg ttgttgggtt   2700
tcttttcttt ttaatttctt tttctttttt gatttttttt ctttccctta aaacaacagc   2760
agcagcatct tggctctttg tcatgtgttg aatggttggg tcttgtgaag tctgaggtct   2820
aacagtttat tgtcctggaa ggattttctt acagcagaaa cagatttttt tcaaattccc   2880
agaatcctga ggaccaagaa ggatccctca gctgctactt ccagcaccca gcgtcactgg   2940
gacgaaccag gccctgttct tacaaggcca catggctggc cctttgcctc catggctact   3000
```

```
gtggtaagtg cagccttgtc tgacccaatg ctgacctaat gttggccatt ccacattgag   3060
gggacaaggt cagtgatgcc ccccttcact cacaagcact tcagaggcat gcagagagaa   3120
gggacactcg gccagctctc tgaggtaatc agtgcaagga ggagtccgtt ttttgccagc   3180
aaacctcagc aggatcacac tggaacagaa cctggtcata cctgtgacaa cacagctgtg   3240
agccagggca aaccacccac tgtcactggc tcgagagtct gggcagaggc tctgaccctc   3300
cacccttta actggatgcc ggggcctggc tgggcccaat gccaagtggt tatggcaacc    3360
ctgactatct ggtcttaaca tgtagctcag gaagtggagg cgctaatgtc cccaatccct   3420
ggggattcct gattccagct attcatgtaa gcagagccaa cctgcctatt tctgtaggtg   3480
cgactgggat gttaggagca cagcaaggac ccagctctgt agggctggtg acctgatact   3540
tctcataatg gcatctagaa gttaggctga gttggcctca ctggcccagc aaaccagaac   3600
ttgtctttgt ccgggccatg ttcttgggct gtcttctaat tccaaagggt tggttggtaa   3660
agctccaccc ccttctcctc tgcctaaaga catcacatgt gtatacacac acgggtgtat   3720
agatgagtta aaagaatgtc ctcgctggca tcctaatttt gtcttaagtt tttttggagg   3780
gagaaaggaa caaggcaagg gaagatgtgt agctttggct ttaaccaggc agcctggggg   3840
ctcccaagcc tatggaaccc tggtacaaag aagagaacag aagcgccctg tgaggagtgg   3900
gatttgtttt tctgtagacc agatgagaag gaaacaggcc ctgttttgta catagttgca   3960
acttaaaatt tttggcttgc aaaatatttt tgtaataaag atttctgggt aacaataaaa   4020
aaaaaaaaaa a                                                        4031
```

<210> SEQ ID NO 2
<211> LENGTH: 509
<212> TYPE: PRT
<213> ORGANISM: Mus musculus

<400> SEQUENCE: 2

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
```

```
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Ile Gln Asp Thr Asn Asp Ile Asn
            420                 425                 430

Asp Ile Thr Tyr Ala Asp Leu Asn Leu Pro Lys Glu Lys Lys Pro Ala
        435                 440                 445

Pro Arg Ala Pro Glu Pro Asn Asn His Thr Glu Tyr Ala Ser Ile Glu
    450                 455                 460

Thr Gly Lys Val Pro Arg Pro Glu Asp Thr Leu Thr Tyr Ala Asp Leu
465                 470                 475                 480

Asp Met Val His Leu Ser Arg Ala Gln Pro Ala Pro Lys Pro Glu Pro
                485                 490                 495

Ser Phe Ser Glu Tyr Ala Ser Val Gln Val Gln Arg Lys
            500                 505
```

<210> SEQ ID NO 3
<211> LENGTH: 3868
<212> TYPE: DNA
<213> ORGANISM: Homo sapiens

<400> SEQUENCE: 3

```
cgctcgctcg cagagaagcc gcggcccatg gagcccgccg gcccggcccc cggccgcctc     60

gggccgctgc tctgcctgct gctcgccgcg tcctgcgcct ggtcaggagt ggcgggtgag    120

gaggagctgc aggtgattca gcctgacaag tccgtgttgg ttgcagctgg agagacagcc    180

actctgcgct gcactgcgac ctctctgatc cctgtggggc ccatccagtg gttcagagga    240

gctggaccag gccgggaatt aatctacaat caaaaagaag gccacttccc ccgggtaaca    300
```

```
actgtttcag acctcacaaa gagaaacaac atggactttt ccatccgcat cggtaacatc    360
accccagcag atgccggcac ctactactgt gtgaagttcc ggaaagggag ccccgatgac    420
gtggagttta agtctggagc aggcactgag ctgtctgtgc gcgccaaacc ctctgccccc    480
gtggtatcgg gccctgcggc gagggccaca cctcagcaca cagtgagctt cacctgcgag    540
tcccacggct tctcacccag agacatcacc ctgaaatggt tcaaaaatgg gaatgagctc    600
tcagacttcc agaccaacgt ggaccccgta ggagagagcg tgtcctacag catccacagc    660
acagccaagg tggtgctgac ccgcgaggac gttcactctc aagtcatctg cgaggtggcc    720
cacgtcacct tgcaggggga ccctcttcgt gggactgcca acttgtctga gaccatccga    780
gttccaccca ccttggaggt tactcaacag cccgtgaggg cagagaacca ggtgaatgtc    840
acctgccagg tgaggaagtt ctacccccag agactacagc tgacctggtt ggagaatgga    900
aacgtgtccc ggacagaaac ggcctcaacc gttacagaga acaaggatgg tacctacaac    960
tggatgagct ggctcctggt gaatgtatct gcccacaggg atgatgtgaa gctcacctgc   1020
caggtggagc atgacgggca gccagcggtc agcaaaagcc atgacctgaa ggtctcagcc   1080
cacccgaagg agcagggctc aaataccgcc gctgagaaca ctggatctaa tgaacggaac   1140
atctatattg tggtgggtgt ggtgtgcacc ttgctggtgg ccctactgat ggcggccctc   1200
tacctcgtcc gaatcagaca gaagaaagcc cagggctcca cttcttctac aaggttgcat   1260
gagcccgaga agaatgccag agaaataaca caggacacaa atgatatcac atatgcagac   1320
ctgaacctgc ccaaggggaa gaagcctgct ccccaggctg cggagcccaa caaccacacg   1380
gagtatgcca gcattcagac cagcccgcag cccgcgtcgg aggacaccct cacctatgct   1440
gacctggaca tggtccacct caaccggacc cccaagcagc cggcccccaa gcctgagccg   1500
tccttctcag agtacgccag cgtccaggtc ccgaggaagt gaatgggacc gtggtttgct   1560
ctagcaccca tctctacgcg ctttcttgtc ccacagggag ccgccgtgat gagcacagcc   1620
aacccagttc ccggagggct ggggcggtgc aggctctggg acccaggggc caggtggct    1680
cttctctccc cacccctcct tggctctcca gcacttcctg ggcagccacg gccccctccc   1740
cccacattgc cacatacctg gaggctgacg ttgccaaacc agccagggaa ccaacctggg   1800
aagtggccag aactgcctgg ggtccaagaa ctcttgtgcc tccgtccatc accatgtggg   1860
ttttgaagac cctcgactgc ctccccgatg ctccgaagcc tgatcttcca gggtggggag   1920
gagaaaatcc cacctcccct gacctccacc acctccacca ccaccaccac caccaccacc   1980
accactacca ccaccaccca actggggcta gagtggggaa gatttcccct ttagatcaaa   2040
ctgccccttc catggaaaag ctggaaaaaa actctggaac ccatatccag gcttggtgag   2100
gttgctgcca acagtcctgg cctcccccat ccctaggcta aagagccatg agtcctggag   2160
gaggagagga cccctcccaa aggactggag acaaaaccct ctgcttcctt gggtccctcc   2220
aagactccct ggggcccaac tgtgttgctc cacccggacc catctctccc ttctagacct   2280
gagcttgccc ctccagctag cactaagcaa catctcgctg tggacgcctg taaattactg   2340
agaaatgtga aacgtgcaat cttgaaactg aggtgttaga aaacttgatc tgtggtgttt   2400
tgttttgttt tttttcttaa aacaacagca acgtgatctt ggctgtctgt catgtgttga   2460
agtccatggt tgggtcttgt gaagtctgag gtttaacagt ttgttgtcct ggagggattt   2520
tcttacagcg aagacttgag ttcctccaag tcccagaacc ccaagaatgg gcaagaagga   2580
tcaggtcagc cactccctgg agacacagcc ttctggctgg gactgacttg gccatgttct   2640
```

```
cagctgagcc acgcggctgg tagtgcagcc ttctgtgacc ccgctgtggt aagtccagcc   2700
tgcccagggc tgctgagggc tgcctcttga cagtgcagtc ttatcgagac ccaatgcctc   2760
agtctgctca tccgtaaagt ggggatagtg aagatgacac ccctccccac cacctctcat   2820
aagcacttta ggaacacaca gagggtaggg atagtggccc tggccgtcta tcctacccct   2880
ttagtgaccg cccccatccc ggctttctga gctgatcctt gaagaagaaa tcttccattt   2940
ctgctctcaa accctactgg gatcaaactg gaataaattg aagacagcca gggggatggt   3000
gcagctgtga agctcgggct gattccccct ctgtcccaga aggttggcca gagggtgtga   3060
cccagttacc ctttaacccc cacccttcca gtcgggtgtg agggcctgac cgggcccagg   3120
gcaagcagat gtcgcaagcc ctatttattc agtcttcact ataactctta gagttgagac   3180
gctaatgttc atgactcctg gccttgggat gcccaaggga tttctggctc aggctgtaaa   3240
agtagctgag ccatcctgcc cattcctgga ggtcctacag gtgaaactgc aggagctcag   3300
catagaccca gctctctggg ggatggtcac ctggtgattt caatgatggc atccaggaat   3360
tagctgagcc aacagaccat gtggacagct ttggccagag ctcccgtgtg gcatctggga   3420
gccacagtga cccagccacc tggctcaggc tagttccaaa ttccaaaaga ttggcttgta   3480
aaccttcgtc tccctctctt ttacccagag acagcacata cgtgtgcaca cgcatgcaca   3540
cacacattca gtattttaaa agaatgtttt cttggtgcca ttttcatttt attttatttt   3600
ttaattcttg gagggggaaa taagggaata aggccaagga agatgtatag ctttagcttt   3660
agcctggcaa cctggagaat ccacatacct tgtgtattga accccaggaa aaggaagagg   3720
tcgaaccaac cctgcggaag gagcatggtt tcaggagttt attttaagac tgctgggaag   3780
gaaacaggcc ccattttgta tatagttgca acttaaactt tttggcttgc aaaatatttt   3840
tgtaataaag atttctgggt aataatga                                      3868
```

<210> SEQ ID NO 4
<211> LENGTH: 504
<212> TYPE: PRT
<213> ORGANISM: Homo sapiens

<400> SEQUENCE: 4

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160
```

```
Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500
```

<210> SEQ ID NO 5
<211> LENGTH: 348
<212> TYPE: DNA
<213> ORGANISM: Artificial Sequence
<220> FEATURE:
<223> OTHER INFORMATION: Homo sapiens  and Mus musculus

<400> SEQUENCE: 5

```
gagccacggg ggaggaggag ctgcaggtga ttcagcctga caagtccgtg ttggttgcag     60
```

```
ctggagagac agccactctg cgctgcactg cgacctctct gatccctgtg gggcccatcc    120

agtggttcag aggagctgga ccaggccggg aattaatcta caatcaaaaa gaaggccact    180

tcccccgggt aacaactgtt tcagacctca caaagagaaa caacatggac ttttccatcc    240

gcatcggtaa catcacccca gcagatgccg gcacctacta ctgtgtgaag ttccggaaag    300

ggagccccga tgacgtggag tttaagtctg gagcaggaac agaggtct                 348
```

<210> SEQ ID NO 6
<211> LENGTH: 1530
<212> TYPE: DNA
<213> ORGANISM: Artificial Sequence
<220> FEATURE:
<223> OTHER INFORMATION: Homo sapiens and Mus musculus

<400> SEQUENCE: 6

```
atggagcccg ccggcccggc ccctggccgc ctagggccgc tgctgctctg cctgctgctc     60

tccgcgtcct gtttctgtac aggagccacg ggggaggagg agctgcaggt gattcagcct    120

gacaagtccg tgttggttgc agctggagag acagccactc tgcgctgcac tgcgacctct    180

ctgatccctg tggggcccat ccagtggttc agaggagctg gaccaggccg ggaattaatc    240

tacaatcaaa aagaaggcca cttcccccgg gtaacaactg tttcagacct cacaaagaga    300

aacaacatgg acttttccat ccgcatcggt aacatcaccc cagcagatgc cggcacctac    360

tactgtgtga agttccggaa agggagcccc gatgacgtgg agtttaagtc tggagcagga    420

acagaggtct atgtactcgc caaaccttct ccaccggagg tatccggccc agcagacagg    480

ggcatacctg accagaaagt gaacttcacc tgcaagtctc atggcttctc tccccggaat    540

atcaccctga agtggttcaa agatgggcaa gaactccacc ccttggagac caccgtgaac    600

cctagtggaa agaatgtctc ctacaacatc tccagcacag tcagggtggt actaaactcc    660

atggatgtta attctaaggt catctgcgag gtagcccaca tcaccttgga tagaagccct    720

cttcgtggga ttgctaacct gtctaacttc atccgagttt cacccaccgt gaaggtcacc    780

caacagtccc cgacgtcaat gaaccaggtg aacctcacct gccgggctga gaggttctac    840

cccgaggatc tccagctgat ctggctggag aatggaaacg tatcacggaa tgacacgccc    900

aagaatctca caaagaacac ggatgggacc tataattaca caagcttgtt cctggtgaac    960

tcatctgctc atagagagga cgtggtgttc acgtgccagg tgaagcacga ccaacagcca   1020

gcgatcaccc gaaaccatac cgtgctggga tttgcccact cgagtgatca agggagcatg   1080

caaaccttcc ctgataataa tgctacccac aactggaatg tcttcatcgg tgtgggcgtg   1140

gcgtgtgctt tgctcgtagt cctgctgatg gctgctctct acctcctccg gatcaaacag   1200

aagaaagcca aggggtcaac atcttccaca cggttgcacg agcccgagaa gaacgccagg   1260

gaaataaccc agatccagga cacaaatgac atcaacgaca tcacatacgc agacctgaat   1320

ctgcccaaag agaagaagcc cgcacccccgg gcccctgagc ctaacaacca cacagaatat  1380

gcaagcattg agacaggcaa agtgcctagg ccagaggata ccctcaccta tgctgacctg   1440

gacatggtcc acctcagccg ggcacagcca gcccccaagc ctgagccatc tttctcagag   1500

tatgctagtg tccaggtcca gaggaagtga                                    1530
```

<210> SEQ ID NO 7
<211> LENGTH: 4031
<212> TYPE: DNA
<213> ORGANISM: Artificial Sequence
<220> FEATURE:
<223> OTHER INFORMATION: Homo sapiens and Mus musculus

<400> SEQUENCE: 7

```
cgggaaggtg cgggcgcgag gagggggcgc tcggccgggc cgccctcgcg ctggcctcgc     60
gacggctccg cacagcccgc actcgctctg cgagctgtcc ccgctcgcgc ttgctctccg    120
atctccgtcc ccgctccctc tccctcttcc tctccccctc tttccttctc cctcgctatc    180
cgctccccccg cccccgtgcc tctggctctg cgcctggctc cctcgggtcc gctccccttt    240
cccgccggcc tggcccggcg tcacgctccc ggagtctccc cgctcggcgg cgtctcattg    300
tgggaggggg tcagatcacc ccgccgggcg gtggcgctgg ggggcagcgg agggggaggg    360
gccttagtcg ttcgcccgcg ccgcccgccc gcctgccgag cgcgctcacc gccgctctcc    420
ctccttgctc tgcagccgcg gcccatggag cccgccggcc cggcccctgg ccgcctaggg    480
ccgctgctgc tctgcctgct gctctccgcg tcctgtttct gtacaggagc cacgggggag    540
gaggagctgc aggtgattca gcctgacaag tccgtgttgg ttgcagctgg agagacagcc    600
actctgcgct gcactgcgac ctctctgatc cctgtggggc ccatccagtg gttcagagga    660
gctggaccag gccgggaatt aatctacaat caaaaagaag gccacttccc ccgggtaaca    720
actgtttcag acctcacaaa gagaaacaac atggactttt ccatccgcat cggtaacatc    780
accccagcag atgccggcac ctactactgt gtgaagttcc ggaaagggag ccccgatgac    840
gtggagttta agtctggagc aggaacagag gtctatgtac tcgccaaacc ttctccaccg    900
gaggtatccg gcccagcaga caggggcata cctgaccaga aagtgaactt cacctgcaag    960
tctcatggct tctctccccg gaatatcacc ctgaagtggt tcaaagatgg gcaagaactc   1020
caccccttgg agaccaccgt gaaccctagt ggaaagaatg tctcctacaa catctccagc   1080
acagtcaggg tggtactaaa ctccatggat gttaattcta aggtcatctg cgaggtagcc   1140
cacatcacct tggatagaag ccctcttcgt gggattgcta acctgtctaa cttcatccga   1200
gtttcaccca ccgtgaaggt cacccaacag tccccgacgt caatgaacca ggtgaacctc   1260
acctgccggg ctgagaggtt ctaccccgag gatctccagc tgatctggct ggagaatgga   1320
aacgtatcac ggaatgacac gcccaagaat ctcacaaaga acacggatgg gacctataat   1380
tacacaagct tgttcctggt gaactcatct gctcatagag aggacgtggt gttcacgtgc   1440
caggtgaagc acgaccaaca gccagcgatc acccgaaacc ataccgtgct gggatttgcc   1500
cactcgagtg atcaagggag catgcaaacc ttccctgata ataatgctac ccacaactgg   1560
aatgtcttca tcggtgtggg cgtggcgtgt gctttgctcg tagtcctgct gatggctgct   1620
ctctacctcc tccggatcaa acagaagaaa gccaaggggt caacatcttc cacacggttg   1680
cacgagcccg agaagaacgc cagggaaata acccagatcc aggacacaaa tgacatcaac   1740
gacatcacat acgcagacct gaatctgccc aaagagaaga agcccgcacc ccgggcccct   1800
gagcctaaca accacacaga atatgcaagc attgagacag gcaaagtgcc taggccagag   1860
gataccctca cctatgctga cctggacatg gtccacctca gccgggcaca gccagccccc   1920
aagcctgagc catctttctc agagtatgct agtgtccagg tccagaggaa gtgaatgggg   1980
ctgtggtctg tactaggccc catccccaca agttttcttg tcctacatgg agtggccatg   2040
acgaggacat ccagccagcc aatcctgtcc ccagaaggcc aggtggcacg ggtcctagga   2100
ccaggggtaa gggtggcctt tgtcttccct ccgtggctct tcaacacctc ttgggcaccc   2160
acgtcccctt cttccggagg ctgggtgttg cagaaccaga gggcgaactg gagaaagctg   2220
cctggaatcc aagaagtgtt gtgcctcggc ccatcactcg tgggtctgga tcctggtctt   2280
```

```
ggcaacccca ggttgcgtcc ttgatgttcc agagcttggt cttctgtgtg gagaagagct   2340

caccatctct acccaacttg agctttggga ccagactccc tttagatcaa accgccccat   2400

ctgtggaaga actacaccag aagtcagcaa gttttcagcc aacagtgctg gcctccccac   2460

ctcccaggct gactagccct ggggagaagg aaccctctcc tcctagacca gcagagactc   2520

cctgggcatg ttcagtgtgg ccccacctcc cttccagtcc cagcttgctt cctccagcta   2580

gcactaactc agcagcatcg ctctgtggac gcctgtaaat tattgagaaa tgtgaactgt   2640

gcagtcttaa agctaaggtg ttagaaaatt tgatttatgc tgtttagttg ttgttgggtt   2700

tcttttcttt ttaatttctt tttctttttt gatttttttt ctttccctta aaacaacagc   2760

agcagcatct tggctctttg tcatgtgttg aatggttggg tcttgtgaag tctgaggtct   2820

aacagtttat tgtcctggaa ggattttctt acagcagaaa cagatttttt tcaaattccc   2880

agaatcctga ggaccaagaa ggatccctca gctgctactt ccagcaccca gcgtcactgg   2940

gacgaaccag gccctgttct tacaaggcca catggctggc cctttgcctc catggctact   3000

gtggtaagtg cagccttgtc tgacccaatg ctgacctaat gttggccatt ccacattgag   3060

gggacaaggt cagtgatgcc ccccttcact cacaagcact tcagaggcat gcagagagaa   3120

gggacactcg gccagctctc tgaggtaatc agtgcaagga ggagtccgtt ttttgccagc   3180

aaacctcagc aggatcacac tggaacagaa cctggtcata cctgtgacaa cacagctgtg   3240

agccagggca aaccacccac tgtcactggc tcgagagtct gggcagaggc tctgaccctc   3300

cacccctttaa actggatgcc ggggcctggc tgggcccaat gccaagtggt tatggcaacc   3360

ctgactatct ggtcttaaca tgtagctcag gaagtggagg cgctaatgtc cccaatccct   3420

ggggattcct gattccagct attcatgtaa gcagagccaa cctgcctatt tctgtaggtg   3480

cgactgggat gttaggagca cagcaaggac ccagctctgt agggctggtg acctgatact   3540

tctcataatg gcatctagaa gttaggctga gttggcctca ctggcccagc aaaccagaac   3600

ttgtctttgt ccgggccatg ttcttgggct gtcttctaat tccaaagggt tggttggtaa   3660

agctccaccc ccttctcctc tgcctaaaga catcacatgt gtatacacac acgggtgtat   3720

agatgagtta aaagaatgtc ctcgctggca tcctaatttt gtcttaagtt tttttggagg   3780

gagaaaggaa caaggcaagg gaagatgtgt agctttggct ttaaccaggc agcctggggg   3840

ctcccaagcc tatggaaccc tggtacaaag aagagaacag aagcgccctg tgaggagtgg   3900

gatttgtttt tctgtagacc agatgagaag gaaacaggcc ctgttttgta catagttgca   3960

acttaaaatt tttggcttgc aaaatatttt tgtaataaag atttctgggt aacaataaaa   4020

aaaaaaaaaa a                                                         4031
```

```
<210> SEQ ID NO 8
<211> LENGTH: 509
<212> TYPE: PRT
<213> ORGANISM: Artificial Sequence
<220> FEATURE:
<223> OTHER INFORMATION: Homo sapiens  and Mus musculus

<400> SEQUENCE: 8

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Glu
            20                  25                  30

Glu Glu Leu Gln Val Ile Gln Pro Asp Lys Ser Val Leu Val Ala Ala
        35                  40                  45
```

```
Gly Glu Thr Ala Thr Leu Arg Cys Thr Ala Thr Ser Leu Ile Pro Val
    50                  55                  60

Gly Pro Ile Gln Trp Phe Arg Gly Ala Gly Pro Gly Arg Glu Leu Ile
65                  70                  75                  80

Tyr Asn Gln Lys Glu Gly His Phe Pro Arg Val Thr Thr Val Ser Asp
                85                  90                  95

Leu Thr Lys Arg Asn Asn Met Asp Phe Ser Ile Arg Ile Gly Asn Ile
            100                 105                 110

Thr Pro Ala Asp Ala Gly Thr Tyr Tyr Cys Val Lys Phe Arg Lys Gly
        115                 120                 125

Ser Pro Asp Asp Val Glu Phe Lys Ser Gly Ala Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Ile Gln Asp Thr Asn Asp Ile Asn
            420                 425                 430

Asp Ile Thr Tyr Ala Asp Leu Asn Leu Pro Lys Glu Lys Lys Pro Ala
        435                 440                 445

Pro Arg Ala Pro Glu Pro Asn Asn His Thr Glu Tyr Ala Ser Ile Glu
    450                 455                 460

Thr Gly Lys Val Pro Arg Pro Glu Asp Thr Leu Thr Tyr Ala Asp Leu
```

```
465                 470                 475                 480

Asp Met Val His Leu Ser Arg Ala Gln Pro Ala Pro Lys Pro Glu Pro
                485                 490                 495

Ser Phe Ser Glu Tyr Ala Ser Val Gln Val Gln Arg Lys
            500                 505


<210> SEQ ID NO 9
<211> LENGTH: 3377
<212> TYPE: DNA
<213> ORGANISM: Mus musculus

<400> SEQUENCE: 9

cgggaaggtg cgggcgcgag gagggggcgc tcggccgggc cgccctcgcg ctggcctcgc     60

gacggctccg cacagcccgc actcgctctg cgagctgtcc ccgctcgcgc ttgctctccg    120

atctccgtcc ccgctccctc tccctcttcc tctccccctc tttccttctc cctcgctatc    180

cgctcccccg cccccgtgcc tctggctctg cgcctggctc cctcgggtcc gctccccttt    240

cccgccggcc tggcccggcg tcacgctccc ggagtctccc cgctcggcgg cgtctcattg    300

tgggaggggg tcagatcacc ccgccgggcg gtggcgctgg ggggcagcgg agggggaggg    360

gccttagtcg ttcgcccgcg ccgcccgccc gcctgccgag cgcgctcacc gccgctctcc    420

ctccttgctc tgcagccgcg gcccatggag cccgccggcc cggcccctgg ccgcctaggg    480

ccgctgctgc tctgcctgct gctctccgcg tcctgtttct gtacaggagc cacggggaag    540

gaactgaagg tgactcagcc tgagaaatca gtgtctgttg ctgctgggga ttcgaccgtt    600

ctgaactgca ctttgacctc cttgttgccg gtgggaccca ttaggtggta cagaggagta    660

gggccaagcc ggctgttgat ctacagtttc gcaggagaat acgttcctcg aattagaaat    720

gtttcagata ctactaagag aaacaatatg gacttttcca tccgtatcag taatgtcacc    780

ccagcagatg ctggcatcta ctactgtgtg aagttccaga aaggatcatc agagcctgac    840

acagaaatac aatctggagg gggaacagag gtctatgtac tcgataataa tgctacccac    900

aactggaatg tcttcatcgg tgtgggcgtg gcgtgtgctt tgctcgtagt cctgctgatg    960

gctgctctct acctcctccg gatcaaacag aagaaagcca aggggtcaac atcttccaca   1020

cggttgcacg agcccgagaa gaacgccagg gaaataaccc agatccagga cacaaatgac   1080

atcaacgaca tcacatacgc agacctgaat ctgcccaaag agaagaagcc cgcacccccgg  1140

gcccctgagc ctaacaacca cacagaatat gcaagcattg agacaggcaa agtgcctagg   1200

ccagaggata ccctcaccta tgctgacctg gacatggtcc acctcagccg ggcacagcca   1260

gcccccaagc ctgagccatc tttctcagag tatgctagtg tccaggtcca gaggaagtga   1320

atggggctgt ggtctgtact aggccccatc cccacaagtt ttcttgtcct acatggagtg   1380

gccatgacga ggacatccag ccagccaatc ctgtccccag aaggccaggt ggcacgggtc   1440

ctaggaccag gggtaagggt ggcctttgtc ttccctccgt ggctcttcaa cacctcttgg   1500

gcacccacgt cccccttcttc cggaggctgg gtgttgcaga accagagggc gaactggaga  1560

aagctgcctg gaatccaaga agtgttgtgc ctcggcccat cactcgtggg tctggatcct   1620

ggtcttggca accccaggtt gcgtccttga tgttccagag cttggtcttc tgtgtggaga   1680

agagctcacc atctctaccc aacttgagct ttgggaccag actcccttta gatcaaaccg   1740

ccccatctgt ggaagaacta caccagaagt cagcaagttt tcagccaaca gtgctggcct   1800

ccccacctcc caggctgact agccctgggg agaaggaacc ctctcctcct agaccagcag   1860

agactccctg ggcatgttca gtgtggcccc acctcccttc cagtcccagc ttgcttcctc   1920
```

```
cagctagcac taactcagca gcatcgctct gtggacgcct gtaaattatt gagaaatgtg   1980

aactgtgcag tcttaaagct aaggtgttag aaaatttgat ttatgctgtt tagttgttgt   2040

tgggtttctt ttctttttaa tttctttttc ttttttgatt ttttttcttt cccttaaaac   2100

aacagcagca gcatcttggc tctttgtcat gtgttgaatg gttgggtctt gtgaagtctg   2160

aggtctaaca gtttattgtc ctggaaggat tttcttacag cagaaacaga tttttttcaa   2220

attcccagaa tcctgaggac caagaaggat ccctcagctg ctacttccag cacccagcgt   2280

cactgggacg aaccaggccc tgttcttaca aggccacatg gctggccctt tgcctccatg   2340

gctactgtgg taagtgcagc cttgtctgac ccaatgctga cctaatgttg gccattccac   2400

attgagggga caaggtcagt gatgcccccc ttcactcaca agcacttcag aggcatgcag   2460

agagaaggga cactcggcca gctctctgag gtaatcagtg caaggaggag tccgtttttt   2520

gccagcaaac ctcagcagga tcacactgga acagaacctg gtcatacctg tgacaacaca   2580

gctgtgagcc agggcaaacc acccactgtc actggctcga gagtctgggc agaggctctg   2640

accctccacc ctttaaactg gatgccgggg cctggctggg cccaatgcca agtggttatg   2700

gcaaccctga ctatctggtc ttaacatgta gctcaggaag tggaggcgct aatgtcccca   2760

atccctgggg attcctgatt ccagctattc atgtaagcag agccaacctg cctatttctg   2820

taggtgcgac tgggatgtta ggagcacagc aaggacccag ctctgtaggg ctggtgacct   2880

gatacttctc ataatggcat ctagaagtta ggctgagttg gcctcactgg cccagcaaac   2940

cagaacttgt ctttgtccgg gccatgttct tgggctgtct tctaattcca aagggttggt   3000

tggtaaagct ccacccccttt ctcctctgcc taaagacatc acatgtgtat acacacacgg   3060

gtgtatagat gagttaaaag aatgtcctcg ctggcatcct aattttgtct taagtttttt   3120

tggagggaga aaggaacaag gcaagggaag atgtgtagct ttggctttaa ccaggcagcc   3180

tgggggctcc caagcctatg gaaccctggt acaaagaaga gaacagaagc gccctgtgag   3240

gagtgggatt tgtttttctg tagaccagat gagaaggaaa caggccctgt tttgtacata   3300

gttgcaactt aaaatttttg gcttgcaaaa tatttttgta ataaagattt ctgggtaaca   3360

ataaaaaaaa aaaaaaa                                                  3377
```

```
<210> SEQ ID NO 10
<211> LENGTH: 291
<212> TYPE: PRT
<213> ORGANISM: Mus musculus

<400> SEQUENCE: 10

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110
```

```
Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Gly Thr Glu Val Tyr
    130                 135                 140

Val Leu Asp Asn Asn Ala Thr His Asn Trp Asn Val Phe Ile Gly Val
145                 150                 155                 160

Gly Val Ala Cys Ala Leu Leu Val Val Leu Leu Met Ala Ala Leu Tyr
                165                 170                 175

Leu Leu Arg Ile Lys Gln Lys Lys Ala Lys Gly Ser Thr Ser Ser Thr
            180                 185                 190

Arg Leu His Glu Pro Glu Lys Asn Ala Arg Glu Ile Thr Gln Ile Gln
        195                 200                 205

Asp Thr Asn Asp Ile Asn Asp Ile Thr Tyr Ala Asp Leu Asn Leu Pro
    210                 215                 220

Lys Glu Lys Lys Pro Ala Pro Arg Ala Pro Glu Pro Asn Asn His Thr
225                 230                 235                 240

Glu Tyr Ala Ser Ile Glu Thr Gly Lys Val Pro Arg Pro Glu Asp Thr
                245                 250                 255

Leu Thr Tyr Ala Asp Leu Asp Met Val His Leu Ser Arg Ala Gln Pro
            260                 265                 270

Ala Pro Lys Pro Glu Pro Ser Phe Ser Glu Tyr Ala Ser Val Gln Val
        275                 280                 285

Gln Arg Lys
    290
```

<210> SEQ ID NO 11
<211> LENGTH: 4043
<212> TYPE: DNA
<213> ORGANISM: Mus musculus

<400> SEQUENCE: 11

```
cgggaaggtg cgggcgcgag gagggggcgc tcggccgggc cgccctcgcg ctggcctcgc      60

gacggctccg cacagcccgc actcgctctg cgagctgtcc ccgctcgcgc ttgctctccg     120

atctccgtcc ccgctccctc tccctcttcc tctccccctc tttccttctc cctcgctatc     180

cgctccccccg cccccgtgcc tctggctctg cgcctggctc cctcgggtcc gctcccccttt   240

cccgccggcc tggcccggcg tcacgctccc ggagtctccc cgctcggcgg cgtctcattg     300

tgggaggggg tcagatcacc ccgccgggcg gtggcgctgg ggggcagcgg agggggaggg     360

gccttagtcg ttcgcccgcg ccgcccgccc gcctgccgag cgcgctcacc gccgctctcc     420

ctccttgctc tgcagccgcg gcccatggag cccgccggcc cggcccctgg ccgcctaggg     480

ccgctgctgc tctgcctgct gctctccgcg tcctgtttct gtacaggagc cacggggaag     540

gaactgaagg tgactcagcc tgagaaatca gtgtctgttg ctgctgggga ttcgaccgtt     600

ctgaactgca ctttgacctc cttgttgccg gtgggaccca ttaggtggta cagaggagta     660

gggccaagcc ggctgttgat ctacagtttc gcaggagaat acgttcctcg aattagaaat     720

gtttcagata ctactaagag aaacaatatg gacttttcca tccgtatcag taatgtcacc     780

ccagcagatg ctggcatcta ctactgtgtg aagttccaga aaggatcatc agagcctgac     840

acagaaatac aatctggagg gggaacagag gtctatgtac tcgccaaacc ttctccaccg     900

gaggtatccg gcccagcaga caggggcata cctgaccaga aagtgaactt cacctgcaag     960

tctcatggct tctctccccg gaatatcacc ctgaagtggt tcaaagatgg gcaagaactc    1020
```

-continued

```
caccccttgg agaccaccgt gaaccctagt ggaaagaatg tctcctacaa catctccagc   1080
acagtcaggg tggtactaaa ctccatggat gttaattcta aggtcatctg cgaggtagcc   1140
cacatcacct tggatagaag ccctcttcgt gggattgcta acctgtctaa cttcatccga   1200
gtttcaccca ccgtgaaggt cacccaacag tccccgacgt caatgaacca ggtgaacctc   1260
acctgccggg ctgagaggtt ctaccccgag gatctccagc tgatctggct ggagaatgga   1320
aacgtatcac ggaatgacac gcccaagaat ctcacaaaga acacggatgg gacctataat   1380
tacacaagct tgttcctggt gaactcatct gctcatagag aggacgtggt gttcacgtgc   1440
caggtgaagc acgaccaaca gccagcgatc acccgaaacc ataccgtgct gggatttgcc   1500
cactcgagtg atcaagggag catgcaaacc ttccctgata ataatgctac ccacaactgg   1560
aatgtcttca tcggtgtggg cgtggcgtgt gctttgctcg tagtcctgct gatggctgct   1620
ctctacctcc tccggatcaa acagaagaaa gccaaggggt caacatcttc cacacggttg   1680
cacgagcccg agaagaacgc cagggaaata acccaggtac agtctttgat ccaggacaca   1740
aatgacatca acgacatcac atacgcagac ctgaatctgc ccaaagagaa gaagcccgca   1800
ccccgggccc ctgagcctaa caaccacaca gaatatgcaa gcattgagac aggcaaagtg   1860
cctaggccag aggataccct cacctatgct gacctggaca tggtccacct cagccgggca   1920
cagccagccc ccaagcctga gccatctttc tcagagtatg ctagtgtcca ggtccagagg   1980
aagtgaatgg ggctgtggtc tgtactaggc cccatcccca caagttttct tgtcctacat   2040
ggagtggcca tgacgaggac atccagccag ccaatcctgt ccccagaagg ccaggtggca   2100
cgggtcctag gaccaggggt aagggtggcc tttgtcttcc ctccgtggct cttcaacacc   2160
tcttgggcac ccacgtcccc ttcttccgga ggctgggtgt tgcagaacca gagggcgaac   2220
tggagaaagc tgcctggaat ccaagaagtg ttgtgcctcg gcccatcact cgtgggtctg   2280
gatcctggtc ttggcaaccc caggttgcgt ccttgatgtt ccagagcttg gtcttctgtg   2340
tggagaagag ctcaccatct ctacccaact tgagctttgg gaccagactc cctttagatc   2400
aaaccgcccc atctgtggaa gaactacacc agaagtcagc aagttttcag ccaacagtgc   2460
tggcctcccc acctcccagg ctgactagcc ctggggagaa ggaaccctct cctcctagac   2520
cagcagagac tccctgggca tgttcagtgt ggccccacct cccttccagt cccagcttgc   2580
ttcctccagc tagcactaac tcagcagcat cgctctgtgg acgcctgtaa attattgaga   2640
aatgtgaact gtgcagtctt aaagctaagg tgttagaaaa tttgatttat gctgtttagt   2700
tgttgttggg tttcttttct ttttaatttc tttttctttt ttgatttttt ttctttccct   2760
taaaacaaca gcagcagcat cttggctctt tgtcatgtgt tgaatggttg ggtcttgtga   2820
agtctgaggt ctaacagttt attgtcctgg aaggattttc ttacagcaga aacagatttt   2880
tttcaaattc ccagaatcct gaggaccaag aaggatccct cagctgctac ttccagcacc   2940
cagcgtcact gggacgaacc aggccctgtt cttacaaggc cacatggctg gccctttgcc   3000
tccatggcta ctgtggtaag tgcagccttg tctgacccaa tgctgaccta atgttggcca   3060
ttccacattg aggggacaag gtcagtgatg ccccccttca ctcacaagca cttcagaggc   3120
atgcagagag aagggacact cggccagctc tctgaggtaa tcagtgcaag gaggagtccg   3180
tttttgcca gcaaacctca gcaggatcac actggaacag aacctggtca tacctgtgac   3240
aacacagctg tgagccaggg caaaccaccc actgtcactg gctcgagagt ctgggcagag   3300
gctctgaccc tccacccttt aaactggatg ccggggcctg gctgggccca atgccaagtg   3360
gttatggcaa ccctgactat ctggtcttaa catgtagctc aggaagtgga ggcgctaatg   3420
```

```
tccccaatcc ctggggattc ctgattccag ctattcatgt aagcagagcc aacctgccta   3480

tttctgtagg tgcgactggg atgttaggag cacagcaagg acccagctct gtagggctgg   3540

tgacctgata cttctcataa tggcatctag aagttaggct gagttggcct cactggccca   3600

gcaaaccaga acttgtcttt gtccgggcca tgttcttggg ctgtcttcta attccaaagg   3660

gttggttggt aaagctccac ccccttctcc tctgcctaaa gacatcacat gtgtatacac   3720

acacgggtgt atagatgagt taaaagaatg tcctcgctgg catcctaatt ttgtcttaag   3780

ttttttgga gggagaaagg aacaaggcaa gggaagatgt gtagctttgg ctttaaccag   3840

gcagcctggg ggctcccaag cctatggaac cctggtacaa agaagagaac agaagcgccc   3900

tgtgaggagt gggatttgtt tttctgtaga ccagatgaga aggaaacagg ccctgttttg   3960

tacatagttg caacttaaaa tttttggctt gcaaaatatt tttgtaataa agatttctgg   4020

gtaacaataa aaaaaaaaaa aaa                                           4043
```

```
<210> SEQ ID NO 12
<211> LENGTH: 513
<212> TYPE: PRT
<213> ORGANISM: Mus musculus

<400> SEQUENCE: 12

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255
```

```
Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Val Gln Ser Leu Ile Gln Asp Thr
            420                 425                 430

Asn Asp Ile Asn Asp Ile Thr Tyr Ala Asp Leu Asn Leu Pro Lys Glu
        435                 440                 445

Lys Lys Pro Ala Pro Arg Ala Pro Glu Pro Asn Asn His Thr Glu Tyr
    450                 455                 460

Ala Ser Ile Glu Thr Gly Lys Val Pro Arg Pro Glu Asp Thr Leu Thr
465                 470                 475                 480

Tyr Ala Asp Leu Asp Met Val His Leu Ser Arg Ala Gln Pro Ala Pro
                485                 490                 495

Lys Pro Glu Pro Ser Phe Ser Glu Tyr Ala Ser Val Gln Val Gln Arg
            500                 505                 510

Lys


<210> SEQ ID NO 13
<211> LENGTH: 3845
<212> TYPE: DNA
<213> ORGANISM: Mus musculus

<400> SEQUENCE: 13

aagctcccct gccgcgggca gcctcttgcc cactggagtc taaggactgg ccgggtgaga      60

ggccgagacc agggggcgat cggccgccac ttccccagtc caccttaaga ggaccaagta     120

gccagcccgc cgcgccgacc tcagaaaaac aagtttgcgc aaagtggtgc gcggccagcc     180

tctgggcaga gggagcggtg cttccaccgc ctggcagccc tgcgcgcggc ggcgcagccg     240

cggcccatgg agcccgccgg cccggcccct ggccgcctag ggccgctgct gctctgcctg     300

ctgctctccg cgtcctgttt ctgtacagga gccacgggga aggaactgaa ggtgactcag     360

cctgagaaat cagtgtctgt tgctgctggg gattcgaccg ttctgaactg cactttgacc     420

tccttgttgc cggtgggacc cattaggtgg tacagaggag tagggccaag ccggctgttg     480

atctacagtt tcgcaggaga atacgttcct cgaattagaa atgtttcaga tactactaag     540

agaaacaata tggacttttc catccgtatc agtaatgtca ccccagcaga tgctggcatc     600

tactactgtg tgaagttcca gaaaggatca tcagagcctg acacagaaat acaatctgga     660
```

```
gggggaacag aggtctatgt actcgccaaa ccttctccac cggaggtatc cggcccagca    720
gacaggggca tacctgacca gaaagtgaac ttcacctgca agtctcatgg cttctctccc    780
cggaatatca ccctgaagtg gttcaaagat gggcaagaac tccacccctt ggagaccacc    840
gtgaacccta gtggaaagaa tgtctcctac aacatctcca gcacagtcag ggtggtacta    900
aactccatgg atgttaattc taaggtcatc tgcgaggtag cccacatcac cttggataga    960
agccctcttc gtgggattgc taacctgtct aacttcatcc gagtttcacc caccgtgaag   1020
gtcacccaac agtccccgac gtcaatgaac caggtgaacc tcacctgccg ggctgagagg   1080
ttctaccccg aggatctcca gctgatctgg ctggagaatg gaaacgtatc acggaatgac   1140
acgcccaaga atctcacaaa gaacacggat gggacctata attacacaag cttgttcctg   1200
gtgaactcat ctgctcatag agaggacgtg gtgttcacgt gccaggtgaa gcacgaccaa   1260
cagccagcga tcacccgaaa ccataccgtg ctgggatttg cccactcgag tgatcaaggg   1320
agcatgcaaa ccttccctga taataatgct acccacaact ggaatgtctt catcggtgtg   1380
ggcgtggcgt gtgctttgct cgtagtcctg ctgatggctg ctctctacct cctccggatc   1440
aaacagaaga aagccaaggg gtcaacatct tccacacggt tgcacgagcc cgagaagaac   1500
gccagggaaa taacccaggt acagtctttg atccaggaca caaatgacat caacgacatc   1560
acatacgcag acctgaatct gcccaaagag aagaagcccg caccccgggc ccctgagcct   1620
aacaaccaca cagaatatgc aagcattgag acaggcaaag tgcctaggcc agaggatacc   1680
ctcacctatg ctgacctgga catggtccac ctcagccggg cacagccagc cccccaagcct  1740
gagccatctt tctcagagta tgctagtgtc caggtccaga ggaagtgaat ggggctgtgg   1800
tctgtactag gccccatccc cacaagtttt cttgtcctac atggagtggc catgacgagg   1860
acatccagcc agccaatcct gtccccagaa ggccaggtgg cacgggtcct aggaccaggg   1920
gtaagggtgg cctttgtctt ccctccgtgg ctcttcaaca cctcttgggc acccacgtcc   1980
ccttcttccg gaggctgggt gttgcagaac cagagggcga actggagaaa gctgcctgga   2040
atccaagaag tgttgtgcct cggcccatca ctcgtgggtc tggatcctgg tcttggcaac   2100
cccaggttgc gtccttgatg ttccagagct tggtcttctg tgtggagaag agctcaccat   2160
ctctacccaa cttgagcttt gggaccagac tccctttaga tcaaaccgcc ccatctgtgg   2220
aagaactaca ccagaagtca gcaagttttc agccaacagt gctggcctcc ccacctccca   2280
ggctgactag ccctggggag aaggaaccct ctcctcctag accagcagag actccctggg   2340
catgttcagt gtggccccac ctcccttcca gtcccagctt gcttcctcca gctagcacta   2400
actcagcagc atcgctctgt ggacgcctgt aaattattga gaaatgtgaa ctgtgcagtc   2460
ttaaagctaa ggtgttagaa aatttgattt atgctgttta gttgttgttg ggtttctttt   2520
ctttttaatt tctttttctt ttttgatttt ttttctttcc cttaaaacaa cagcagcagc   2580
atcttggctc tttgtcatgt gttgaatggt tgggtcttgt gaagtctgag gtctaacagt   2640
ttattgtcct ggaaggattt tcttacagca gaaacagatt tttttcaaat tcccagaatc   2700
ctgaggacca agaaggatcc ctcagctgct acttccagca cccagcgtca ctgggacgaa   2760
ccaggccctg ttcttacaag gccacatggc tggccctttg cctccatggc tactgtggta   2820
agtgcagcct tgtctgaccc aatgctgacc taatgttggc cattccacat tgaggggaca   2880
aggtcagtga tgccccccctt cactcacaag cacttcagag gcatgcagag agaagggaca  2940
ctcggccagc tctctgaggt aatcagtgca aggaggagtc cgttttttgc cagcaaacct   3000
```

```
cagcaggatc acactggaac agaacctggt catacctgtg acaacacagc tgtgagccag   3060

ggcaaaccac ccactgtcac tggctcgaga gtctgggcag aggctctgac cctccaccct   3120

ttaaactgga tgccggggcc tggctgggcc caatgccaag tggttatggc aaccctgact   3180

atctggtctt aacatgtagc tcaggaagtg gaggcgctaa tgtccccaat ccctggggat   3240

tcctgattcc agctattcat gtaagcagag ccaacctgcc tatttctgta ggtgcgactg   3300

ggatgttagg agcacagcaa ggacccagct ctgtagggct ggtgacctga tacttctcat   3360

aatggcatct agaagttagg ctgagttggc ctcactggcc cagcaaacca gaacttgtct   3420

ttgtccgggc catgttcttg ggctgtcttc taattccaaa gggttggttg gtaaagctcc   3480

accccccttct cctctgccta aagacatcac atgtgtatac acacacgggt gtatagatga   3540

gttaaaagaa tgtcctcgct ggcatcctaa ttttgtctta agttttttttg gagggagaaa   3600

ggaacaaggc aagggaagat gtgtagcttt ggctttaacc aggcagcctg gggctccca   3660

agcctatgga accctggtac aaagaagaga acagaagcgc cctgtgagga gtgggatttg   3720

tttttctgta gaccagatga gaaggaaaca ggccctgttt tgtacatagt tgcaacttaa   3780

aatttttggc ttgcaaaata tttttgtaat aaagatttct gggtaacaat aaaaaaaaaa   3840

aaaaa                                                               3845
```

```
<210> SEQ ID NO 14
<211> LENGTH: 513
<212> TYPE: PRT
<213> ORGANISM: Mus musculus

<400> SEQUENCE: 14

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220
```

```
Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Val Gln Ser Leu Ile Gln Asp Thr
            420                 425                 430

Asn Asp Ile Asn Asp Ile Thr Tyr Ala Asp Leu Asn Leu Pro Lys Glu
        435                 440                 445

Lys Lys Pro Ala Pro Arg Ala Pro Glu Pro Asn Asn His Thr Glu Tyr
    450                 455                 460

Ala Ser Ile Glu Thr Gly Lys Val Pro Arg Pro Glu Asp Thr Leu Thr
465                 470                 475                 480

Tyr Ala Asp Leu Asp Met Val His Leu Ser Arg Ala Gln Pro Ala Pro
                485                 490                 495

Lys Pro Glu Pro Ser Phe Ser Glu Tyr Ala Ser Val Gln Val Gln Arg
            500                 505                 510

Lys
```

<210> SEQ ID NO 15
<211> LENGTH: 3389
<212> TYPE: DNA
<213> ORGANISM: Mus musculus

<400> SEQUENCE: 15

```
cgggaaggtg cgggcgcgag gagggggcgc tcggccgggc cgccctcgcg ctggcctcgc      60

gacggctccg cacagcccgc actcgctctg cgagctgtcc ccgctcgcgc ttgctctccg     120

atctccgtcc ccgctccctc tccctcttcc tctccccctc tttccttctc cctcgctatc     180

cgctcccccg cccccgtgcc tctggctctg cgcctggctc cctcgggtcc gctccccttt     240

cccgccggcc tggcccggcg tcacgctccc ggagtctccc cgctcggcgg cgtctcattg     300

tgggaggggg tcagatcacc ccgccgggcg gtggcgctgg ggggcagcgg agggggaggg     360

gccttagtcg ttcgcccgcg ccgcccgccc gcctgccgag cgcgctcacc gccgctctcc     420
```

```
ctccttgctc tgcagccgcg gcccatggag cccgccggcc cggcccctgg ccgcctaggg    480
ccgctgctgc tctgcctgct gctctccgcg tcctgtttct gtacaggagc cacggggaag    540
gaactgaagg tgactcagcc tgagaaatca gtgtctgttg ctgctgggga ttcgaccgtt    600
ctgaactgca ctttgacctc cttgttgccg gtgggaccca ttaggtggta cagaggagta    660
gggccaagcc ggctgttgat ctacagtttc gcaggagaat acgttcctcg aattagaaat    720
gtttcagata ctactaagag aaacaatatg gacttttcca tccgtatcag taatgtcacc    780
ccagcagatg ctggcatcta ctactgtgtg aagttccaga aaggatcatc agagcctgac    840
acagaaatac aatctggagg gggaacagag gtctatgtac tcgataataa tgctacccac    900
aactggaatg tcttcatcgg tgtgggcgtg gcgtgtgctt tgctcgtagt cctgctgatg    960
gctgctctct acctcctccg gatcaaacag aagaaagcca aggggtcaac atcttccaca   1020
cggttgcacg agcccgagaa gaacgccagg gaaataaccc aggtacagtc tttgatccag   1080
gacacaaatg acatcaacga catcacatac gcagacctga atctgcccaa agagaagaag   1140
cccgcacccc gggcccctga gcctaacaac cacacagaat atgcaagcat tgagacaggc   1200
aaagtgccta ggccagagga taccctcacc tatgctgacc tggacatggt ccacctcagc   1260
cgggcacagc cagcccccaa gcctgagcca tctttctcag agtatgctag tgtccaggtc   1320
cagaggaagt gaatggggct gtggtctgta ctaggcccca tccccacaag ttttcttgtc   1380
ctacatggag tggccatgac gaggacatcc agccagccaa tcctgtcccc agaaggccag   1440
gtggcacggg tcctaggacc aggggtaagg gtggcctttg tcttccctcc gtggctcttc   1500
aacacctctt gggcacccac gtccccttct tccggaggct gggtgttgca gaaccagagg   1560
gcgaactgga gaaagctgcc tggaatccaa gaagtgttgt gcctcggccc atcactcgtg   1620
ggtctggatc ctggtcttgg caaccccagg ttgcgtcctt gatgttccag agcttggtct   1680
tctgtgtgga gaagagctca ccatctctac ccaacttgag ctttgggacc agactccctt   1740
tagatcaaac cgccccatct gtggaagaac tacaccagaa gtcagcaagt tttcagccaa   1800
cagtgctggc ctccccacct cccaggctga ctagccctgg ggagaaggaa ccctctcctc   1860
ctagaccagc agagactccc tgggcatgtt cagtgtggcc ccacctccct tccagtccca   1920
gcttgcttcc tccagctagc actaactcag cagcatcgct ctgtggacgc ctgtaaatta   1980
ttgagaaatg tgaactgtgc agtcttaaag ctaaggtgtt agaaaatttg atttatgctg   2040
tttagttgtt gttgggtttc ttttcttttt aatttctttt tctttttttga ttttttttct   2100
ttcccttaaa acaacagcag cagcatcttg gctctttgtc atgtgttgaa tggttgggtc   2160
ttgtgaagtc tgaggtctaa cagtttattg tcctggaagg attttcttac agcagaaaca   2220
gattttttttc aaattcccag aatcctgagg accaagaagg atccctcagc tgctacttcc   2280
agcacccagc gtcactggga cgaaccaggc cctgttctta caaggccaca tggctggccc   2340
tttgcctcca tggctactgt ggtaagtgca gccttgtctg acccaatgct gacctaatgt   2400
tggccattcc acattgaggg gacaaggtca gtgatgcccc ccttcactca caagcacttc   2460
agaggcatgc agagagaagg gacactcggc cagctctctg aggtaatcag tgcaaggagg   2520
agtccgtttt ttgccagcaa acctcagcag gatcacactg gaacagaacc tggtcatacc   2580
tgtgacaaca cagctgtgag ccagggcaaa ccacccactg tcactggctc gagagtctgg   2640
gcagaggctc tgaccctcca ccctttaaac tggatgccgg ggcctggctg ggcccaatgc   2700
caagtggtta tggcaaccct gactatctgg tcttaacatg tagctcagga agtggaggcg   2760
ctaatgtccc caatccctgg ggattcctga ttccagctat tcatgtaagc agagccaacc   2820
```

```
tgcctatttc tgtaggtgcg actgggatgt taggagcaca gcaaggaccc agctctgtag   2880

ggctggtgac ctgatacttc tcataatggc atctagaagt taggctgagt tggcctcact   2940

ggcccagcaa accagaactt gtctttgtcc gggccatgtt cttgggctgt cttctaattc   3000

caaagggttg gttggtaaag ctccaccccc ttctcctctg cctaaagaca tcacatgtgt   3060

atacacacac gggtgtatag atgagttaaa agaatgtcct cgctggcatc ctaattttgt   3120

cttaagtttt tttggaggga gaaaggaaca aggcaaggga agatgtgtag ctttggcttt   3180

aaccaggcag cctgggggct cccaagccta tggaaccctg gtacaaagaa gagaacagaa   3240

gcgccctgtg aggagtggga tttgtttttc tgtagaccag atgagaagga aacaggccct   3300

gttttgtaca tagttgcaac ttaaaatttt tggcttgcaa aatatttttg taataaagat   3360

ttctgggtaa caataaaaaa aaaaaaaaa                                     3389


<210> SEQ ID NO 16
<211> LENGTH: 295
<212> TYPE: PRT
<213> ORGANISM: Mus musculus

<400> SEQUENCE: 16

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Gly Thr Glu Val Tyr
    130                 135                 140

Val Leu Asp Asn Asn Ala Thr His Asn Trp Asn Val Phe Ile Gly Val
145                 150                 155                 160

Gly Val Ala Cys Ala Leu Leu Val Val Leu Leu Met Ala Ala Leu Tyr
                165                 170                 175

Leu Leu Arg Ile Lys Gln Lys Lys Ala Lys Gly Ser Thr Ser Ser Thr
            180                 185                 190

Arg Leu His Glu Pro Glu Lys Asn Ala Arg Glu Ile Thr Gln Val Gln
        195                 200                 205

Ser Leu Ile Gln Asp Thr Asn Asp Ile Asn Asp Ile Thr Tyr Ala Asp
    210                 215                 220

Leu Asn Leu Pro Lys Glu Lys Lys Pro Ala Pro Arg Ala Pro Glu Pro
225                 230                 235                 240

Asn Asn His Thr Glu Tyr Ala Ser Ile Glu Thr Gly Lys Val Pro Arg
                245                 250                 255

Pro Glu Asp Thr Leu Thr Tyr Ala Asp Leu Asp Met Val His Leu Ser
            260                 265                 270
```

```
Arg Ala Gln Pro Ala Pro Lys Pro Glu Pro Ser Phe Ser Glu Tyr Ala
        275                 280                 285

Ser Val Gln Val Gln Arg Lys
    290                 295


<210> SEQ ID NO 17
<211> LENGTH: 876
<212> TYPE: DNA
<213> ORGANISM: Artificial Sequence
<220> FEATURE:
<223> OTHER INFORMATION: Homo sapiens  and Mus musculus

<400> SEQUENCE: 17

atggagcccg ccggcccggc ccctggccgc ctagggccgc tgctgctctg cctgctgctc     60

tccgcgtcct gtttctgtac aggagccacg gggagaggagg agctgcaggt gattcagcct    120

gacaagtccg tgttggttgc agctggagag acagccactc tgcgctgcac tgcgacctct    180

ctgatccctg tggggcccat ccagtggttc agaggagctg gaccaggccg ggaattaatc    240

tacaatcaaa aagaaggcca cttcccccgg gtaacaactg tttcagacct cacaaagaga    300

aacaacatgg acttttccat ccgcatcggt aacatcaccc cagcagatgc cggcacctac    360

tactgtgtga agttccggaa agggagcccc gatgacgtgg agtttaagtc tggagcagga    420

acagaggtct atgtactcga taataatgct acccacaact ggaatgtctt catcggtgtg    480

ggcgtggcgt gtgctttgct cgtagtcctg ctgatggctg ctctctacct cctccggatc    540

aaacagaaga aagccaaggg gtcaacatct tccacacggt tgcacgagcc cgagaagaac    600

gccagggaaa taacccagat ccaggacaca aatgacatca acgacatcac atacgcagac    660

ctgaatctgc ccaaagagaa gaagcccgca ccccgggccc ctgagcctaa caaccacaca    720

gaatatgcaa gcattgagac aggcaaagtg cctaggccag aggataccct cacctatgct    780

gacctggaca tggtccacct cagccgggca cagccagccc ccaagcctga gccatctttc    840

tcagagtatg ctagtgtcca ggtccagagg aagtga                               876


<210> SEQ ID NO 18
<211> LENGTH: 1540
<212> TYPE: DNA
<213> ORGANISM: Artificial Sequence
<220> FEATURE:
<223> OTHER INFORMATION: Homo sapiens  and Mus musculus

<400> SEQUENCE: 18

atggagcccg ccggcccggc ccctggccgc ctagggccgc tgctgctctg cctgctgctc     60

tccgcgtcct gtttctgtac aggagccacg gggagaggagg agctgcaggt gattcagcct    120

gacaagtccg tgttggttgc agctggagag acagccactc tgcgctgcac tgcgacctct    180

ctgatccctg tggggcccat ccagtggttc agaggagctg gaccaggccg ggaattaatc    240

tacaatcaaa aagaaggcca cttcccccgg gtaacaactg tttcagacct cacaaagaga    300

aacaacatgg acttttccat ccgcatcggt aacatcaccc cagcagatgc cggcacctac    360

tactgtgtga agttccggaa agggagcccc gatgacgtgg agtttaagtc tggagcagga    420

acagaggtct atgtactcgc caaaccttct ccaccggagg tatccggccc agcagacagg    480

ggcatacctg accagaaagt gaacttcacc tgcaagtctc atggcttctc tccccggaat    540

atcaccctga agtggttcaa agatgggcaa gaactccacc ccttggagac caccgtgaac    600

cctagtggaa agaatgtctc ctacaacatc tccagcacag tcagggtggt actaaactcc    660
```

```
atggatgtta attctaaggt catctgcgag gtagcccaca tcaccttgga tagaagccct    720
cttcgtggga ttgctaacct gtctaacttc atccgagttt cacccaccgt gaaggtcacc    780
caacagtccc cgacgtcaat gaaccaggtg aacctcacct gccgggctga gaggttctac    840
cccgaggatc tccagctgat ctggctggag aatggaaacg tatcacggaa tgacacgccc    900
aagaatctca caaagaacac ggatgggacc tataattaca caagcttgtt cctggtgaac    960
tcatctgctc atagagagga cgtggtgttc acgtgccagg tgaagcacga ccaacagcca   1020
gcgatcaccc gaaaccatac cgtgctggga tttgcccact cgagtgatca agggagcatg   1080
caaaccttcc ctgataataa tgctacccac aactggaatg tcttcatcgg tgtgggcgtg   1140
gcgtgtgctt tgctcgtagt cctgctgatg gctgctctct acctcctccg gatcaaacag   1200
aagaaagcca aggggtcaac atcttccaca cggttgcacg agcccgagaa gaacgccagg   1260
gaaataaccc aggtacagtc tttgatccag gacacaaatg acatcaacga catcacatac   1320
gcagacctga atctgcccaa agagaagaag cccgcacccc gggcccctga gcctaacaac   1380
cacacagaat atgcaagcat tgagacaggc aaagtgccta ggccagagga taccctcacc   1440
tatgctgacc tggacatggt ccacctcagc cgggcacagc cagcccccaa gcctgagcca   1500
tctttctcag agtatgctag tgtccaggtc cagaggaagt                         1540
```

<210> SEQ ID NO 19
<211> LENGTH: 1540
<212> TYPE: DNA
<213> ORGANISM: Artificial Sequence
<220> FEATURE:
<223> OTHER INFORMATION: Homo sapiens and Mus musculus

<400> SEQUENCE: 19

```
atggagcccg ccggcccggc ccctggccgc ctagggccgc tgctgctctg cctgctgctc     60
tccgcgtcct gtttctgtac aggagccacg gggaggagg agctgcaggt gattcagcct    120
gacaagtccg tgttggttgc agctggagag acagccactc tgcgctgcac tgcgacctct    180
ctgatccctg tggggcccat ccagtggttc agaggagctg gaccaggccg ggaattaatc    240
tacaatcaaa aagaaggcca cttcccccgg gtaacaactg tttcagacct cacaaagaga    300
aacaacatgg acttttccat ccgcatcggt aacatcaccc cagcagatgc cggcacctac    360
tactgtgtga agttccggaa agggagcccc gatgacgtgg agtttaagtc tggagcagga    420
acagaggtct atgtactcgc caaaccttct ccaccggagg tatccggccc agcagacagg    480
ggcatacctg accagaaagt gaacttcacc tgcaagtctc atggcttctc tccccggaat    540
atcaccctga agtggttcaa agatgggcaa gaactccacc ccttggagac caccgtgaac    600
cctagtggaa agaatgtctc ctacaacatc tccagcacag tcagggtggt actaaactcc    660
atggatgtta attctaaggt catctgcgag gtagcccaca tcaccttgga tagaagccct    720
cttcgtggga ttgctaacct gtctaacttc atccgagttt cacccaccgt gaaggtcacc    780
caacagtccc cgacgtcaat gaaccaggtg aacctcacct gccgggctga gaggttctac    840
cccgaggatc tccagctgat ctggctggag aatggaaacg tatcacggaa tgacacgccc    900
aagaatctca caaagaacac ggatgggacc tataattaca caagcttgtt cctggtgaac    960
tcatctgctc atagagagga cgtggtgttc acgtgccagg tgaagcacga ccaacagcca   1020
gcgatcaccc gaaaccatac cgtgctggga tttgcccact cgagtgatca agggagcatg   1080
caaaccttcc ctgataataa tgctacccac aactggaatg tcttcatcgg tgtgggcgtg   1140
gcgtgtgctt tgctcgtagt cctgctgatg gctgctctct acctcctccg gatcaaacag   1200
```

```
aagaaagcca aggggtcaac atcttccaca cggttgcacg agcccgagaa gaacgccagg   1260

gaaataaccc aggtacagtc tttgatccag gacacaaatg acatcaacga catcacatac   1320

gcagacctga atctgcccaa agagaagaag cccgcacccc gggcccctga gcctaacaac   1380

cacacagaat atgcaagcat tgagacaggc aaagtgccta ggccagagga taccctcacc   1440

tatgctgacc tggacatggt ccacctcagc cgggcacagc cagcccccaa gcctgagcca   1500

tctttctcag agtatgctag tgtccaggtc cagaggaagt                         1540
```

<210> SEQ ID NO 20
<211> LENGTH: 888
<212> TYPE: DNA
<213> ORGANISM: Artificial Sequence
<220> FEATURE:
<223> OTHER INFORMATION: Homo sapiens and Mus musculus

<400> SEQUENCE: 20

```
atggagcccg ccggcccggc ccctggccgc ctagggccgc tgctgctctg cctgctgctc     60

tccgcgtcct gtttctgtac aggagccacg gggaggaggg agctgcaggt gattcagcct    120

gacaagtccg tgttggttgc agctggagag acagccactc tgcgctgcac tgcgacctct    180

ctgatccctg tggggcccat ccagtggttc agaggagctg gaccaggccg ggaattaatc    240

tacaatcaaa aagaaggcca cttcccccgg gtaacaactg tttcagacct cacaaagaga    300

aacaacatgg actttttccat ccgcatcggt aacatcaccc cagcagatgc cggcacctac    360

tactgtgtga agttccggaa agggagcccc gatgacgtgg agtttaagtc tggagcagga    420

acagaggtct atgtactcga taataatgct acccacaact ggaatgtctt catcggtgtg    480

ggcgtggcgt gtgctttgct cgtagtcctg ctgatggctg ctctctacct cctccggatc    540

aaacagaaga aagccaaggg gtcaacatct tccacacggt tgcacgagcc cgagaagaac    600

gccagggaaa taacccaggt acagtctttg atccaggaca caaatgacat caacgacatc    660

acatacgcag acctgaatct gcccaaagag aagaagcccg caccccgggc ccctgagcct    720

aacaaccaca cagaatatgc aagcattgag acaggcaaag tgcctaggcc agaggatacc    780

ctcacctatg ctgacctgga catggtccac ctcagccggg cacagccagc ccccaagcct    840

gagccatctt tctcagagta tgctagtgtc caggtccaga ggaagtga                 888
```

<210> SEQ ID NO 21
<211> LENGTH: 3377
<212> TYPE: DNA
<213> ORGANISM: Artificial Sequence
<220> FEATURE:
<223> OTHER INFORMATION: Homo sapiens and Mus musculus

<400> SEQUENCE: 21

```
cgggaaggtg cgggcgcgag gagggggcgc tcggccgggc cgccctcgcg ctggcctcgc     60

gacggctccg cacagcccgc actcgctctg cgagctgtcc ccgctcgcgc ttgctctccg    120

atctccgtcc ccgctccctc tccctcttcc tctccccctc tttccttctc cctcgctatc    180

cgctcccccg cccccgtgcc tctggctctg cgcctggctc cctcgggtcc gctccccttt    240

cccgccggcc tggcccggcg tcacgctccc ggagtctccc cgctcggcgg cgtctcattg    300

tgggaggggg tcagatcacc ccgccgggcg gtggcgctgg ggggcagcgg agggggaggg    360

gccttagtcg ttcgcccgcg ccgcccgccc gcctgccgag cgcgctcacc gccgctctcc    420

ctccttgctc tgcagccgcg gcccatggag cccgccggcc cggcccctgg ccgcctaggg    480
```

```
ccgctgctgc tctgcctgct gctctccgcg tcctgtttct gtacaggagc cacgggggag    540
gaggagctgc aggtgattca gcctgacaag tccgtgttgg ttgcagctgg agagacagcc    600
actctgcgct gcactgcgac ctctctgatc cctgtggggc ccatccagtg gttcagagga    660
gctggaccag gccgggaatt aatctacaat caaaaagaag gccacttccc ccgggtaaca    720
actgtttcag acctcacaaa gagaaacaac atggactttt ccatccgcat cggtaacatc    780
accccagcag atgccggcac ctactactgt gtgaagttcc ggaaagggag ccccgatgac    840
gtggagttta agtctggagc aggaacagag gtctatgtac tcgataataa tgctacccac    900
aactggaatg tcttcatcgg tgtgggcgtg gcgtgtgctt tgctcgtagt cctgctgatg    960
gctgctctct acctcctccg gatcaaacag aagaaagcca aggggtcaac atcttccaca   1020
cggttgcacg agcccgagaa gaacgccagg gaaataaccc agatccagga cacaaatgac   1080
atcaacgaca tcacatacgc agacctgaat ctgcccaaag agaagaagcc cgcacccccgg  1140
gcccctgagc ctaacaacca cacagaatat gcaagcattg agacaggcaa agtgcctagg   1200
ccagaggata ccctcaccta tgctgacctg gacatggtcc acctcagccg ggcacagcca   1260
gcccccaagc ctgagccatc tttctcagag tatgctagtg tccaggtcca gaggaagtga   1320
atggggctgt ggtctgtact aggccccatc cccacaagtt ttcttgtcct acatggagtg   1380
gccatgacga ggacatccag ccagccaatc ctgtccccag aaggccaggt ggcacgggtc   1440
ctaggaccag gggtaagggt ggcctttgtc ttccctccgt ggctcttcaa cacctcttgg   1500
gcacccacgt ccccttcttc cggaggctgg gtgttgcaga accagagggc gaactggaga   1560
aagctgcctg gaatccaaga agtgttgtgc ctcggcccat cactcgtggg tctggatcct   1620
ggtcttggca accccaggtt gcgtccttga tgttccagag cttggtcttc tgtgtggaga   1680
agagctcacc atctctaccc aacttgagct ttgggaccag actcccttta gatcaaaccg   1740
ccccatctgt ggaagaacta caccagaagt cagcaagttt tcagccaaca gtgctggcct   1800
ccccacctcc caggctgact agccctgggg agaaggaacc ctctcctcct agaccagcag   1860
agactccctg ggcatgttca gtgtggcccc acctcccttc cagtcccagc ttgcttcctc   1920
cagctagcac taactcagca gcatcgctct gtggacgcct gtaaattatt gagaaatgtg   1980
aactgtgcag tcttaaagct aaggtgttag aaaatttgat ttatgctgtt tagttgttgt   2040
tgggtttctt ttctttttaa tttctttttc tttttgatt ttttttcttt cccttaaaac    2100
aacagcagca gcatcttggc tctttgtcat gtgttgaatg gttgggtctt gtgaagtctg   2160
aggtctaaca gtttattgtc ctggaaggat tttcttacag cagaaacaga tttttttcaa   2220
attcccagaa tcctgaggac caagaaggat ccctcagctg ctacttccag cacccagcgt   2280
cactgggacg aaccaggccc tgttcttaca aggccacatg gctggccctt tgcctccatg   2340
gctactgtgg taagtgcagc cttgtctgac ccaatgctga cctaatgttg gccattccac   2400
attgagggga caaggtcagt gatgcccccc ttcactcaca agcacttcag aggcatgcag   2460
agagaaggga cactcggcca gctctctgag gtaatcagtg caaggaggag tccgtttttt   2520
gccagcaaac ctcagcagga tcacactgga acagaacctg gtcatacctg tgacaacaca   2580
gctgtgagcc agggcaaacc acccactgtc actggctcga gagtctgggc agaggctctg   2640
accctccacc ctttaaactg gatgccgggg cctggctggg cccaatgcca agtggttatg   2700
gcaaccctga ctatctggtc ttaacatgta gctcaggaag tggaggcgct aatgtcccca   2760
atccctgggg attcctgatt ccagctattc atgtaagcag agccaacctg cctatttctg   2820
taggtgcgac tgggatgtta ggagcacagc aaggacccag ctctgtaggg ctggtgacct   2880
```

```
gatacttctc ataatggcat ctagaagtta ggctgagttg gcctcactgg cccagcaaac   2940
cagaacttgt ctttgtccgg gccatgttct tgggctgtct tctaattcca aagggttggt   3000
tggtaaagct ccaccccctt ctcctctgcc taaagacatc acatgtgtat acacacacgg   3060
gtgtatagat gagttaaaag aatgtcctcg ctggcatcct aattttgtct taagtttttt   3120
tggagggaga aaggaacaag gcaagggaag atgtgtagct ttggctttaa ccaggcagcc   3180
tgggggctcc caagcctatg gaaccctggt acaaagaaga gaacagaagc gccctgtgag   3240
gagtgggatt tgtttttctg tagaccagat gagaaggaaa caggccctgt tttgtacata   3300
gttgcaactt aaaatttttg gcttgcaaaa tatttttgta ataaagattt ctgggtaaca   3360
ataaaaaaaa aaaaaaa                                                  3377
```

```
<210> SEQ ID NO 22
<211> LENGTH: 4043
<212> TYPE: DNA
<213> ORGANISM: Artificial Sequence
<220> FEATURE:
<223> OTHER INFORMATION: Homo sapiens and Mus musculus

<400> SEQUENCE: 22

cgggaaggtg cgggcgcgag gagggggcgc tcggccgggc cgccctcgcg ctggcctcgc     60
gacggctccg cacagcccgc actcgctctg cgagctgtcc ccgctcgcgc ttgctctccg    120
atctccgtcc ccgctccctc tccctcttcc tctccccctc tttccttctc cctcgctatc    180
cgctcccccg cccccgtgcc tctggctctg cgcctggctc cctcgggtcc gctccccttt    240
cccgccggcc tggcccggcg tcacgctccc ggagtctccc cgctcggcgg cgtctcattg    300
tgggaggggg tcagatcacc ccgccgggcg gtggcgctgg ggggcagcgg agggggaggg    360
gccttagtcg ttcgcccgcg ccgcccgccc gcctgccgag cgcgctcacc gccgctctcc    420
ctccttgctc tgcagcccgcg gcccatggag cccgccggcc cggcccctgg ccgcctaggg    480
ccgctgctgc tctgcctgct gctctccgcg tcctgtttct gtacaggagc cacgggggag    540
gaggagctgc aggtgattca gcctgacaag tccgtgttgg ttgcagctgg agagacagcc    600
actctgcgct gcactgcgac ctctctgatc cctgtggggc ccatccagtg gttcagagga    660
gctggaccag gccgggaatt aatctacaat caaaaagaag gccacttccc ccgggtaaca    720
actgtttcag acctcacaaa gagaaacaac atggactttt ccatccgcat cggtaacatc    780
accccagcag atgccggcac ctactactgt gtgaagttcc ggaaagggag ccccgatgac    840
gtggagttta agtctggagc aggaacagag gtctatgtac tcgccaaacc ttctccaccg    900
gaggtatccg gcccagcaga caggggcata cctgaccaga aagtgaactt cacctgcaag    960
tctcatggct tctctccccg gaatatcacc ctgaagtggt tcaaagatgg gcaagaactc   1020
cacccccttgg agaccaccgt gaaccctagt ggaaagaatg tctcctacaa catctccagc  1080
acagtcaggg tggtactaaa ctccatggat gttaattcta aggtcatctg cgaggtagcc   1140
cacatcacct tggatagaag ccctcttcgt gggattgcta acctgtctaa cttcatccga   1200
gtttcaccca ccgtgaaggt cacccaacag tccccgacgt caatgaacca ggtgaacctc   1260
acctgccggg ctgagaggtt ctaccccgag gatctccagc tgatctggct ggagaatgga   1320
aacgtatcac ggaatgacac gcccaagaat ctcacaaaga acacggatgg gacctataat   1380
tacacaagct tgttcctggt gaactcatct gctcatagag aggacgtggt gttcacgtgc   1440
caggtgaagc acgaccaaca gccagcgatc acccgaaacc ataccgtgct gggatttgcc   1500
```

```
cactcgagtg atcaagggag catgcaaacc ttccctgata ataatgctac ccacaactgg   1560
aatgtcttca tcggtgtggg cgtggcgtgt gctttgctcg tagtcctgct gatggctgct   1620
ctctacctcc tccggatcaa acagaagaaa gccaaggggt caacatcttc cacacggttg   1680
cacgagcccg agaagaacgc cagggaaata acccaggtac agtctttgat ccaggacaca   1740
aatgacatca acgacatcac atacgcagac ctgaatctgc ccaaagagaa gaagcccgca   1800
ccccgggccc ctgagcctaa caaccacaca gaatatgcaa gcattgagac aggcaaagtg   1860
cctaggccag aggataccct cacctatgct gacctggaca tggtccacct cagccgggca   1920
cagccagccc ccaagcctga gccatctttc tcagagtatg ctagtgtcca ggtccagagg   1980
aagtgaatgg ggctgtggtc tgtactaggc cccatcccca caagttttct tgtcctacat   2040
ggagtggcca tgacgaggac atccagccag ccaatcctgt ccccagaagg ccaggtggca   2100
cgggtcctag gaccaggggt aagggtggcc tttgtcttcc ctccgtggct cttcaacacc   2160
tcttgggcac ccacgtcccc ttcttccgga ggctgggtgt tgcagaacca gagggcgaac   2220
tggagaaagc tgcctggaat ccaagaagtg ttgtgcctcg gcccatcact cgtgggtctg   2280
gatcctggtc ttggcaaccc caggttgcgt ccttgatgtt ccagagcttg gtcttctgtg   2340
tggagaagag ctcaccatct ctacccaact tgagctttgg gaccagactc cctttagatc   2400
aaaccgcccc atctgtggaa gaactacacc agaagtcagc aagttttcag ccaacagtgc   2460
tggcctcccc acctcccagg ctgactagcc ctggggagaa ggaaccctct cctcctagac   2520
cagcagagac tccctgggca tgttcagtgt ggccccacct cccttccagt cccagcttgc   2580
ttcctccagc tagcactaac tcagcagcat cgctctgtgg acgcctgtaa attattgaga   2640
aatgtgaact gtgcagtctt aaagctaagg tgttagaaaa tttgatttat gctgtttagt   2700
tgttgttggg tttcttttct ttttaatttc tttttctttt ttgatttttt ttctttccct   2760
taaaacaaca gcagcagcat cttggctctt tgtcatgtgt tgaatggttg ggtcttgtga   2820
agtctgaggt ctaacagttt attgtcctgg aaggattttc ttacagcaga aacagatttt   2880
tttcaaattc ccagaatcct gaggaccaag aaggatccct cagctgctac ttccagcacc   2940
cagcgtcact gggacgaacc aggccctgtt cttacaaggc cacatggctg gccctttgcc   3000
tccatggcta ctgtggtaag tgcagccttg tctgacccaa tgctgaccta atgttggcca   3060
ttccacattg aggggacaag gtcagtgatg ccccccttca ctcacaagca cttcagaggc   3120
atgcagagag aagggacact cggccagctc tctgaggtaa tcagtgcaag gaggagtccg   3180
tttttgcca gcaaacctca gcaggatcac actggaacag aacctggtca tacctgtgac   3240
aacacagctg tgagccaggg caaaccaccc actgtcactg gctcgagagt ctgggcagag   3300
gctctgaccc tccacccttt aaactggatg ccggggcctg gctgggccca atgccaagtg   3360
gttatggcaa ccctgactat ctggtcttaa catgtagctc aggaagtgga ggcgctaatg   3420
tccccaatcc ctggggattc ctgattccag ctattcatgt aagcagagcc aacctgccta   3480
tttctgtagg tgcgactggg atgttaggag cacagcaagg acccagctct gtagggctgg   3540
tgacctgata cttctcataa tggcatctag aagttaggct gagttggcct cactggccca   3600
gcaaaccaga acttgtcttt gtccgggcca tgttcttggg ctgtcttcta attccaaagg   3660
gttggttggt aaagctccac ccccttctcc tctgcctaaa gacatcacat gtgtatacac   3720
acacgggtgt atagatgagt taaaagaatg tcctcgctgg catcctaatt ttgtcttaag   3780
tttttttgga gggagaaagg aacaaggcaa gggaagatgt gtagctttgg ctttaaccag   3840
gcagcctggg ggctcccaag cctatggaac cctggtacaa agaagagaac agaagcgccc   3900
```

tgtgaggagt gggatttgtt tttctgtaga ccagatgaga aggaaacagg ccctgttttg 3960
tacatagttg caacttaaaa tttttggctt gcaaaatatt tttgtaataa agatttctgg 4020
gtaacaataa aaaaaaaaaa aaa 4043

<210> SEQ ID NO 23
<211> LENGTH: 3845
<212> TYPE: DNA
<213> ORGANISM: Artificial Sequence
<220> FEATURE:
<223> OTHER INFORMATION: Homo sapiens and Mus musculus

<400> SEQUENCE: 23
aagctcccct gccgcgggca gcctcttgcc cactggagtc taaggactgg ccgggtgaga 60
ggccgagacc agggggcgat cggccgccac ttccccagtc caccttaaga ggaccaagta 120
gccagcccgc cgcgccgacc tcagaaaaac aagtttgcgc aaagtggtgc gcggccagcc 180
tctgggcaga gggagcggtg cttccaccgc ctggcagccc tgcgcgcggc ggcgcagccg 240
cggcccatgg agcccgccgg cccggcccct ggccgcctag ggccgctgct gctctgcctg 300
ctgctctccg cgtcctgttt ctgtacagga gccacggggg aggaggagct gcaggtgatt 360
cagcctgaca agtccgtgtt ggttgcagct ggagagacag ccactctgcg ctgcactgcg 420
acctctctga tccctgtggg gcccatccag tggttcagag gagctggacc aggccgggaa 480
ttaatctaca atcaaaaaga aggccacttc ccccgggtaa caactgtttc agacctcaca 540
aagagaaaca acatggactt ttccatccgc atcggtaaca tcaccccagc agatgccggc 600
acctactact gtgtgaagtt ccggaaaggg agccccgatg acgtggagtt taagtctgga 660
gcaggaacag aggtctatgt actcgccaaa ccttctccac cggaggtatc cggcccagca 720
gacaggggca tacctgacca gaaagtgaac ttcacctgca agtctcatgg cttctctccc 780
cggaatatca ccctgaagtg gttcaaagat gggcaagaac tccacccctt ggagaccacc 840
gtgaacccta gtggaaagaa tgtctcctac aacatctcca gcacagtcag ggtggtacta 900
aactccatgg atgttaattc taaggtcatc tgcgaggtag cccacatcac cttggataga 960
agccctcttc gtgggattgc taacctgtct aacttcatcc gagtttcacc caccgtgaag 1020
gtcacccaac agtccccgac gtcaatgaac caggtgaacc tcacctgccg ggctgagagg 1080
ttctaccccg aggatctcca gctgatctgg ctggagaatg gaaacgtatc acggaatgac 1140
acgcccaaga atctcacaaa gaacacggat gggacctata attacacaag cttgttcctg 1200
gtgaactcat ctgctcatag agaggacgtg gtgttcacgt gccaggtgaa gcacgaccaa 1260
cagccagcga tcacccgaaa ccataccgtg ctgggatttg cccactcgag tgatcaaggg 1320
agcatgcaaa ccttccctga taataatgct acccacaact ggaatgtctt catcggtgtg 1380
ggcgtggcgt gtgctttgct cgtagtcctg ctgatggctg ctctctacct cctccggatc 1440
aaacagaaga aagccaaggg gtcaacatct tccacacggt tgcacgagcc cgagaagaac 1500
gccagggaaa taacccaggt acagtctttg atccaggaca caaatgacat caacgacatc 1560
acatacgcag acctgaatct gcccaaagag aagaagcccg caccccgggc ccctgagcct 1620
aacaaccaca cagaatatgc aagcattgag acaggcaaag tgcctaggcc agaggatacc 1680
ctcacctatg ctgacctgga catggtccac ctcagccggg cacagccagc ccccaagcct 1740
gagccatctt tctcagagta tgctagtgtc caggtccaga ggaagtgaat ggggctgtgg 1800
tctgtactag gccccatccc cacaagtttt cttgtcctac atggagtggc catgacgagg 1860

```
acatccagcc agccaatcct gtccccagaa ggccaggtgg cacgggtcct aggaccaggg   1920

gtaagggtgg cctttgtctt ccctccgtgg ctcttcaaca cctcttgggc acccacgtcc   1980

ccttcttccg gaggctgggt gttgcagaac cagagggcga actggagaaa gctgcctgga   2040

atccaagaag tgttgtgcct cggcccatca ctcgtgggtc tggatcctgg tcttggcaac   2100

cccaggttgc gtccttgatg ttccagagct tggtcttctg tgtggagaag agctcaccat   2160

ctctacccaa cttgagcttt gggaccagac tccctttaga tcaaaccgcc ccatctgtgg   2220

aagaactaca ccagaagtca gcaagttttc agccaacagt gctggcctcc ccacctccca   2280

ggctgactag ccctggggag aaggaaccct ctcctcctag accagcagag actccctggg   2340

catgttcagt gtggccccac ctcccttcca gtcccagctt gcttcctcca gctagcacta   2400

actcagcagc atcgctctgt ggacgcctgt aaattattga gaaatgtgaa ctgtgcagtc   2460

ttaaagctaa ggtgttagaa aatttgattt atgctgttta gttgttgttg ggtttctttt   2520

ctttttaatt tctttttctt ttttgatttt ttttctttcc cttaaaacaa cagcagcagc   2580

atcttggctc tttgtcatgt gttgaatggt tgggtcttgt gaagtctgag gtctaacagt   2640

ttattgtcct ggaaggattt tcttacagca gaaacagatt tttttcaaat tcccagaatc   2700

ctgaggacca agaaggatcc ctcagctgct acttccagca cccagcgtca ctgggacgaa   2760

ccaggccctg ttcttacaag gccacatggc tggccctttg cctccatggc tactgtggta   2820

agtgcagcct tgtctgaccc aatgctgacc taatgttggc cattccacat tgaggggaca   2880

aggtcagtga tgcccccctt cactcacaag cacttcagag gcatgcagag agaagggaca   2940

ctcggccagc tctctgaggt aatcagtgca aggaggagtc cgtttttttgc cagcaaacct   3000

cagcaggatc acactggaac agaacctggt catacctgtg acaacacagc tgtgagccag   3060

ggcaaaccac ccactgtcac tggctcgaga gtctgggcag aggctctgac cctccaccct   3120

ttaaactgga tgccggggcc tggctgggcc caatgccaag tggttatggc aaccctgact   3180

atctggtctt aacatgtagc tcaggaagtg gaggcgctaa tgtccccaat ccctggggat   3240

tcctgattcc agctattcat gtaagcagag ccaacctgcc tatttctgta ggtgcgactg   3300

ggatgttagg agcacagcaa ggacccagct ctgtagggct ggtgacctga tacttctcat   3360

aatggcatct agaagttagg ctgagttggc ctcactggcc cagcaaacca gaacttgtct   3420

ttgtccgggc catgttcttg ggctgtcttc taattccaaa gggttggttg gtaaagctcc   3480

accccccttct cctctgccta aagacatcac atgtgtatac acacacgggt gtatagatga   3540

gttaaaagaa tgtcctcgct ggcatcctaa ttttgtctta agttttttttg gagggagaaa   3600

ggaacaaggc aagggaagat gtgtagcttt ggctttaacc aggcagcctg ggggctccca   3660

agcctatgga accctggtac aaagaagaga acagaagcgc cctgtgagga gtgggatttg   3720

tttttctgta gaccagatga gaaggaaaca ggccctgttt tgtacatagt tgcaacttaa   3780

aatttttggc ttgcaaaata tttttgtaat aaagatttct gggtaacaat aaaaaaaaaa   3840

aaaaa                                                               3845
```

<210> SEQ ID NO 24
<211> LENGTH: 3389
<212> TYPE: DNA
<213> ORGANISM: Artificial Sequence
<220> FEATURE:
<223> OTHER INFORMATION: Homo sapiens and Mus musculus

<400> SEQUENCE: 24

```
cgggaaggtg cgggcgcgag gagggggcgc tcggccgggc cgccctcgcg ctggcctcgc     60
```

```
gacggctccg cacagcccgc actcgctctg cgagctgtcc ccgctcgcgc ttgctctccg    120
atctccgtcc ccgctccctc tccctcttcc tctccccctc tttccttctc cctcgctatc    180
cgctcccccg cccccgtgcc tctggctctg cgcctggctc cctcgggtcc gctccccttt    240
cccgccggcc tggcccggcg tcacgctccc ggagtctccc cgctcggcgg cgtctcattg    300
tgggaggggg tcagatcacc ccgccgggcg gtggcgctgg ggggcagcgg agggggaggg    360
gccttagtcg ttcgcccgcg ccgcccgccc gcctgccgag cgcgctcacc gccgctctcc    420
ctccttgctc tgcagccgcg gcccatggag cccgccggcc cggcccctgg ccgcctaggg    480
ccgctgctgc tctgcctgct gctctccgcg tcctgtttct gtacaggagc cacgggggag    540
gaggagctgc aggtgattca gcctgacaag tccgtgttgg ttgcagctgg agagacagcc    600
actctgcgct gcactgcgac ctctctgatc cctgtggggc ccatccagtg gttcagagga    660
gctggaccag gccgggaatt aatctacaat caaaaagaag gccacttccc ccgggtaaca    720
actgtttcag acctcacaaa gagaaacaac atggactttt ccatccgcat cggtaacatc    780
accccagcag atgccggcac ctactactgt gtgaagttcc ggaaagggag ccccgatgac    840
gtggagttta agtctggagc aggaacagag gtctatgtac tcgataataa tgctacccac    900
aactggaatg tcttcatcgg tgtgggcgtg gcgtgtgctt tgctcgtagt cctgctgatg    960
gctgctctct acctcctccg gatcaaacag aagaaagcca aggggtcaac atcttccaca   1020
cggttgcacg agcccgagaa gaacgccagg gaaataaccc aggtacagtc tttgatccag   1080
gacacaaatg acatcaacga catcacatac gcagacctga atctgcccaa agagaagaag   1140
cccgcacccc gggcccctga gcctaacaac cacacagaat atgcaagcat tgagacaggc   1200
aaagtgccta ggccagagga taccctcacc tatgctgacc tggacatggt ccacctcagc   1260
cgggcacagc cagcccccaa gcctgagcca tctttctcag agtatgctag tgtccaggtc   1320
cagaggaagt gaatggggct gtggtctgta ctaggcccca tccccacaag ttttcttgtc   1380
ctacatggag tggccatgac gaggacatcc agccagccaa tcctgtcccc agaaggccag   1440
gtggcacggg tcctaggacc aggggtaagg gtggcctttg tcttccctcc gtggctcttc   1500
aacacctctt gggcacccac gtccccttct tccggaggct gggtgttgca gaaccagagg   1560
gcgaactgga gaaagctgcc tggaatccaa gaagtgttgt gcctcggccc atcactcgtg   1620
ggtctggatc ctggtcttgg caaccccagg ttgcgtcctt gatgttccag agcttggtct   1680
tctgtgtgga gaagagctca ccatctctac ccaacttgag ctttgggacc agactccctt   1740
tagatcaaac cgcccccatct gtggaagaac tacaccagaa gtcagcaagt tttcagccaa   1800
cagtgctggc ctccccacct cccaggctga ctagccctgg ggagaaggaa ccctctcctc   1860
ctagaccagc agagactccc tgggcatgtt cagtgtggcc ccacctccct tccagtccca   1920
gcttgcttcc tccagctagc actaactcag cagcatcgct ctgtggacgc ctgtaaatta   1980
ttgagaaatg tgaactgtgc agtcttaaag ctaaggtgtt agaaaatttg atttatgctg   2040
tttagttgtt gttgggtttc ttttcttttt aatttctttt tctttttga ttttttttct   2100
ttcccttaaa acaacagcag cagcatcttg gctctttgtc atgtgttgaa tggttgggtc   2160
ttgtgaagtc tgaggtctaa cagtttattg tcctggaagg attttcttac agcagaaaca   2220
gatttttttc aaattcccag aatcctgagg accaagaagg atccctcagc tgctacttcc   2280
agcacccagc gtcactggga cgaaccaggc cctgttctta caaggccaca tggctggccc   2340
tttgcctcca tggctactgt ggtaagtgca gccttgtctg acccaatgct gacctaatgt   2400
```

```
tggccattcc acattgaggg gacaaggtca gtgatgcccc ccttcactca caagcacttc   2460

agaggcatgc agagagaagg gacactcggc cagctctctg aggtaatcag tgcaaggagg   2520

agtccgtttt ttgccagcaa acctcagcag gatcacactg gaacagaacc tggtcatacc   2580

tgtgacaaca cagctgtgag ccagggcaaa ccacccactg tcactggctc gagagtctgg   2640

gcagaggctc tgaccctcca ccctttaaac tggatgccgg ggcctggctg ggcccaatgc   2700

caagtggtta tggcaaccct gactatctgg tcttaacatg tagctcagga agtggaggcg   2760

ctaatgtccc caatccctgg ggattcctga ttccagctat tcatgtaagc agagccaacc   2820

tgcctatttc tgtaggtgcg actgggatgt taggagcaca gcaaggaccc agctctgtag   2880

ggctggtgac ctgatacttc tcataatggc atctagaagt taggctgagt tggcctcact   2940

ggcccagcaa accagaactt gtctttgtcc gggccatgtt cttgggctgt cttctaattc   3000

caaagggttg gttggtaaag ctccaccccc ttctcctctg cctaaagaca tcacatgtgt   3060

atacacacac gggtgtatag atgagttaaa agaatgtcct cgctggcatc ctaattttgt   3120

cttaagtttt tttggaggga gaaaggaaca aggcaaggga agatgtgtag ctttggcttt   3180

aaccaggcag cctgggggct cccaagccta tggaaccctg gtacaaagaa gagaacagaa   3240

gcgccctgtg aggagtggga tttgtttttc tgtagaccag atgagaagga aacaggccct   3300

gttttgtaca tagttgcaac ttaaaatttt tggcttgcaa aatatttttg taataaagat   3360

ttctgggtaa caataaaaaa aaaaaaaaa                                      3389


<210> SEQ ID NO 25
<211> LENGTH: 291
<212> TYPE: PRT
<213> ORGANISM: Artificial Sequence
<220> FEATURE:
<223> OTHER INFORMATION: Homo sapiens and Mus musculus

<400> SEQUENCE: 25

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Glu
            20                  25                  30

Glu Glu Leu Gln Val Ile Gln Pro Asp Lys Ser Val Leu Val Ala Ala
        35                  40                  45

Gly Glu Thr Ala Thr Leu Arg Cys Thr Ala Thr Ser Leu Ile Pro Val
    50                  55                  60

Gly Pro Ile Gln Trp Phe Arg Gly Ala Gly Pro Gly Arg Glu Leu Ile
65                  70                  75                  80

Tyr Asn Gln Lys Glu Gly His Phe Pro Arg Val Thr Thr Val Ser Asp
                85                  90                  95

Leu Thr Lys Arg Asn Asn Met Asp Phe Ser Ile Arg Ile Gly Asn Ile
            100                 105                 110

Thr Pro Ala Asp Ala Gly Thr Tyr Tyr Cys Val Lys Phe Arg Lys Gly
        115                 120                 125

Ser Pro Asp Asp Val Glu Phe Lys Ser Gly Ala Gly Thr Glu Val Tyr
    130                 135                 140

Val Leu Asp Asn Asn Ala Thr His Asn Trp Asn Val Phe Ile Gly Val
145                 150                 155                 160

Gly Val Ala Cys Ala Leu Leu Val Val Leu Leu Met Ala Ala Leu Tyr
                165                 170                 175

Leu Leu Arg Ile Lys Gln Lys Lys Ala Lys Gly Ser Thr Ser Ser Thr
            180                 185                 190
```

```
Arg Leu His Glu Pro Glu Lys Asn Ala Arg Glu Ile Thr Gln Ile Gln
        195                 200                 205

Asp Thr Asn Asp Ile Asn Asp Ile Thr Tyr Ala Asp Leu Asn Leu Pro
    210                 215                 220

Lys Glu Lys Lys Pro Ala Pro Arg Ala Pro Glu Pro Asn Asn His Thr
225                 230                 235                 240

Glu Tyr Ala Ser Ile Glu Thr Gly Lys Val Pro Arg Pro Glu Asp Thr
                245                 250                 255

Leu Thr Tyr Ala Asp Leu Asp Met Val His Leu Ser Arg Ala Gln Pro
            260                 265                 270

Ala Pro Lys Pro Glu Pro Ser Phe Ser Glu Tyr Ala Ser Val Gln Val
        275                 280                 285

Gln Arg Lys
    290


<210> SEQ ID NO 26
<211> LENGTH: 513
<212> TYPE: PRT
<213> ORGANISM: Artificial Sequence
<220> FEATURE:
<223> OTHER INFORMATION: Homo sapiens and Mus musculus

<400> SEQUENCE: 26

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Glu
            20                  25                  30

Glu Glu Leu Gln Val Ile Gln Pro Asp Lys Ser Val Leu Val Ala Ala
        35                  40                  45

Gly Glu Thr Ala Thr Leu Arg Cys Thr Ala Thr Ser Leu Ile Pro Val
    50                  55                  60

Gly Pro Ile Gln Trp Phe Arg Gly Ala Gly Pro Gly Arg Glu Leu Ile
65                  70                  75                  80

Tyr Asn Gln Lys Glu Gly His Phe Pro Arg Val Thr Thr Val Ser Asp
                85                  90                  95

Leu Thr Lys Arg Asn Asn Met Asp Phe Ser Ile Arg Ile Gly Asn Ile
            100                 105                 110

Thr Pro Ala Asp Ala Gly Thr Tyr Tyr Cys Val Lys Phe Arg Lys Gly
        115                 120                 125

Ser Pro Asp Asp Val Glu Phe Lys Ser Gly Ala Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255
```

```
Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Val Gln Ser Leu Ile Gln Asp Thr
            420                 425                 430

Asn Asp Ile Asn Asp Ile Thr Tyr Ala Asp Leu Asn Leu Pro Lys Glu
        435                 440                 445

Lys Lys Pro Ala Pro Arg Ala Pro Glu Pro Asn Asn His Thr Glu Tyr
    450                 455                 460

Ala Ser Ile Glu Thr Gly Lys Val Pro Arg Pro Glu Asp Thr Leu Thr
465                 470                 475                 480

Tyr Ala Asp Leu Asp Met Val His Leu Ser Arg Ala Gln Pro Ala Pro
                485                 490                 495

Lys Pro Glu Pro Ser Phe Ser Glu Tyr Ala Ser Val Gln Val Gln Arg
            500                 505                 510

Lys
```

<210> SEQ ID NO 27
<211> LENGTH: 513
<212> TYPE: PRT
<213> ORGANISM: Artificial Sequence
<220> FEATURE:
<223> OTHER INFORMATION: Homo sapiens and Mus musculus

<400> SEQUENCE: 27

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Glu
            20                  25                  30

Glu Glu Leu Gln Val Ile Gln Pro Asp Lys Ser Val Leu Val Ala Ala
        35                  40                  45

Gly Glu Thr Ala Thr Leu Arg Cys Thr Ala Thr Ser Leu Ile Pro Val
    50                  55                  60

Gly Pro Ile Gln Trp Phe Arg Gly Ala Gly Pro Gly Arg Glu Leu Ile
65                  70                  75                  80

Tyr Asn Gln Lys Glu Gly His Phe Pro Arg Val Thr Thr Val Ser Asp
                85                  90                  95
```

```
Leu Thr Lys Arg Asn Asn Met Asp Phe Ser Ile Arg Ile Gly Asn Ile
            100                 105                 110

Thr Pro Ala Asp Ala Gly Thr Tyr Tyr Cys Val Lys Phe Arg Lys Gly
        115                 120                 125

Ser Pro Asp Asp Val Glu Phe Lys Ser Gly Ala Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Val Gln Ser Leu Ile Gln Asp Thr
            420                 425                 430

Asn Asp Ile Asn Asp Ile Thr Tyr Ala Asp Leu Asn Leu Pro Lys Glu
        435                 440                 445

Lys Lys Pro Ala Pro Arg Ala Pro Glu Pro Asn Asn His Thr Glu Tyr
    450                 455                 460

Ala Ser Ile Glu Thr Gly Lys Val Pro Arg Pro Glu Asp Thr Leu Thr
465                 470                 475                 480

Tyr Ala Asp Leu Asp Met Val His Leu Ser Arg Ala Gln Pro Ala Pro
                485                 490                 495

Lys Pro Glu Pro Ser Phe Ser Glu Tyr Ala Ser Val Gln Val Gln Arg
            500                 505                 510

Lys
```

<210> SEQ ID NO 28
<211> LENGTH: 295
<212> TYPE: PRT
<213> ORGANISM: Artificial Sequence
<220> FEATURE:
<223> OTHER INFORMATION: Homo sapiens and Mus musculus

<400> SEQUENCE: 28

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Glu
            20                  25                  30

Glu Glu Leu Gln Val Ile Gln Pro Asp Lys Ser Val Leu Val Ala Ala
        35                  40                  45

Gly Glu Thr Ala Thr Leu Arg Cys Thr Ala Thr Ser Leu Ile Pro Val
    50                  55                  60

Gly Pro Ile Gln Trp Phe Arg Gly Ala Gly Pro Gly Arg Glu Leu Ile
65                  70                  75                  80

Tyr Asn Gln Lys Glu Gly His Phe Pro Arg Val Thr Thr Val Ser Asp
                85                  90                  95

Leu Thr Lys Arg Asn Asn Met Asp Phe Ser Ile Arg Ile Gly Asn Ile
            100                 105                 110

Thr Pro Ala Asp Ala Gly Thr Tyr Tyr Cys Val Lys Phe Arg Lys Gly
        115                 120                 125

Ser Pro Asp Asp Val Glu Phe Lys Ser Gly Ala Gly Thr Glu Val Tyr
    130                 135                 140

Val Leu Asp Asn Asn Ala Thr His Asn Trp Asn Val Phe Ile Gly Val
145                 150                 155                 160

Gly Val Ala Cys Ala Leu Leu Val Val Leu Leu Met Ala Ala Leu Tyr
                165                 170                 175

Leu Leu Arg Ile Lys Gln Lys Lys Ala Lys Gly Ser Thr Ser Ser Thr
            180                 185                 190

Arg Leu His Glu Pro Glu Lys Asn Ala Arg Glu Ile Thr Gln Val Gln
        195                 200                 205

Ser Leu Ile Gln Asp Thr Asn Asp Ile Asn Asp Ile Thr Tyr Ala Asp
    210                 215                 220

Leu Asn Leu Pro Lys Glu Lys Lys Pro Ala Pro Arg Ala Pro Glu Pro
225                 230                 235                 240

Asn Asn His Thr Glu Tyr Ala Ser Ile Glu Thr Gly Lys Val Pro Arg
                245                 250                 255

Pro Glu Asp Thr Leu Thr Tyr Ala Asp Leu Asp Met Val His Leu Ser
            260                 265                 270

Arg Ala Gln Pro Ala Pro Lys Pro Glu Pro Ser Phe Ser Glu Tyr Ala
        275                 280                 285

Ser Val Gln Val Gln Arg Lys
    290                 295
```

<210> SEQ ID NO 29
<211> LENGTH: 1569
<212> TYPE: DNA
<213> ORGANISM: Artificial Sequence
<220> FEATURE:
<223> OTHER INFORMATION: Mus musculus

<400> SEQUENCE: 29

```
cacatctgcc atgaaaattg gatctcaagg caagccctgg ctggggaaga aggagaggca     60
```

```
ggacagtgag caactgatga caggcccatc ccagggctct gagtgcttgc agtgacagca    120
gagctgatcc atggacctcc ccgccttagg ctctctccct ttgacagtgc agcaacacca    180
ggccattggc agataggcaa acacagtctc ttttactctg ccaacacaag aggggctacc    240
caaggatcct gctacagccc tgtctaatag acagagtcac attagaagct ggtggggatc    300
ccagttgggg accaagatca cctgactcac tgttgcagtc tgccactctt gctatcttcg    360
tcctcccttt cctgtcctcc cgtctgggcc actgtgtctc taatgtctat gtgtctgaat    420
gctcatgttc tacatccata agttcagcaa accatggttc aggaaggtag ttaggccact    480
gtgcttgggt ggcaaggatt ttaatccatt gaatcatccc ctagatgctg ctttttaaaa    540
atgacttatt ttattttaat tatgtatatc tattggtatg catgtgtgtg ggcacttgtg    600
aaggctagaa gcccctggat cccctgcact tggacgtaca gaccacatga tataagtgct    660
gggtatcgat cctgggtcct ctggaagatc agccagtgct cttaaccgct ggccatttct    720
ccagcccaga tgctgctttt taactcacca acttcagttt gtttgtttgt ttgtttgttt    780
gtattagaag tacatcaaga tgggctcatg ctacacattt cacagaaatg aaggccatca    840
aaaaccctgt ccatgctaaa gccacaactc cacagcattt ggcagagggt gagcacctgg    900
gcctactgat gactccaagt gatgcagcct tatgctaccg agccacacct aagacccagg    960
ttctcagctc tcctaccact agactgctga gacccgctgc tctgctcagg actcgatttc   1020
cagtacacaa tctccctctt tgaaaagtac cacacatcct ggggtctcct ccatctgtat   1080
ctctgctggg tttgttccct ctgtggggaa ttcacgctcc cattataact gacaaattca   1140
ggccgggcgt ggtggcacac gcctttaatc ccagcactcg ggagacagag gcaggcggat   1200
ttctgagttc gaggccagcc tggtctacag agtgagttcc aggacagcca gggctataca   1260
gagaaaccct gtctcgaaaa aaaccaaaat aaataagtaa gtaactgaca agttcagctc   1320
agacatgaca cttctccaaa gggcttgggc actctactat gctaagctat gtggcttagc   1380
actctgtgct ttagttttct tattagtctt gagttacagg ctcatgtggg gaataacaca   1440
tgctgaactt tgtgctgaac tcaataacat tgtgtgtgct caatcagtga aaatcattga   1500
taaacctgag cctgcaggat cccttaaggt tagtcatggc tgccatcttt cttcccagga   1560
gccacgggg                                                           1569
```

```
<210> SEQ ID NO 30
<211> LENGTH: 1400
<212> TYPE: DNA
<213> ORGANISM: Artificial Sequence
<220> FEATURE:
<223> OTHER INFORMATION: Mus musculus

<400> SEQUENCE: 30

ggaacagagg tctatgtact cggtaagtaa gcctgtgcct tcttcatacc ctgatgtgta     60
gcatcaggtc agagaataac atcttggatc tcgtaagtgt ggctcgcagc aggtataatg    120
ggaggtcagg ttcatgatct aagctcaacc ttcaacagat cagagaagct gaggccaggt    180
gttagctcaa ggttccagtg ctagcaagaa agaaggcatc tgcatccctc atatgcccac    240
cccacagccc tctcttcctt gcccatggtt caagtaccag tgaataccag aatgcagatc    300
ccggcaggct ccttgctgcc caggcattaa gcatccccac aggtgagccc aggacacagg    360
agatgctgag aaagttctga acctctagga aacccagact ctccaccgtc acttacacaa    420
agactcagga taccctctcc attcagaagt cagggcctgt cagtgactgg gaaagctctc    480
```

```
ccaaatgcca ggcaggacac aaagcacccc tccattatgt gaatgcctcc attttactct    540

agcatctaga aattccacaa tttattgtag tcttctgttt gtagagaatt cagttcttcc    600

aaactgtgga cttttacaat agtgctgcac tggatgctca tcccacttgt ctaggacaga    660

gacgcccact gtgcaaggcc tacatcacat agctgtgttc gttttaattt gtatagatga    720

tagcagtttt ccctccaggc agcaaccaag tctccttgtc acctctgcac aaaagcaggg    780

caggtagctt atcctgatat gacagacact gaagctccca ggtagtgtgt cacttgccca    840

ggcaactaca actagcaagg ggcttcctgc cacatcttca tcacgtgtgg cttcatgcta    900

tatcttcttc atagcatttt ctccttaagc cagagcatac tcatactcta cctgtccagg    960

gtgtattagg acactgaata gccctttagg aagccatgag gaattgccca agaccttgct   1020

atttggagca agattggctt ctgtcaagtc ttcagtttct ctttgtgtaa ataacagtaa   1080

tggctccatt ttgagttcta tgagcatcaa gatattaaca aagccctaga tggggcgtca   1140

aggtcattac tgaggatgag aagtacagtg gccaggagga cagggggctg ggtttttaca   1200

gtttggaacc acaacgtaga taagccactc ctttgcctgt gtcctaggac aacccctcct   1260

cgtagcagcc ttggtgggct cctatgtcca ttccactctc gtagagtatg tggtcaggac   1320

tgaagcagtg acgtcttatc aaacacttag ccagcacctg acttgtagga agcatcccac   1380

cagtgggagc tgtcctgaac                                                1400


<210> SEQ ID NO 31
<211> LENGTH: 324
<212> TYPE: DNA
<213> ORGANISM: Artificial Sequence
<220> FEATURE:
<223> OTHER INFORMATION: Homo sapiens

<400> SEQUENCE: 31

gaggaggagc tgcaggtgat tcagcctgac aagtccgtgt tggttgcagc tggagagaca     60

gccactctgc gctgcactgc gacctctctg atccctgtgg ggcccatcca gtggttcaga    120

ggagctggac caggccggga attaatctac aatcaaaaag aaggccactt cccccgggta    180

acaactgttt cagacctcac aaagagaaac aacatggact tttccatccg catcggtaac    240

atcaccccag cagatgccgg cacctactac tgtgtgaagt tccggaaagg gagccccgat    300

gacgtggagt ttaagtctgg agca                                           324


<210> SEQ ID NO 32
<211> LENGTH: 56
<212> TYPE: DNA
<213> ORGANISM: Artificial Sequence
<220> FEATURE:
<223> OTHER INFORMATION: PCR primer

<400> SEQUENCE: 32

tacctttaag aaggagatat acatgctcga gcacatctgc catgaaaatt ggatct         56


<210> SEQ ID NO 33
<211> LENGTH: 45
<212> TYPE: DNA
<213> ORGANISM: Artificial Sequence
<220> FEATURE:
<223> OTHER INFORMATION: PCR primer

<400> SEQUENCE: 33

atcacctgca gctcctcctc ccccgtggct cctgggaaga aagat                    45
```

<210> SEQ ID NO 34
<211> LENGTH: 45
<212> TYPE: DNA
<213> ORGANISM: Artificial Sequence
<220> FEATURE:
<223> OTHER INFORMATION: PCR primer

<400> SEQUENCE: 34
tcttcccagg agccacgggg gaggaggagc tgcaggtgat tcagc 45

<210> SEQ ID NO 35
<211> LENGTH: 45
<212> TYPE: DNA
<213> ORGANISM: Artificial Sequence
<220> FEATURE:
<223> OTHER INFORMATION: PCR primer

<400> SEQUENCE: 35
agtacataga cctctgttcc tgctccagac ttaaactcca cgtca 45

<210> SEQ ID NO 36
<211> LENGTH: 47
<212> TYPE: DNA
<213> ORGANISM: Artificial Sequence
<220> FEATURE:
<223> OTHER INFORMATION: PCR primer

<400> SEQUENCE: 36
tggagtttaa gtctggagca ggaacagagg tctatgtact cggtaag 47

<210> SEQ ID NO 37
<211> LENGTH: 58
<212> TYPE: DNA
<213> ORGANISM: Artificial Sequence
<220> FEATURE:
<223> OTHER INFORMATION: PCR primer

<400> SEQUENCE: 37
tcggttgtta gcagccggat ctcaggcggc cgcgttcagg acagctccca ctggtggg 58

<210> SEQ ID NO 38
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 38
agttccttcc ccgtggctcc tgg 23

<210> SEQ ID NO 39
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 39
agccacgggg aaggaactga agg 23

<210> SEQ ID NO 40
<211> LENGTH: 23
<212> TYPE: DNA
<213> ORGANISM: Artificial Sequence
<220> FEATURE:
<223> OTHER INFORMATION: sgRNA target sequence

```
<400> SEQUENCE: 40

caccttcagt tccttccccg tgg                                         23


<210> SEQ ID NO 41
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 41

aaatcagtgt ctgttgctgc tgg                                         23


<210> SEQ ID NO 42
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 42

cactttgacc tccttgttgc cgg                                         23


<210> SEQ ID NO 43
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 43

ttgacctcct tgttgccggt ggg                                         23


<210> SEQ ID NO 44
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 44

gggtcccacc ggcaacaagg agg                                         23


<210> SEQ ID NO 45
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 45

tgttgccggt gggacccatt agg                                         23


<210> SEQ ID NO 46
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 46

actcctctgt accacctaat ggg                                         23


<210> SEQ ID NO 47
<211> LENGTH: 23
```

<212> TYPE: DNA
<213> ORGANISM: Artificial Sequence
<220> FEATURE:
<223> OTHER INFORMATION: sgRNA target sequence

<400> SEQUENCE: 47
ctgtagatca acagccggct tgg 23

<210> SEQ ID NO 48
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 48
cgaaactgta gatcaacagc cgg 23

<210> SEQ ID NO 49
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 49
ctgttgatct acagtttcgc agg 23

<210> SEQ ID NO 50
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 50
tctgaaacat ttctaattcg agg 23

<210> SEQ ID NO 51
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 51
tactactaag agaaacaata tgg 23

<210> SEQ ID NO 52
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 52
ctggggtgac attactgata cgg 23

<210> SEQ ID NO 53
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 53
aatgtcaccc cagcagatgc tgg 23

<210> SEQ ID NO 54
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 54
gtagatgcca gcatctgctg ggg 23

<210> SEQ ID NO 55
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 55
cctgacacag aaatacaatc tgg 23

<210> SEQ ID NO 56
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 56
cacagaaata caatctggag ggg 23

<210> SEQ ID NO 57
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 57
acaatctgga gggggaacag agg 23

<210> SEQ ID NO 58
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 58
ggaacagagg tctatgtact cgg 23

<210> SEQ ID NO 59
<211> LENGTH: 18
<212> TYPE: DNA
<213> ORGANISM: Artificial Sequence
<220> FEATURE:
<223> OTHER INFORMATION: sgRNA sequence

<400> SEQUENCE: 59
gtcccaccgg caacaagg 18

<210> SEQ ID NO 60
<211> LENGTH: 22
<212> TYPE: DNA
<213> ORGANISM: Artificial Sequence
<220> FEATURE:
<223> OTHER INFORMATION: sgRNA sequence

<400> SEQUENCE: 60
tagggtccca ccggcaacaa gg 22

<210> SEQ ID NO 61
<211> LENGTH: 18
<212> TYPE: DNA
<213> ORGANISM: Artificial Sequence
<220> FEATURE:
<223> OTHER INFORMATION: sgRNA sequence

<400> SEQUENCE: 61
ccttgttgcc ggtgggac 18

<210> SEQ ID NO 62
<211> LENGTH: 22
<212> TYPE: DNA
<213> ORGANISM: Artificial Sequence
<220> FEATURE:
<223> OTHER INFORMATION: sgRNA sequence

<400> SEQUENCE: 62
aaacccttgt tgccggtggg ac 22

<210> SEQ ID NO 63
<211> LENGTH: 19
<212> TYPE: DNA
<213> ORGANISM: Artificial Sequence
<220> FEATURE:
<223> OTHER INFORMATION: sgRNA sequence

<400> SEQUENCE: 63
tagatgccag catctgctg 19

<210> SEQ ID NO 64
<211> LENGTH: 23
<212> TYPE: DNA
<213> ORGANISM: Artificial Sequence
<220> FEATURE:
<223> OTHER INFORMATION: sgRNA sequence

<400> SEQUENCE: 64
taggtagatg ccagcatctg ctg 23

<210> SEQ ID NO 65
<211> LENGTH: 19
<212> TYPE: DNA
<213> ORGANISM: Artificial Sequence
<220> FEATURE:
<223> OTHER INFORMATION: sgRNA sequence

<400> SEQUENCE: 65
cagcagatgc tggcatcta 19

<210> SEQ ID NO 66
<211> LENGTH: 23
<212> TYPE: DNA
<213> ORGANISM: Artificial Sequence
<220> FEATURE:
<223> OTHER INFORMATION: sgRNA sequence

<400> SEQUENCE: 66
aaaccagcag atgctggcat cta 23

<210> SEQ ID NO 67
<211> LENGTH: 132
<212> TYPE: DNA
<213> ORGANISM: Artificial Sequence
<220> FEATURE:
<223> OTHER INFORMATION: Synthesized sequence

<400> SEQUENCE: 67
gaattctaat acgactcact atagggggtc ttcgagaaga cctgttttag agctagaaat 60
agcaagttaa aataaggcta gtccgttatc aacttgaaaa agtggcaccg agtcggtgct 120
tttaaaggat cc 132

<210> SEQ ID NO 68
<211> LENGTH: 25
<212> TYPE: DNA
<213> ORGANISM: Artificial Sequence
<220> FEATURE:
<223> OTHER INFORMATION: PCR primer

<400> SEQUENCE: 68
catcaagcct gttccctcct tgtgt 25

<210> SEQ ID NO 69
<211> LENGTH: 25
<212> TYPE: DNA
<213> ORGANISM: Artificial Sequence
<220> FEATURE:
<223> OTHER INFORMATION: PCR primer

<400> SEQUENCE: 69
cttaaactcc acgtcatcgg ggctc 25

<210> SEQ ID NO 70
<211> LENGTH: 26
<212> TYPE: DNA
<213> ORGANISM: Artificial Sequence
<220> FEATURE:
<223> OTHER INFORMATION: PCR primer

<400> SEQUENCE: 70
tcaaaaagaa ggccacttcc cccggg 26

<210> SEQ ID NO 71
<211> LENGTH: 25
<212> TYPE: DNA
<213> ORGANISM: Artificial Sequence
<220> FEATURE:
<223> OTHER INFORMATION: PCR primer

<400> SEQUENCE: 71
caagctgtag agacagatgg gcagg 25

<210> SEQ ID NO 72
<211> LENGTH: 25
<212> TYPE: DNA
<213> ORGANISM: Artificial Sequence
<220> FEATURE:
<223> OTHER INFORMATION: PCR primer

<400> SEQUENCE: 72
gcaggacagt gagcaactga tgaca 25

<210> SEQ ID NO 73
<211> LENGTH: 25

<212> TYPE: DNA
<213> ORGANISM: Artificial Sequence
<220> FEATURE:
<223> OTHER INFORMATION: PCR primer

<400> SEQUENCE: 73
gcacagtggc ctaactacct tcctg 25

<210> SEQ ID NO 74
<211> LENGTH: 25
<212> TYPE: DNA
<213> ORGANISM: Artificial Sequence
<220> FEATURE:
<223> OTHER INFORMATION: PCR primer

<400> SEQUENCE: 74
ggtagtgccc atgaagctgg tactc 25

<210> SEQ ID NO 75
<211> LENGTH: 25
<212> TYPE: DNA
<213> ORGANISM: Artificial Sequence
<220> FEATURE:
<223> OTHER INFORMATION: PCR primer

<400> SEQUENCE: 75
ggccaccaca ttatggcttt ctcct 25

<210> SEQ ID NO 76
<211> LENGTH: 19
<212> TYPE: DNA
<213> ORGANISM: Artificial Sequence
<220> FEATURE:
<223> OTHER INFORMATION: PCR primer

<400> SEQUENCE: 76
ttgctgctgg ggattcgac 19

<210> SEQ ID NO 77
<211> LENGTH: 22
<212> TYPE: DNA
<213> ORGANISM: Artificial Sequence
<220> FEATURE:
<223> OTHER INFORMATION: PCR primer

<400> SEQUENCE: 77
ctgctggggt gacattactg at 22

<210> SEQ ID NO 78
<211> LENGTH: 19
<212> TYPE: DNA
<213> ORGANISM: Artificial Sequence
<220> FEATURE:
<223> OTHER INFORMATION: PCR primer

<400> SEQUENCE: 78
cctgacaagt ccgtgttgg 19

<210> SEQ ID NO 79
<211> LENGTH: 21
<212> TYPE: DNA
<213> ORGANISM: Artificial Sequence
<220> FEATURE:
<223> OTHER INFORMATION: PCR primer

<400> SEQUENCE: 79
ctcctctgaa ccactggatg g 21

<210> SEQ ID NO 80
<211> LENGTH: 26
<212> TYPE: DNA
<213> ORGANISM: Artificial Sequence
<220> FEATURE:
<223> OTHER INFORMATION: PCR primer

<400> SEQUENCE: 80
gtcttgagtt acaggctcat gtgggg 26

<210> SEQ ID NO 81
<211> LENGTH: 24
<212> TYPE: DNA
<213> ORGANISM: Artificial Sequence
<220> FEATURE:
<223> OTHER INFORMATION: PCR primer

<400> SEQUENCE: 81
cccattatac ctgctgcgag ccac 24

<210> SEQ ID NO 82
<211> LENGTH: 28
<212> TYPE: DNA
<213> ORGANISM: Artificial Sequence
<220> FEATURE:
<223> OTHER INFORMATION: PCR primer

<400> SEQUENCE: 82
ggtaaattta tccccaagat gcatggta 28

<210> SEQ ID NO 83
<211> LENGTH: 25
<212> TYPE: DNA
<213> ORGANISM: Artificial Sequence
<220> FEATURE:
<223> OTHER INFORMATION: PCR primer

<400> SEQUENCE: 83
acaaacattt cttcggtgct ttgcg 25

<210> SEQ ID NO 84
<211> LENGTH: 25
<212> TYPE: DNA
<213> ORGANISM: Artificial Sequence
<220> FEATURE:
<223> OTHER INFORMATION: PCR primer

<400> SEQUENCE: 84
tggggacagt ggacttgttt agagc 25

<210> SEQ ID NO 85
<211> LENGTH: 25
<212> TYPE: DNA
<213> ORGANISM: Artificial Sequence
<220> FEATURE:
<223> OTHER INFORMATION: PCR primer

<400> SEQUENCE: 85
agctatgtgg cttagcactc tgtgc 25

<210> SEQ ID NO 86
<211> LENGTH: 25
<212> TYPE: DNA
<213> ORGANISM: Artificial Sequence
<220> FEATURE:
<223> OTHER INFORMATION: PCR primer

<400> SEQUENCE: 86
cgaggaacgt attctcctgc gaaac 25

<210> SEQ ID NO 87
<211> LENGTH: 20
<212> TYPE: DNA
<213> ORGANISM: Artificial Sequence
<220> FEATURE:
<223> OTHER INFORMATION: PCR primer

<400> SEQUENCE: 87
gtcatccctt gcatcgtccg 20

<210> SEQ ID NO 88
<211> LENGTH: 20
<212> TYPE: DNA
<213> ORGANISM: Artificial Sequence
<220> FEATURE:
<223> OTHER INFORMATION: PCR primer

<400> SEQUENCE: 88
gtcatccctt gcatcgtccg 20

<210> SEQ ID NO 89
<211> LENGTH: 21
<212> TYPE: DNA
<213> ORGANISM: Artificial Sequence
<220> FEATURE:
<223> OTHER INFORMATION: PCR primer

<400> SEQUENCE: 89
acactgtcgt cattccatgc t 21

<210> SEQ ID NO 90
<211> LENGTH: 21
<212> TYPE: DNA
<213> ORGANISM: Artificial Sequence
<220> FEATURE:
<223> OTHER INFORMATION: PCR primer

<400> SEQUENCE: 90
cctgtgtgtg agacagcatc a 21

<210> SEQ ID NO 91
<211> LENGTH: 5346
<212> TYPE: DNA
<213> ORGANISM: Homo sapiens

<400> SEQUENCE: 91
ggggagcagg cgggggagcg ggcgggaagc agtgggagcg cgcgtgcgcg cggccgtgca 60
gcctgggcag tgggtcctgc ctgtgacgcg cggcggcggt cggtcctgcc tgtaacggcg 120
gcggcggctg ctgctccaga cacctgcggc ggcggcggcg accccgcggc gggcgcggag 180
atgtggcccc tggtagcggc gctgttgctg ggctcggcgt gctgcggatc agctcagcta 240
ctatttaata aaacaaaatc tgtagaattc acgttttgta atgacactgt cgtcattcca 300
tgctttgtta ctaatatgga ggcacaaaac actactgaag tatacgtaaa gtggaaattt 360
aaaggaagag atatttacac ctttgatgga gctctaaaca agtccactgt ccccactgac 420
tttagtagtg caaaaattga agtctcacaa ttactaaaag gagatgcctc tttgaagatg 480

```
gataagagtg atgctgtctc acacacagga aactacactt gtgaagtaac agaattaacc    540
agagaaggtg aaacgatcat cgagctaaaa tatcgtgttg tttcatggtt ttctccaaat    600
gaaaatattc ttattgttat tttcccaatt tttgctatac tcctgttctg ggacagtttt    660
ggtattaaaa cacttaaata tagatccggt ggtatggatg agaaaacaat tgctttactt    720
gttgctggac tagtgatcac tgtcattgtc attgttggag ccattctttt cgtcccaggt    780
gaatattcat taaagaatgc tactggcctt ggtttaattg tgacttctac agggatatta    840
atattacttc actactatgt gtttagtaca gcgattggat taacctcctt cgtcattgcc    900
atattggtta ttcaggtgat agcctatatc ctcgctgtgg ttggactgag tctctgtatt    960
gcggcgtgta taccaatgca tggccctctt ctgatttcag gtttgagtat cttagctcta   1020
gcacaattac ttggactagt ttatatgaaa tttgtggctt ccaatcagaa gactatacaa   1080
cctcctagga aagctgtaga ggaacccctt aatgcattca aagaatcaaa aggaatgatg   1140
aatgatgaat aactgaagtg aagtgatgga ctccgatttg gagagtagta agacgtgaaa   1200
ggaatacact tgtgtttaag caccatggcc ttgatgattc actgttgggg agaagaaaca   1260
agaaaagtaa ctggttgtca cctatgagac ccttacgtga ttgttagtta agtttttatt   1320
caaagcagct gtaatttagt taataaaata attatgatct atgttgtttg cccaattgag   1380
atccagtttt ttgttgttat ttttaatcaa ttaggggcaa tagtagaatg gacaatttcc   1440
aagaatgatg cctttcaggt cctagggcct ctggcctcta ggtaaccagt ttaaattggt   1500
tcagggtgat aactacttag cactgccctg gtgattaccc agagatatct atgaaaacca   1560
gtggcttcca tcaaaccttt gccaactcag gttcacagca gctttgggca gttatggcag   1620
tatggcatta gctgagaggt gtctgccact tctgggtcaa tggaataata aattaagtac   1680
aggcaggaat ttggttggga gcatcttgta tgatctccgt atgatgtgat attgatggag   1740
atagtggtcc tcattcttgg gggttgccat tcccacattc cccctcaac aaacagtgta   1800
acaggtcctt cccagattta gggtactttt attgatggat atgttttcct tttattcaca   1860
taacccttg aaaccctgtc ttgtcctcct gttacttgct tctgctgtac aagatgtagc   1920
accttttctc ctctttgaac atggtctagt gacacggtag caccagttgc aggaaggagc   1980
cagacttgtt ctcagagcac tgtgttcaca cttttcagca aaaatagcta tggttgtaac   2040
atatgtattc ccttcctctg atttgaaggc aaaaatctac agtgtttctt cacttctttt   2100
ctgatctggg gcatgaaaaa agcaagattg aaatttgaac tatgagtctc ctgcatggca   2160
acaaaatgtg tgtcaccatc aggccaacag gccagccctt gaatggggat ttattactgt   2220
tgtatctatg ttgcatgata aacattcatc accttcctcc tgtagtcctg cctcgtactc   2280
cccttcccct atgattgaaa agtaaacaaa acccacattt cctatcctgg ttagaagaaa   2340
attaatgttc tgacagttgt gatcgcctgg agtactttta gacttttagc attcgttttt   2400
tacctgtttg tggatgtgtg tttgtatgtg catacgtatg agataggcac atgcatcttc   2460
tgtatggaca aaggtggggt acctacagga gagcaaaggt taattttgtg cttttagtaa   2520
aaacatttaa atacaaagtt ctttattggg tggaattata tttgatgcaa atatttgatc   2580
acttaaaact tttaaaactt ctaggtaatt tgccacgctt tttgactgct caccaatacc   2640
ctgtaaaaat acgtaattct tcctgtttgt gtaataagat attcatattt gtagttgcat   2700
taataatagt tatttcttag tccatcagat gttcccgtgt gcctctttta tgccaaattg   2760
attgtcatat ttcatgttgg gaccaagtag tttgcccatg gcaaacctaa atttatgacc   2820
tgctgaggcc tctcagaaaa ctgagcatac tagcaagaca gctcttcttg aaaaaaaaaa   2880
```

```
tatgtataca caaatatata cgtatatcta tatatacgta tgtatataca cacatgtata   2940
ttcttccttg attgtgtagc tgtccaaaat aataacatat atagagggag ctgtattcct   3000
ttatacaaat ctgatggctc ctgcagcact ttttccttct gaaaatattt acattttgct   3060
aacctagttt gttactttaa aaatcagttt tgatgaaagg agggaaaagc agatggactt   3120
gaaaaagatc caagctccta ttagaaaagg tatgaaaatc tttatagtaa aatttttttat   3180
aaactaaagt tgtacctttt aatatgtagt aaactctcat ttatttgggg ttcgctcttg   3240
gatctcatcc atccattgtg ttctctttaa tgctgcctgc cttttgaggc attcactgcc   3300
ctagacaatg ccaccagaga tagtgggggga aatgccagat gaaaccaact cttgctctca   3360
ctagttgtca gcttctctgg ataagtgacc acagaagcag gagtcctcct gcttgggcat   3420
cattgggcca gttccttctc tttaaatcag atttgtaatg gctcccaaat tccatcacat   3480
cacatttaaa ttgcagacag tgttttgcac atcatgtatc tgttttgtcc cataaatatgc   3540
tttttactcc ctgatcccag tttctgctgt tgactcttcc attcagtttt atttattgtg   3600
tgttctcaca gtgacaccat ttgtcctttt ctgcaacaac ctttccagct actttgcca   3660
aattctattt gtcttctcct tcaaaacatt ctcctttgca gttcctcttc atctgtgtag   3720
ctgctctttt gtctcttaac ttaccattcc tatagtactt tatgcatctc tgcttagttc   3780
tattagtttt ttggccttgc tcttctcctt gattttaaaa ttccttctat agctagagct   3840
tttctttctt tcattctctc ttcctgcagt gttttgcata catcagaagc taggtacata   3900
agttaaatga ttgagagttg gctgtattta gatttatcac tttttaatag ggtgagcttg   3960
agagttttct ttctttctgt ttttttttt tgtttttttt ttttttttt ttttttttt   4020
ttttgactaa tttcacatgc tctaaaaacc ttcaaaggtg attatttttc tcctggaaac   4080
tccaggtcca ttctgtttaa atccctaaga atgtcagaat taaaataaca gggctatccc   4140
gtaattggaa atatttcttt tttcaggatg ctatagtcaa tttagtaagt gaccaccaaa   4200
ttgttatttg cactaacaaa gctcaaaaca cgataagttt actcctccat ctcagtaata   4260
aaaattaagc tgtaatcaac cttctaggtt tctcttgtct taaaatgggt attcaaaaat   4320
ggggatctgt ggtgtatgta tggaaacaca tactccttaa tttacctgtt gttggaaact   4380
ggagaaatga ttgtcgggca accgtttatt ttttattgta ttttatttgg ttgagggatt   4440
tttttataaa cagttttact tgtgtcatat tttaaaatta ctaactgcca tcacctgctg   4500
gggtcctttg ttaggtcatt ttcagtgact aatagggata atccaggtaa ctttgaagag   4560
atgagcagtg agtgaccagg cagtttttct gcctttagct ttgacagttc ttaattaaga   4620
tcattgaaga ccagctttct cataaatttc tctttttgaa aaaaagaaag catttgtact   4680
aagctcctct gtaagacaac atcttaaatc ttaaaagtgt tgttatcatg actggtgaga   4740
gaagaaaaca ttttgttttt attaaatgga gcattattta caaaaagcca ttgttgagaa   4800
ttagatccca catcgtataa atatctatta accattctaa ataaagagaa ctccagtgtt   4860
gctatgtgca agatcctctc ttggagcttt tttgcatagc aattaaaggt gtgctatttg   4920
tcagtagcca ttttttttgca gtgatttgaa gaccaaagtt gttttacagc tgtgttaccg   4980
ttaaaggttt ttttttttat atgtattaaa tcaatttatc actgtttaaa gctttgaata   5040
tctgcaatct ttgccaaggt actttttttat ttaaaaaaaa acataacttt gtaaatatta   5100
ccctgtaata ttatatatac ttaataaaac attttaagct attttgttgg gctatttcta   5160
ttgctgctac agcagaccac aagcacattt ctgaaaaatt taatttatta atgtattttt   5220
```

```
aagttgctta tattctaggt aacaatgtaa agaatgattt aaaatattaa ttatgaattt   5280

tttgagtata atacccaata agcttttaat tagagcagag ttttaattaa aagttttaaa   5340

tcagtc                                                              5346
```

<210> SEQ ID NO 92
<211> LENGTH: 323
<212> TYPE: PRT
<213> ORGANISM: Homo sapiens

<400> SEQUENCE: 92

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu
```

<210> SEQ ID NO 93
<211> LENGTH: 1928

<212> TYPE: DNA
<213> ORGANISM: Mus musculus

<400> SEQUENCE: 93

```
cccgggcagc ctgggcggcc gctcctgcct gtcactgctg cggcgctgct ggtcggtcgt     60
ttcccttgaa ggcagcagcg gaggcggcgg ctgctccaga cacctgcggc ggcgaccccc    120
cggcggcgcg gagatgtggc ccttggcggc ggcgctgttg ctgggctcct gctgctgcgg    180
ttcagctcaa ctactgttta gtaacgtcaa ctccatagag ttcacttcat gcaatgaaac    240
tgtggtcatc ccttgcatcg tccgtaatgt ggaggcgcaa agcaccgaag aaatgtttgt    300
gaagtggaag ttgaacaaat cgtatatttt catctatgat ggaaataaaa atagcactac    360
tacagatcaa aactttacca gtgcaaaaat ctcagtctca gacttaatca atggcattgc    420
ctctttgaaa atggataagc gcgatgccat ggtgggaaac tacacttgcg aagtgacaga    480
gttatccaga gaaggcaaaa cagttataga gctgaaaaac cgcacggcct tcaacactga    540
ccaaggatca gcctgttctt acgaggagga gaaaggaggt tgcaaattag tttcgtggtt    600
ttctccaaat gaaaagatcc tcattgttat tttcccaatt ttggctatac tcctgttctg    660
gggaaagttt ggtattttaa cactcaaata taaatccagc catacgaata agagaatcat    720
tctgctgctc gttgccgggc tggtgctcac agtcatcgtg gttgttggag ccatccttct    780
catcccagga gaaaagcccg tgaagaatgc ttctggactt ggcctcattg taatctctac    840
ggggatatta atactacttc agtacaatgt gtttatgaca gcttttggaa tgacctcttt    900
caccattgcc atattgatca ctcaagtgct gggctacgtc cttgctttgg tcgggctgtg    960
tctctgcatc atggcatgtg agccagtgca cggcccccttt ttgatttcag gtttggggat   1020
catagctcta gcagaactac ttggattagt ttatatgaag tttgtcgctt ccaaccagag   1080
gactatccaa cctcctagga ataggtgaag ggaagtgacg gactgtaact tggaagtcag   1140
aaatggaaga atacagttgt ctaagcacca ggtcttcacg actcacagct ggaaggaaca   1200
gacaacagta actgacttcc atccaggaaa acatgtcaca taaatgatta ctaagtttat   1260
attcaaagca gctgtacttt acataataaa aaaaatatga tgtgctgtgt aaccaattgg   1320
aatcccattt ttctattgtt tctactcaac taggggcaaa cgtttcaggg gcaacttcca   1380
agaatgatgc ttgttagatc ctagagtctc tgaacactga gtttaaattg attccgagtg   1440
agactcgcca agcactaacc tgagggttag ttacccagag atacctatga aaaacagtgg   1500
tatccagcaa gccttagtaa actcaggttg ccagcagctt tgccacttcc gctgctagct   1560
gaataacaag actgccactt ctgggtcata gtgatagaga ctgaagtaga aaaacgaatg   1620
tggttgggca aatcccgtgt ggcccctctg tgtgctatga tattgatggc actggtgtct   1680
tcattcttgg gggttgccat cattcacaca caccccttttg acatacagtg caccccagtt   1740
ttgaatacat tttttttgca ccctgtcccg ttctgctact ttgatttgcg ttatgatata   1800
tatatatata tataatacct tttctcctct ttaaacatgg tcctgtgaca caatagtcag   1860
ttgcagaaag gagccagact tattcgcaaa gcactgtgct caaactcttc agaaaaaaaa   1920
aaaaaaaa                                                            1928
```

<210> SEQ ID NO 94
<211> LENGTH: 324
<212> TYPE: PRT
<213> ORGANISM: Mus musculus

<400> SEQUENCE: 94

```
Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
    130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
                165                 170                 175

Gly Lys Phe Gly Ile Leu Thr Leu Lys Tyr Lys Ser Ser His Thr Asn
            180                 185                 190

Lys Arg Ile Ile Leu Leu Leu Val Ala Gly Leu Val Leu Thr Val Ile
        195                 200                 205

Val Val Val Gly Ala Ile Leu Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
            260                 265                 270

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
    290                 295                 300

Leu Val Tyr Met Lys Phe Val Ala Ser Asn Gln Arg Thr Ile Gln Pro
305                 310                 315                 320

Pro Arg Asn Arg
```

```
<210> SEQ ID NO 95
<211> LENGTH: 20
<212> TYPE: DNA
<213> ORGANISM: Artificial Sequence
<220> FEATURE:
<223> OTHER INFORMATION: PCR primer

<400> SEQUENCE: 95

taggcatgaa gtgaactcta                                              20


<210> SEQ ID NO 96
<211> LENGTH: 20
<212> TYPE: DNA
<213> ORGANISM: Artificial Sequence
```

<220> FEATURE:
<223> OTHER INFORMATION: PCR primer

<400> SEQUENCE: 96
aaactagagt tcacttcatg 20

<210> SEQ ID NO 97
<211> LENGTH: 19
<212> TYPE: DNA
<213> ORGANISM: Artificial Sequence
<220> FEATURE:
<223> OTHER INFORMATION: PCR primer

<400> SEQUENCE: 97
taggataagc gcgatgcca 19

<210> SEQ ID NO 98
<211> LENGTH: 19
<212> TYPE: DNA
<213> ORGANISM: Artificial Sequence
<220> FEATURE:
<223> OTHER INFORMATION: PCR primer

<400> SEQUENCE: 98
aaactggcat cgcgcttat 19

<210> SEQ ID NO 99
<211> LENGTH: 486
<212> TYPE: DNA
<213> ORGANISM: Artificial Sequence
<220> FEATURE:
<223> OTHER INFORMATION: Homo sapiens and Mus musculus

<400> SEQUENCE: 99
tatatgcaga ttgtaatgaa atatttttgt gtatgtattc caggttcagc tcaactactg 60
tttaataaaa caaaatctgt agaattcacg ttttgtaatg acactgtcgt cattccatgc 120
tttgttacta atatggaggc acaaaacact actgaagtat acgtaaagtg gaaatttaaa 180
ggaagagata tctacacctt tgatggagct ctaaacaagt ccactgtccc cactgacttt 240
agtagtgcaa aaattgaagt ctcacaatta ctaaaaggag atgcctcttt gaagatggat 300
aagagtgatg ctgtctcaca cacaggaaac tacacttgtg aagtaacaga attaaccaga 360
gaaggtgaaa cgatcataga gctgaaaaac cgcacgggta agtgacacag tttgcctgtt 420
ttgaaacgtg tgttgagata tggttgccac tgtgggagtg ctgtaaggtg gaaccttgca 480
gaagtc 486

<210> SEQ ID NO 100
<211> LENGTH: 1934
<212> TYPE: DNA
<213> ORGANISM: Artificial Sequence
<220> FEATURE:
<223> OTHER INFORMATION: Homo sapiens and Mus musculus

<400> SEQUENCE: 100
cccgggcagc ctgggcggcc gctcctgcct gtcactgctg cggcgctgct ggtcggtcgt 60
ttcccttgaa ggcagcagcg gaggcggcgg ctgctccaga cacctgcggc ggcgaccccc 120
cggcggcgcg gagatgtggc ccttggcggc ggcgctgttg ctgggctcct gctgctgcgg 180
ttcagctcaa ctactgttta ataaaacaaa atctgtagaa ttcacgtttt gtaatgacac 240
tgtcgtcatt ccatgctttg ttactaatat ggaggcacaa aacactactg aagtatacgt 300

```
aaagtggaaa tttaaaggaa gagatatcta cacctttgat ggagctctaa acaagtccac    360

tgtccccact gactttagta gtgcaaaaat tgaagtctca caattactaa aaggagatgc    420

ctctttgaag atggataaga gtgatgctgt ctcacacaca ggaaactaca cttgtgaagt    480

aacagaatta accagagaag gtgaaacgat catagagctg aaaaaccgca cggccttcaa    540

cactgaccaa ggatcagcct gttcttacga ggaggagaaa ggaggttgca aattagtttc    600

gtggttttct ccaaatgaaa agatcctcat tgttattttc ccaattttgg ctatactcct    660

gttctgggga aagtttggta ttttaacact caaatataaa tccagccata cgaataagag    720

aatcattctg ctgctcgttg ccgggctggt gctcacagtc atcgtggttg ttggagccat    780

ccttctcatc ccaggagaaa agcccgtgaa gaatgcttct ggacttggcc tcattgtaat    840

ctctacgggg atattaatac tacttcagta caatgtgttt atgacagctt ttggaatgac    900

ctctttcacc attgccatat tgatcactca agtgctgggc tacgtccttg ctttggtcgg    960

gctgtgtctc tgcatcatgg catgtgagcc agtgcacggc cccttttga tttcaggttt   1020

ggggatcata gctctagcag aactacttgg attagtttat atgaagtttg tcgcttccaa   1080

ccagaggact atccaacctc ctaggaatag gtgaagggaa gtgacggact gtaacttgga   1140

agtcagaaat ggaagaatac agttgtctaa gcaccaggtc ttcacgactc acagctggaa   1200

ggaacagaca acagtaactg acttccatcc aggaaaacat gtcacataaa tgattactaa   1260

gtttatattc aaagcagctg tactttacat aataaaaaaa atatgatgtg ctgtgtaacc   1320

aattggaatc ccatttttct attgtttcta ctcaactagg ggcaaacgtt tcaggggcaa   1380

cttccaagaa tgatgcttgt tagatcctag agtctctgaa cactgagttt aaattgattc   1440

cgagtgagac tcgccaagca ctaacctgag ggttagttac ccagagatac ctatgaaaaa   1500

cagtggtatc cagcaagcct tagtaaactc aggttgccag cagctttgcc acttccgctg   1560

ctagctgaat aacaagactg ccacttctgg gtcatagtga tagagactga agtagaaaaa   1620

cgaatgtggt tgggcaaatc ccgtgtggcc cctctgtgtg ctatgatatt gatggcactg   1680

gtgtcttcat tcttgggggt tgccatcatt cacacacacc cctttgacat acagtgcacc   1740

ccagttttga atacattttt tttgcaccct gtcccgttct gctactttga tttgcgttat   1800

gatatatata tatatatata atacctttc tcctctttaa acatggtcct gtgacacaat   1860

agtcagttgc agaaaggagc cagacttatt cgcaaagcac tgtgctcaaa ctcttcagaa   1920

aaaaaaaaaa aaaa                                                      1934


<210> SEQ ID NO 101
<211> LENGTH: 326
<212> TYPE: PRT
<213> ORGANISM: Artificial Sequence
<220> FEATURE:
<223> OTHER INFORMATION: Homo sapiens and Mus musculus

<400> SEQUENCE: 101

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
```

-continued

```
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Asn Arg Thr Ala Phe Asn Thr Asp Gln Gly Ser Ala Cys Ser
    130                 135                 140

Tyr Glu Glu Glu Lys Gly Gly Cys Lys Leu Val Ser Trp Phe Ser Pro
145                 150                 155                 160

Asn Glu Lys Ile Leu Ile Val Ile Phe Pro Ile Leu Ala Ile Leu Leu
                165                 170                 175

Phe Trp Gly Lys Phe Gly Ile Leu Thr Leu Lys Tyr Lys Ser Ser His
            180                 185                 190

Thr Asn Lys Arg Ile Ile Leu Leu Leu Val Ala Gly Leu Val Leu Thr
        195                 200                 205

Val Ile Val Val Val Gly Ala Ile Leu Leu Ile Pro Gly Glu Lys Pro
    210                 215                 220

Val Lys Asn Ala Ser Gly Leu Gly Leu Ile Val Ile Ser Thr Gly Ile
225                 230                 235                 240

Leu Ile Leu Leu Gln Tyr Asn Val Phe Met Thr Ala Phe Gly Met Thr
                245                 250                 255

Ser Phe Thr Ile Ala Ile Leu Ile Thr Gln Val Leu Gly Tyr Val Leu
            260                 265                 270

Ala Leu Val Gly Leu Cys Leu Cys Ile Met Ala Cys Glu Pro Val His
        275                 280                 285

Gly Pro Leu Leu Ile Ser Gly Leu Gly Ile Ile Ala Leu Ala Glu Leu
    290                 295                 300

Leu Gly Leu Val Tyr Met Lys Phe Val Ala Ser Asn Gln Arg Thr Ile
305                 310                 315                 320

Gln Pro Pro Arg Asn Arg
                325
```